(12) United States Patent
Edwards et al.

(10) Patent No.: US 10,105,489 B2
(45) Date of Patent: *Oct. 23, 2018

(54) MEDICAL INJECTOR WITH COMPLIANCE TRACKING AND MONITORING

(71) Applicant: kaleo, Inc., Richmond, VA (US)

(72) Inventors: Eric S. Edwards, Moseley, VA (US); Evan T. Edwards, Charlottesville, VA (US); Mark J. Licata, Doswell, VA (US); Paul F. Meyers, Fishers, IN (US); David A. Weinzierl, Andover, MN (US); T. Spencer Williamson, IV, Richmond, VA (US)

(73) Assignee: kaleo, Inc., Richmond, VA (US)

( * ) Notice: Subject to any disclaimer, the term of this patent is extended or adjusted under 35 U.S.C. 154(b) by 58 days.

This patent is subject to a terminal disclaimer.

(21) Appl. No.: 15/139,826

(22) Filed: Apr. 27, 2016

(65) Prior Publication Data

US 2016/0235916 A1 Aug. 18, 2016

Related U.S. Application Data

(63) Continuation of application No. 13/550,999, filed on Jul. 17, 2012, now Pat. No. 9,327,077, which is a
(Continued)

(51) Int. Cl.
*A61M 5/20* (2006.01)
*A61M 5/19* (2006.01)
(Continued)

(52) U.S. Cl.
CPC .............. *A61M 5/20* (2013.01); *A61M 5/19* (2013.01); *A61M 5/2033* (2013.01);
(Continued)

(58) Field of Classification Search
CPC ...... A61M 2205/581; A61M 2005/206; A61M 2205/50; A61M 2205/6027; A61M 2205/584; A61M 5/3204
See application file for complete search history.

(56) References Cited

U.S. PATENT DOCUMENTS 2,960,087 A  11/1960 Uytenbogaart
3,055,362 A  9/1962 Uytenbogaart
(Continued)

FOREIGN PATENT DOCUMENTS

AU  2004231230  6/2006
EP  1287840 A1  3/2003
(Continued)

OTHER PUBLICATIONS

Knapp, Louise. "A Faster Way to Call 911," Wired.com [online], [retrieved Jul. 26, 2017] Retrieved from the Internet <https://www.wired.com/2001/03/a-faster-way-to-call-911> (Mar. 10, 2001), 9 pages.
(Continued)

*Primary Examiner* — Emily Schmidt

(57) ABSTRACT

A system includes a medicament delivery device and a container configured to receive at least a portion of the medicament delivery device. The medicament delivery device includes an actuator and a first electronic circuit system. The actuator is configured to initiate delivery of a medicament into a body when the actuator is moved from a first position to a second position. The first electronic circuit system is configured to output a first electronic signal when the actuator is moved from the first position to the second position. The container includes a second electronic circuit system configured to receive the first electronic signal. The
(Continued)

second electronic circuit system is configured to output a second electronic signal associated with the first electronic signal.

21 Claims, 30 Drawing Sheets

Related U.S. Application Data continuation of application No. 12/017,405, filed on Jan. 22, 2008, now Pat. No. 8,226,610, which is a continuation-in-part of application No. 11/671,025, filed on Feb. 5, 2007, now Pat. No. 8,172,082, which is a continuation-in-part of application No. 11/621,236, filed on Jan. 9, 2007, now Pat. No. 7,731,686, which is a continuation-in-part of application No. 10/572,148, filed as application No. PCT/US2006/003415 on Feb. 1, 2006, now Pat. No. 7,749,194.

(60) Provisional application No. 60/648,822, filed on Feb. 1, 2005, provisional application No. 60/731,886, filed on Oct. 31, 2005, provisional application No. 60/885,969, filed on Jan. 22, 2007, provisional application No. 60/787,046, filed on Mar. 29, 2006.

(51) Int. Cl.
*A61M 5/32* (2006.01)
*A61M 15/00* (2006.01)
*G06F 19/00* (2018.01)
*A61M 5/315* (2006.01)
*A61M 5/24* (2006.01)
*A61M 5/31* (2006.01)

(52) U.S. Cl.
CPC ........ *A61M 5/2053* (2013.01); *A61M 5/2448* (2013.01); *A61M 5/315* (2013.01); *A61M 5/326* (2013.01); *A61M 15/0001* (2014.02); *A61M 15/008* (2014.02); *A61M 15/009* (2013.01); *G06F 19/00* (2013.01); *G06F 19/3468* (2013.01); *A61M 5/24* (2013.01); *A61M 5/3129* (2013.01); *A61M 5/3204* (2013.01); *A61M 2005/206* (2013.01); *A61M 2005/2013* (2013.01); *A61M 2005/2073* (2013.01); *A61M 2005/314* (2013.01); *A61M 2205/14* (2013.01); *A61M 2205/3331* (2013.01); *A61M 2205/3368* (2013.01); *A61M 2205/3553* (2013.01); *A61M 2205/3561* (2013.01); *A61M 2205/3569* (2013.01); *A61M 2205/3576* (2013.01); *A61M 2205/3584* (2013.01); *A61M 2205/3592* (2013.01); *A61M 2205/43* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2205/6018* (2013.01); *A61M 2205/6036* (2013.01); *A61M 2205/8206* (2013.01)

(56) References Cited

U.S. PATENT DOCUMENTS

| | | |
|---|---|---|
| 3,115,133 A | 12/1963 | Morando |
| 3,426,448 A | 2/1969 | Sarnoff |
| 3,688,765 A | 9/1972 | Gasaway |
| 3,768,472 A | 10/1973 | Hodosh et al. |
| 3,795,061 A | 3/1974 | Sarnoff et al. |
| 3,945,379 A | 3/1976 | Pritz et al. |
| 4,108,177 A | 8/1978 | Pistor |
| 4,124,024 A | 11/1978 | Schwebel et al. |
| 4,149,394 A | 4/1979 | Sornes |
| 4,226,235 A | 10/1980 | Sarnoff et al. |
| 4,360,019 A | 11/1982 | Portner et al. |
| 4,424,057 A | 1/1984 | House |
| 4,441,629 A | 4/1984 | Mackal |
| 4,484,910 A | 11/1984 | Sarnoff |
| 4,524,243 A | 6/1985 | Shapiro |
| 4,573,976 A | 3/1986 | Sampson et al. |
| 4,596,556 A | 6/1986 | Morrow et al. |
| 4,610,666 A | 9/1986 | Pizzino |
| 4,613,328 A | 9/1986 | Boyd |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,781,697 A | 11/1988 | Slaughter |
| 4,782,841 A | 11/1988 | Lopez |
| 4,784,652 A | 11/1988 | Wikström |
| 4,795,433 A | 1/1989 | Sarnoff |
| 4,822,340 A | 4/1989 | Kamstra |
| 4,826,489 A | 5/1989 | Haber |
| 4,853,521 A | 8/1989 | Claeys et al. |
| 4,865,582 A | 9/1989 | Sibalis |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,941,880 A | 7/1990 | Burns |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,062,603 A | 11/1991 | Smith et al. |
| 5,064,413 A | 11/1991 | McKinnon et al. |
| 5,071,353 A | 12/1991 | van der Wal |
| 5,085,642 A | 2/1992 | Sarnoff et al. |
| 5,092,843 A | 3/1992 | Monroe et al. |
| 5,125,898 A | 6/1992 | Kaufhold, Jr. et al. |
| 5,167,625 A | 12/1992 | Jacobsen et al. |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,281,198 A | 1/1994 | Haber et al. |
| 5,286,258 A | 2/1994 | Haber et al. |
| 5,298,023 A | 3/1994 | Haber et al. |
| 5,312,326 A | 5/1994 | Myers et al. |
| 5,314,406 A | 5/1994 | Arias et al. |
| 5,314,412 A | 5/1994 | Rex |
| 5,343,519 A | 8/1994 | Feldman |
| 5,344,407 A | 9/1994 | Ryan |
| 5,354,284 A | 10/1994 | Haber et al. |
| 5,356,376 A | 10/1994 | Milijasevic et al. |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,394,866 A | 3/1995 | Ritson et al. |
| 5,399,163 A | 3/1995 | Peterson et al. |
| 5,399,823 A * | 3/1995 | McCusker ........ A61M 5/14244 200/512 |
| 5,405,362 A | 4/1995 | Kramer et al. |
| 5,417,660 A | 5/1995 | Martin |
| 5,466,217 A | 11/1995 | Myers et al. |
| 5,505,192 A | 4/1996 | Samiotes et al. |
| 5,514,135 A | 5/1996 | Earle |
| 5,544,647 A | 8/1996 | Jewett et al. |
| 5,558,679 A | 9/1996 | Tuttle |
| 5,567,160 A | 10/1996 | Massino |
| 5,568,555 A | 10/1996 | Shamir |

(56) References Cited

U.S. PATENT DOCUMENTS

| | | |
|---|---|---|
| 5,569,192 A | 10/1996 | van der Wal |
| 5,584,815 A | 12/1996 | Pawelka et al. |
| 5,615,771 A | 4/1997 | Hollister |
| 5,616,132 A | 4/1997 | Newman |
| 5,642,731 A | 7/1997 | Kehr |
| 5,645,534 A | 7/1997 | Chanoch |
| 5,662,612 A | 9/1997 | Niehoff |
| 5,681,291 A | 10/1997 | Galli |
| 5,692,492 A | 12/1997 | Bruna et al. |
| 5,695,476 A | 12/1997 | Harris |
| 5,697,916 A | 12/1997 | Schraga |
| 5,716,338 A | 2/1998 | Hjertman et al. |
| 5,728,074 A | 3/1998 | Castellano et al. |
| 5,740,794 A | 4/1998 | Smith et al. |
| 5,752,235 A | 5/1998 | Kehr et al. |
| 5,772,635 A | 6/1998 | Dastur et al. |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,813,397 A | 9/1998 | Goodman et al. |
| 5,814,020 A | 9/1998 | Gross |
| 5,823,346 A | 10/1998 | Weiner |
| 5,823,363 A | 10/1998 | Cassel |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,988 A | 12/1998 | Davis |
| 5,852,590 A | 12/1998 | de la Huerga |
| 5,853,292 A | 12/1998 | Eggert et al. |
| 5,868,713 A | 2/1999 | Klippenstein |
| 5,868,721 A | 2/1999 | Marinacci |
| D407,487 S | 3/1999 | Greubel et al. |
| 5,905,653 A | 5/1999 | Higham et al. |
| 5,925,021 A | 7/1999 | Castellano et al. |
| 5,928,195 A | 7/1999 | Malamud |
| 5,941,857 A | 8/1999 | Nguyen et al. |
| 5,954,641 A | 9/1999 | Kehr et al. |
| 5,964,739 A | 10/1999 | Champ |
| 5,970,457 A | 10/1999 | Brant et al. |
| 5,971,953 A | 10/1999 | Bachynsky |
| 5,991,655 A | 11/1999 | Gross et al. |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,175,752 B1 | 1/2001 | Say |
| 6,179,812 B1 | 1/2001 | Botich et al. |
| 6,190,326 B1 | 2/2001 | McKinnon et al. |
| 6,192,891 B1 | 2/2001 | Gravel et al. |
| 6,193,695 B1 | 2/2001 | Rippstein, Jr. |
| 6,202,642 B1 * | 3/2001 | McKinnon .......... A61M 15/009 128/200.14 |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,249,717 B1 | 6/2001 | Nicholson et al. |
| 6,258,063 B1 | 7/2001 | Haar et al. |
| 6,259,654 B1 | 7/2001 | de la Huerga |
| 6,264,629 B1 | 7/2001 | Landau |
| 6,270,455 B1 | 8/2001 | Brown |
| 6,277,098 B1 | 8/2001 | Klitmose et al. |
| 6,285,757 B1 | 9/2001 | Carroll et al. |
| 6,297,737 B1 | 10/2001 | Irvin |
| 6,312,412 B1 | 11/2001 | Saied et al. |
| 6,317,630 B1 | 11/2001 | Gross et al. |
| 6,321,654 B1 | 11/2001 | Robinson |
| 6,334,070 B1 | 12/2001 | Nova et al. |
| 6,364,866 B1 | 4/2002 | Furr et al. |
| 6,371,939 B2 | 4/2002 | Bergens et al. |
| 6,377,848 B1 | 4/2002 | Garde et al. |
| 6,387,078 B1 | 5/2002 | Gillespie, III |
| 6,398,760 B1 | 6/2002 | Danby |
| 6,405,912 B2 | 6/2002 | Giannou |
| 6,411,567 B1 | 6/2002 | Niemiec et al. |
| 6,413,236 B1 | 7/2002 | Van Dyke |
| 6,425,897 B2 | 7/2002 | Overes et al. |
| 6,428,517 B1 | 8/2002 | Hochman et al. |
| 6,428,528 B2 | 8/2002 | Sadowski |
| 6,475,181 B1 | 11/2002 | Potter et al. |
| 6,478,769 B1 | 11/2002 | Parker |
| 6,482,185 B1 | 11/2002 | Hartmann |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Daily et al. |
| 6,530,904 B1 | 3/2003 | Edwards et al. |
| 6,535,714 B2 | 3/2003 | Melker et al. |
| 6,539,281 B2 | 3/2003 | Wan et al. |
| 6,540,672 B1 | 4/2003 | Simonsen et al. |
| 6,540,675 B2 | 4/2003 | Aceti et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,560,471 B1 | 5/2003 | Heller |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,589,229 B1 * | 7/2003 | Connelly .......... A61M 5/14248 604/65 |
| 6,595,956 B1 | 7/2003 | Gross et al. |
| 6,633,796 B1 | 10/2003 | Pool et al. |
| 6,641,566 B2 | 11/2003 | Douglas et al. |
| 6,645,181 B1 | 11/2003 | Lavi et al. |
| 6,648,850 B2 | 11/2003 | Landau |
| 6,659,980 B2 | 12/2003 | Moberg et al. |
| 6,676,630 B2 | 1/2004 | Landau et al. |
| 6,679,862 B2 | 1/2004 | Diaz et al. |
| 6,689,093 B2 | 2/2004 | Landau |
| 6,702,778 B2 | 3/2004 | Hill et al. |
| 6,707,763 B2 | 3/2004 | Osberg et al. |
| 6,708,050 B2 | 3/2004 | Carim |
| 6,722,916 B2 | 4/2004 | Buccinna et al. |
| 6,723,077 B2 | 4/2004 | Pickup et al. |
| 6,726,661 B2 | 4/2004 | Munk et al. |
| 6,736,796 B2 | 5/2004 | Shekalim |
| 6,743,635 B2 | 6/2004 | Neel et al. |
| 6,749,437 B2 | 6/2004 | Chan |
| 6,752,781 B2 | 6/2004 | Landau et al. |
| 6,767,336 B1 | 7/2004 | Kaplan |
| 6,770,052 B2 | 8/2004 | Hill et al. |
| 6,770,056 B2 | 8/2004 | Price et al. |
| 6,783,509 B1 | 8/2004 | Landau et al. |
| 6,786,875 B2 | 9/2004 | Barker et al. |
| 6,786,885 B2 | 9/2004 | Hochman et al. |
| 6,793,646 B1 | 9/2004 | Giambattista et al. |
| 6,803,856 B1 | 10/2004 | Murphy et al. |
| 6,808,514 B2 | 10/2004 | Schneider et al. |

(56) References Cited

U.S. PATENT DOCUMENTS

| | | |
|---|---|---|
| 6,809,653 B1 | 10/2004 | Mann et al. |
| 6,817,986 B2 | 11/2004 | Slate et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,923,764 B2 | 8/2005 | Aceti et al. |
| 6,936,029 B2 | 8/2005 | Mann et al. |
| 6,937,150 B2 | 8/2005 | Medema et al. |
| 6,942,646 B2 | 9/2005 | Langley et al. |
| 6,946,299 B2 | 9/2005 | Neel et al. |
| 6,949,082 B2 | 9/2005 | Langley et al. |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,048,141 B2 | 5/2006 | Abdulhay |
| 7,072,738 B2 | 7/2006 | Bonney et al. |
| 7,074,211 B1 | 7/2006 | Heiniger et al. |
| 7,093,595 B2 | 8/2006 | Nesbitt |
| 7,104,972 B2 | 9/2006 | Moller et al. |
| 7,113,101 B2 | 9/2006 | Peterson et al. |
| 7,116,233 B2 | 10/2006 | Zhurin |
| 7,126,879 B2 | 10/2006 | Snyder |
| 7,158,011 B2 | 1/2007 | Brue |
| 7,191,916 B2 | 3/2007 | Clifford et al. |
| 7,229,458 B2 | 6/2007 | Boecker et al. |
| 7,278,983 B2 | 10/2007 | Ireland et al. |
| 7,299,981 B2 | 11/2007 | Hickle et al. |
| 7,343,914 B2 | 3/2008 | Abrams et al. |
| 7,351,223 B2 | 4/2008 | Call |
| 7,416,540 B2 | 8/2008 | Edwards et al. |
| 7,544,188 B2 | 6/2009 | Edwards et al. |
| 7,630,788 B1 | 12/2009 | Reese |
| 7,648,482 B2 | 1/2010 | Edwards et al. |
| 7,648,483 B2 | 1/2010 | Edwards et al. |
| 7,670,328 B2 | 3/2010 | Miller et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,871,393 B2 | 1/2011 | Monroe |
| 7,918,823 B2 | 4/2011 | Edwards et al. |
| 7,938,802 B2 | 5/2011 | Bicknell et al. |
| 7,947,017 B2 | 5/2011 | Edwards et al. |
| 8,021,344 B2 | 9/2011 | Edwards et al. |
| 8,123,719 B2 | 2/2012 | Edwards et al. |
| 8,149,111 B2 | 4/2012 | Monroe |
| 8,172,082 B2 | 5/2012 | Edwards et al. |
| 8,206,360 B2 | 6/2012 | Edwards et al. |
| 8,212,658 B2 | 7/2012 | Monroe |
| 8,226,610 B2 | 7/2012 | Edwards et al. |
| 8,231,573 B2 | 7/2012 | Edwards et al. |
| 8,424,517 B2 | 4/2013 | Sutherland et al. |
| 8,544,645 B2 | 10/2013 | Edwards et al. |
| 8,556,865 B2 | 10/2013 | Krulevitch et al. |
| 8,556,867 B2 | 10/2013 | Krulevitch et al. |
| 8,622,973 B2 | 1/2014 | Edwards et al. |
| 8,627,816 B2 | 1/2014 | Edwards et al. |
| 8,690,827 B2 | 4/2014 | Edwards et al. |
| 8,789,748 B2 | 6/2014 | Waugh et al. |
| 8,849,449 B2 | 9/2014 | Waugh et al. |
| 8,899,987 B2 | 12/2014 | Edwards et al. |
| 8,926,594 B2 | 1/2015 | Edwards et al. |
| 8,932,252 B2 | 1/2015 | Edwards et al. |
| 8,939,943 B2 | 1/2015 | Edwards et al. |
| 9,022,980 B2 | 5/2015 | Edwards et al. |
| 9,084,849 B2 | 7/2015 | Edwards et al. |
| 9,149,579 B2 | 10/2015 | Edwards et al. |
| 9,173,999 B2 | 11/2015 | Edwards et al. |
| 2001/0005781 A1 | 6/2001 | Bergens et al. |
| 2002/0000225 A1 | 1/2002 | Schuler et al. |
| 2002/0072784 A1 | 6/2002 | Sheppard, Jr. et al. |
| 2002/0074345 A1 | 6/2002 | Schneider et al. |
| 2002/0076679 A1 | 6/2002 | Aman |
| 2002/0079326 A1 | 6/2002 | Fuchs |
| 2002/0090601 A1 | 7/2002 | Strupat et al. |
| 2002/0096543 A1 | 7/2002 | Juselius |
| 2002/0183721 A1 | 12/2002 | Santini, Jr. et al. |
| 2003/0028145 A1 | 2/2003 | Duchon et al. |
| 2003/0040717 A1 | 2/2003 | Saulenas et al. |
| 2003/0060765 A1 | 3/2003 | Campbell et al. |
| 2003/0065536 A1* | 4/2003 | Hansen ............ A61B 5/14532 705/2 |
| 2003/0106824 A1 | 6/2003 | Wilmot et al. |
| 2003/0130853 A1 | 7/2003 | Maire |
| 2003/0132128 A1 | 7/2003 | Mazur |
| 2003/0135388 A1 | 7/2003 | Martucci et al. |
| 2003/0233070 A1 | 12/2003 | De La Serna et al. |
| 2004/0015125 A1 | 1/2004 | Alexandre et al. |
| 2004/0019326 A1 | 1/2004 | Gilbert et al. |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0054327 A1 | 3/2004 | Gillespie, III |
| 2004/0069667 A1 | 4/2004 | Tomellini et al. |
| 2004/0084047 A1 | 5/2004 | Hickle |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0212509 A1 | 10/2004 | Zweig |
| 2004/0215369 A1 | 10/2004 | Rosenblum |
| 2004/0220524 A1 | 11/2004 | Sadowski et al. |
| 2004/0225255 A1 | 11/2004 | Ono |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0055014 A1 | 3/2005 | Coppeta et al. |
| 2005/0062603 A1 | 3/2005 | Fuerst et al. |
| 2005/0088289 A1 | 4/2005 | Rochkind |
| 2005/0090781 A1 | 4/2005 | Baba et al. |
| 2005/0134433 A1 | 6/2005 | Sweeney, II |
| 2005/0137530 A1 | 6/2005 | Campbell et al. |
| 2005/0148931 A1 | 7/2005 | Juhasz |
| 2005/0148945 A1 | 7/2005 | Chen |
| 2005/0150488 A1 | 7/2005 | Dave |
| 2005/0159705 A1 | 7/2005 | Crawford et al. |
| 2005/0165360 A1 | 7/2005 | Stamp |
| 2005/0168337 A1 | 8/2005 | Mahoney |
| 2005/0171477 A1 | 8/2005 | Rubin et al. |
| 2005/0182358 A1 | 8/2005 | Veit et al. |
| 2005/0183982 A1 | 8/2005 | Giewercer |
| 2005/0192530 A1 | 9/2005 | Castellano |
| 2005/0197654 A1 | 9/2005 | Edman et al. |
| 2005/0203466 A1 | 9/2005 | Hommann et al. |
| 2005/0209558 A1 | 9/2005 | Marx |
| 2005/0209569 A1 | 9/2005 | Ishikawa et al. |
| 2005/0261742 A1 | 11/2005 | Nova et al. |
| 2005/0267403 A1 | 12/2005 | Landau et al. |
| 2005/0273059 A1 | 12/2005 | Mernoe et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0074519 A1 | 4/2006 | Barker et al. |
| 2006/0089592 A1 | 4/2006 | Kadhiresan et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129089 A1 | 6/2006 | Stamp |
| 2006/0129090 A1 | 6/2006 | Moberg et al. |
| 2006/0169611 A1 | 8/2006 | Prindle |
| 2006/0169773 A1 | 8/2006 | Lyons et al. |

(56) References Cited

U.S. PATENT DOCUMENTS

| | | |
|---|---|---|
| 2006/0189938 A1 | 8/2006 | Hommann et al. |
| 2006/0200077 A1 | 9/2006 | Righi et al. |
| 2006/0204939 A1 | 9/2006 | Bardsley et al. |
| 2006/0247578 A1 | 11/2006 | Arguendas et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0074722 A1 | 4/2007 | Giroux et al. |
| 2007/0149954 A1 | 6/2007 | Hood et al. |
| 2007/0184847 A1 | 8/2007 | Hansen et al. |
| 2007/0186923 A1 | 8/2007 | Poutiatine et al. |
| 2007/0210147 A1 | 9/2007 | Morrone et al. |
| 2007/0213598 A1 | 9/2007 | Howard et al. |
| 2007/0233001 A1 | 10/2007 | Burroughs et al. |
| 2007/0239116 A1 | 10/2007 | Follman et al. |
| 2007/0239140 A1 | 10/2007 | Chechelski et al. |
| 2007/0260210 A1 | 11/2007 | Conroy |
| 2007/0285238 A1 | 12/2007 | Batra |
| 2007/0285258 A1 | 12/2007 | Hartman |
| 2008/0111685 A1 | 5/2008 | Olson et al. |
| 2008/0160492 A1 | 7/2008 | Campbell et al. |
| 2008/0228143 A1 | 9/2008 | Stamp |
| 2008/0230057 A1 | 9/2008 | Sutherland |
| 2008/0234625 A1 | 9/2008 | Dacquay et al. |
| 2009/0030285 A1 | 1/2009 | Andersen |
| 2009/0062728 A1 | 3/2009 | Woo |
| 2009/0131875 A1 | 5/2009 | Green |
| 2009/0143761 A1 | 6/2009 | Cantor et al. |
| 2009/0194104 A1 | 8/2009 | Van Sickle |
| 2009/0240200 A1 | 9/2009 | Heneveld et al. |
| 2010/0111066 A1 | 5/2010 | Mehta |
| 2010/0160894 A1 | 6/2010 | Julian et al. |
| 2010/0192948 A1 | 8/2010 | Sutherland et al. |
| 2010/0211005 A1 | 8/2010 | Edwards et al. |
| 2010/0214095 A1 | 8/2010 | Davide |
| 2010/0250280 A1 | 9/2010 | Sutherland |
| 2010/0250697 A1 | 9/2010 | Hansen et al. |
| 2010/0267357 A1 | 10/2010 | Holmstrom et al. |
| 2010/0268303 A1 | 10/2010 | Mitchell et al. |
| 2010/0286612 A1 | 11/2010 | Cirillo |
| 2011/0046698 A1 | 2/2011 | Kivi et al. |
| 2011/0144574 A1 | 6/2011 | Kamen et al. |
| 2011/0264033 A1 | 10/2011 | Jensen et al. |
| 2011/0295215 A1 | 12/2011 | Nielsen et al. |
| 2012/0052837 A1 | 3/2012 | Reich et al. |
| 2012/0071819 A1 | 3/2012 | Bruggemann et al. |
| 2012/0081225 A1 | 4/2012 | Waugh et al. |
| 2012/0083666 A1 | 4/2012 | Waugh et al. |
| 2012/0101444 A1 | 4/2012 | Muller-Pathle et al. |
| 2012/0107783 A1 | 5/2012 | Julian et al. |
| 2012/0165747 A1 | 6/2012 | Lanin et al. |
| 2013/0079725 A1 | 3/2013 | Shang et al. |
| 2013/0184649 A1 | 7/2013 | Edwards et al. |
| 2013/0190692 A1 | 7/2013 | Edwards et al. |
| 2013/0266919 A1 | 10/2013 | Baker et al. |
| 2013/0317477 A1 | 11/2013 | Edwards et al. |
| 2014/0243749 A1 | 8/2014 | Edwards et al. |
| 2014/0276385 A1 | 9/2014 | Baker et al. |
| 2014/0296824 A1 | 10/2014 | Edwards et al. |
| 2014/0371714 A1 | 12/2014 | Edwards et al. |
| 2015/0011973 A1 | 1/2015 | Edwards et al. |
| 2015/0190591 A1 | 7/2015 | Edwards et al. |
| 2015/0196711 A1 | 7/2015 | Edwards et al. |
| 2015/0294551 A1 | 10/2015 | Edwards et al. |
| 2016/0121056 A1 | 5/2016 | Edwards et al. |
| 2016/0166768 A1 | 6/2016 | Edwards et al. |
| 2016/0184535 A1 | 6/2016 | Edwards et al. |
| 2017/0049954 A1 | 2/2017 | Edwards et al. |
| 2017/0092101 A1 | 3/2017 | Edwards et al. |
| 2017/0312433 A1 | 11/2017 | Edwards et al. |
| 2018/0102066 A1 | 4/2018 | Edwards et al. |

FOREIGN PATENT DOCUMENTS

| | | |
|---|---|---|
| EP | 1462134 A1 | 9/2004 |
| EP | 1712178 A2 | 10/2006 |
| JP | 2006-034845 | 2/2006 |
| WO | WO 93/02720 | 2/1993 |
| WO | WO 95/26009 | 9/1995 |
| WO | WO 96/25965 | 8/1996 |
| WO | WO 97/30742 | 8/1997 |
| WO | WO 98/52632 | 11/1998 |
| WO | WO 99/07425 | 2/1999 |
| WO | WO 99/10031 | 3/1999 |
| WO | WO 99/43283 | 9/1999 |
| WO | WO 2001/003758 | 1/2001 |
| WO | WO 2001/024690 | 4/2001 |
| WO | WO 2001/026020 | 4/2001 |
| WO | WO 2001/041849 | 6/2001 |
| WO | WO 2001/088828 | 11/2001 |
| WO | WO 2001/093926 | 12/2001 |
| WO | WO 2003/057283 | 7/2003 |
| WO | WO 2003/095001 | 11/2003 |
| WO | WO 2004/041330 | 5/2004 |
| WO | WO 2005/050526 | 6/2005 |
| WO | WO 2005/074790 | 8/2005 |
| WO | WO 2005/077441 | 8/2005 |
| WO | WO 2006/045525 | 5/2006 |
| WO | WO 2006/085175 | 8/2006 |
| WO | WO 2006/109778 | 10/2006 |
| WO | WO 2006/123956 | 11/2006 |
| WO | WO 2006/125692 | 11/2006 |
| WO | WO 2007/087304 | 8/2007 |
| WO | WO 2007/088444 | 8/2007 |
| WO | WO 2008/005315 | 1/2008 |
| WO | WO 2008/008451 | 1/2008 |
| WO | WO 2008/148864 | 12/2008 |
| WO | WO 2010/114392 | 10/2010 |
| WO | WO 2012/063172 | 5/2012 |
| WO | WO 2013/043063 | 3/2013 |
| WO | WO 2013/044172 | 3/2013 |

OTHER PUBLICATIONS

Libov, Charlotte. "EpiPen 101," Everyday Health [online], [retrieved Jul. 26, 2017] Retrieved from the Internet <http://www.everydayhealth.com/allergy/epipen-101.aspx> (Feb. 23, 2012), 2 pages.

Office Action for U.S. Appl. No. 14/148,268 dated Jun. 15, 2017.

Office Action for Australia Patent Application No. 2015249064, dated Aug. 25, 2017.

"Solutions for Medical Devices," 3M Brochure, ©3M, (2006), 80-6201-3490-0, 8 pages.

"Flexible circuits / Flex circuits / Flexible Technology Ltd.," Flexible Technology Limited [online] [retrieved on Aug. 28, 2006] Retrieved from the Internet <URL: http://www.flexibletechnology.com/ >, 2 pages.

"Flexible circuits capabilities of Flexible Technology Limited," Our Flexible Circuits Capabilities [online] [retrieved on Aug. 28, 2006] Retrieved from the Internet <URL: http://www.flexibletechnology.com/Flexible circuits Capability.htm >, 2 pages.

"Flex Circuits/flexible circuits design guide," [online] [retrieved on Aug. 28, 2006] Retrieved from the Internet <URL: http://flexiblecircuit.co.uk/Flex Circuits Design Guide.htm >, 7 pages.

"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html >, 3 pages.

"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1 >, 3 pages.

RFID Gazette, "Smart Labels in Healthcare," Sep. 29, 2005 [online] [retrieved on Nov. 28, 2006] Retrieved from the Internet <URL: http://www.rfidagazeete.org/2005/09/smart labels in.html >, 2 pages.

"Merck Serono Launches easypod(R), First Electronic Growth Hormone Injection Device," Jan. 30, 2007 [online] [retrieved on

(56) References Cited

OTHER PUBLICATIONS

Feb. 5, 2007] Retrieved from the Internet <URL: http://www.biz.yahoo.com/prnews/070130/ukm028.html?.v=8>, 3 pages.
Scholz, O., "Drug depot in a tooth," [online] [retrieved on Feb. 6, 2007] Retrieved from the Internet <URL: http://www.fraunhofer.de/fhg/EN/press/pi/2007/02Mediendienst22007Thema2.jsp?print=true>, 1 page.
Heartsine Technology, samaritan™ PAD Accessories [online] [retrieved on Jun. 1, 2007] Retrieved from the Internet <URL: http://www.heartsine.com/aboutsam-accessories.htm>, 4 pages.
CliniSense Corporation, "Drug delivery devices a potentially harsh environment for drugs," Stability [online] [retrieved on Jun. 1, 2007] Retrieved from the Internet <URL: http://www.clinisense.com/devices.htm>, 2 pages.
CliniSense Corporation, "LifeTrack Technology A new method to detect improper storage." Stability [online] [retrieved on Jun. 1, 2007] Retrieved from the Internet <URL: http://www.clinisense.com/tech.htm>, 2 pages.
AED Professionals™ Brochure [online] [retrieved on Jun. 1, 2007] Retrieved from the Internet <URL: http://www.aedprofessionals.com>, 4 pages.
Ruppar, D., "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-online.com/drugdelivery/200702/templates/pageviewer_print?pg=44&pm=8 >, 8 pages.
Meridian Medical Technologies, Inc., "Pralidoxime Chloride Trainer," 2006. [retrieved on Feb. 16, 2007] Retrieved from the Internet <URL: http://www.meridianmeds.com/auto-injectors/2pamcl_trainer.html/>, 1 pages.
Gosbee, L. L., "Nuts! I Can't Figure Out How to Use My Life-Saving Epinephrine Auto-Injector," Joint Commision Journal on Quality and Safety, 30(4):220-223 (Apr. 2004).
Amgen, "Using Aranesp prefilled SureClick autoinjector is a simple 3-step process," 2006. [retrieved on Feb. 16, 2007] Retrieved from the Internet <URL: http://www.aranesp.com/patient/cia/sureclick/using_three_steps.jsp/>, 4 pages.
Apple, Inc., "Bluetooth Accessory Design Guidelines for Apple Products," Release R7, (Sep. 18, 2013), 40 pages.
Stuart, M., "Cellnovo's Mobile Health Approach to Diabetes Care," In Vivo: The Business & Medicine Report, (Dec. 2010), pp. 40-44.
Office Action for Israel Patent Application No. 184552, dated Jul. 28, 2011.
International Search Report and Written Opinion for International Patent Application No. PCT/US06/03415, dated Jul. 13, 2006, 10 pages.
Search Report for European Patent Application No. 09150135.3, dated Mar. 15, 2010.
Office Action for European Patent Application No. 09150135.3, dated Jul. 11, 2011.
Examination Report for British Patent Application No. 0818178.6, dated Mar. 23, 2009.
Examination Report for British Patent Application No. 0818178.6, dated Jul. 9, 2009.
Examination Report for British Patent Application No. 0905194.7, dated May 8, 2009.
Office Action for U.S. Appl. No. 10/572,148, dated Jun. 19, 2009.
Office Action for U.S. Appl. No. 10/572,148, dated Feb. 3, 2010.
Office Action for Japanese Patent Application No. 2009-502964, dated May 23, 2011.
Office Action for Japanese Patent Application No. 2009-502964, dated May 21, 2012 (English Translation).
Search and Examination Report for British Patent Application No. 1104754.5, dated May 18, 2011.
Office Action for U.S. Appl. No. 11/621,236, dated Feb. 3, 2009.
Office Action for U.S. Appl. No. 11/621,236, dated Jul. 1, 2009.
Office Action for U.S. Appl. No. 11/621,236, dated Jan. 11, 2010.
Search and Examination Report for British Patent Application No. 1108993.5, dated Jun. 17, 2011.
Office Action for U.S. Appl. No. 11/671,025, dated Mar. 24, 2011.
Office Action for U.S. Appl. No. 11/671,025, dated Sep. 8, 2011.
Examination Report for British Patent Application No. 1019599.8, dated Feb. 7, 2012.
Office Action for U.S. Appl. No. 12/119,016, dated Nov. 3, 2011.
Search and Examination Report for British Patent Application No. 1213906.9, dated Sep. 21, 2012.
Office Action for U.S. Appl. No. 12/794,020, dated Oct. 25, 2011.
Office Action for U.S. Appl. No. 13/924,037, dated Feb. 13, 2014.
Office Action for U.S. Appl. No. 14/470,165, dated May 26, 2015.
Office Action for U.S. Appl. No. 14/664,426, dated Jun. 9, 2015.
Office Action for U.S. Appl. No. 12/017,405, dated Dec. 7, 2011.
International Search Report and Written Opinion for International Patent Application No. PCT/US2008/051612, dated Dec. 9, 2008, 7 pages.
Office Action for U.S. Appl. No. 13/550,999, dated Apr. 18, 2014, 17 pages.
Office Action for U.S. Appl. No. 13/550,999, dated Nov. 3, 2014, 11 pages.
Office Action for U.S. Appl. No. 13/550,999, dated Jul. 21, 2015.
Office Action for U.S. Appl. No. 14/665,659, dated Jun. 23, 2015.
Office Action for U.S. Appl. No. 12/615,636, dated Jan. 25, 2012.
International Search Report and Written Opinion for International Patent Application No. PCT/US09/63983, dated Feb. 25, 2010.
International Search Report and Written Opinion for International Patent Application No. PCT/US2013/078071, dated May 6, 2014, 19 pages.
Final Office Action for U.S. Appl. No. 14/993,234, dated Nov. 2, 2017.
Office Action for U.S. Appl. No. 14/148,268 dated Dec. 13, 2017.

* cited by examiner

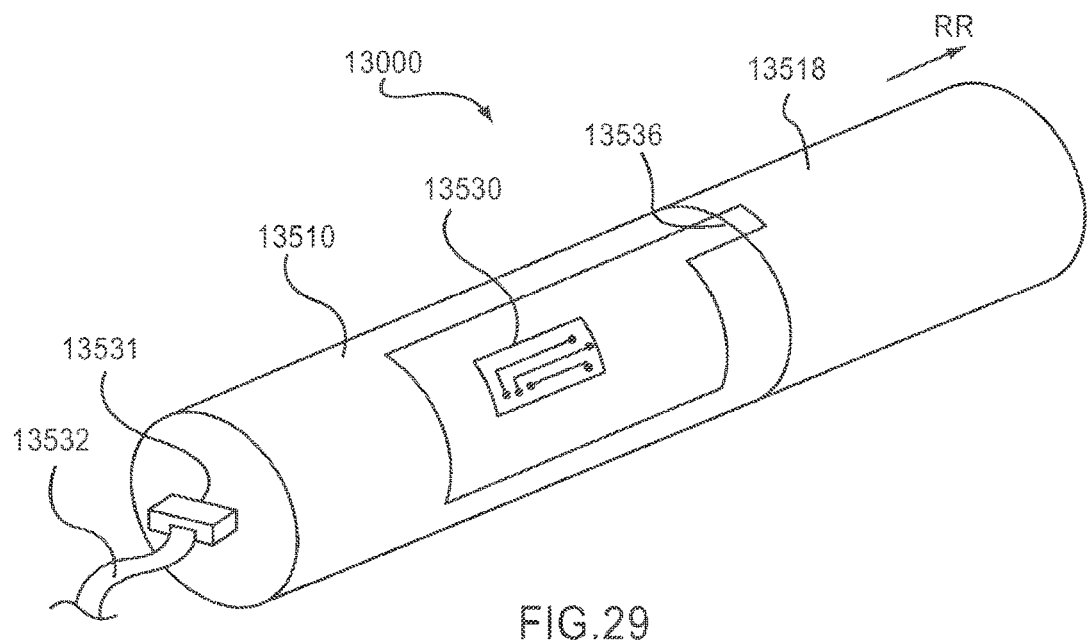
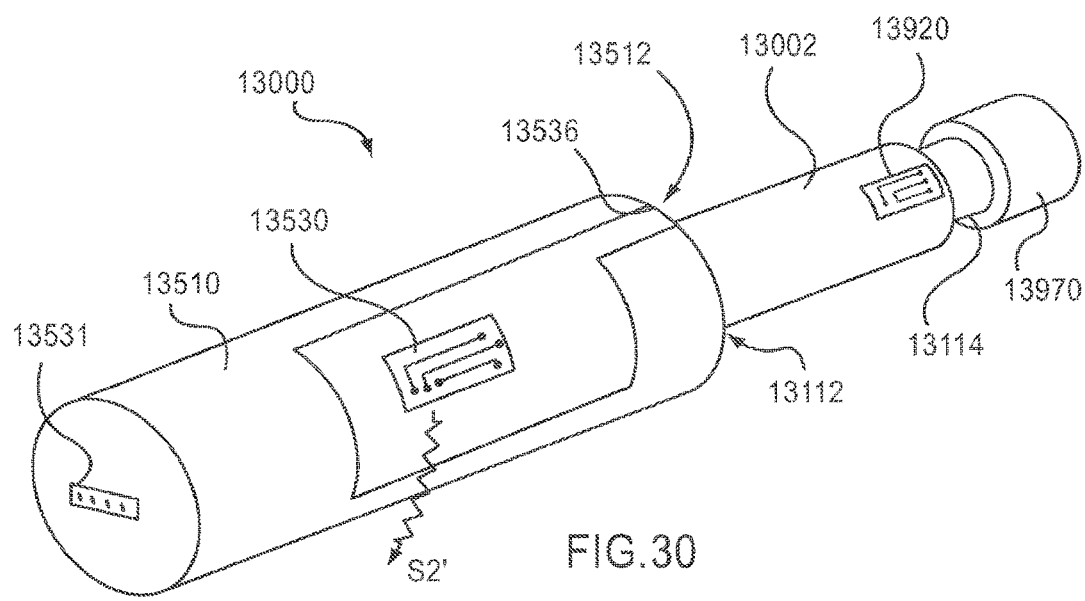

MEDICAL INJECTOR WITH COMPLIANCE TRACKING AND MONITORING

CROSS-REFERENCE TO RELATED APPLICATIONS

This application is a continuation of U.S. patent application Ser. No. 13/550,999, entitled "Medical Injector With Compliance Tracking and Monitoring," filed Jul. 17, 2012, which is a continuation of U.S. patent application Ser. No. 12/017,405, now U.S. Pat. No. 8,226,610, entitled "Medical Injector With Compliance Tracking and Monitoring," filed Jan. 22, 2008, which is a continuation-in-part of U.S. patent application Ser. No. 11/671,025, now U.S. Pat. No. 8,172,082, entitled "Devices, Systems and Methods for Medicament Delivery," filed Feb. 5, 2007, which is a continuation-in-part of U.S. patent application Ser. No. 11/621,236, now U.S. Pat. No. 7,731,686, entitled "Devices, Systems and Methods for Medicament Delivery," filed Jan. 9, 2007, which is a continuation-in-part of U.S. patent application Ser. No. 10/572,148, now U.S. Pat. No. 7,749,194, entitled "Devices, Systems and Methods for Medicament Delivery," filed Mar. 16, 2006, which is a national stage filing under 35 U.S.C. § 371 of International Patent Application No. PCT/US2006/003415, entitled "Devices, Systems and Methods for Medicament Delivery," filed Feb. 1, 2006, which claims priority to U.S. Provisional Application Ser. No. 60/648,822, entitled "Devices, Systems and Methods for Medicament Delivery," filed Feb. 1, 2005 and U.S. Provisional Application Ser. No. 60/731,886, entitled "Auto-Injector with Feedback," filed Oct. 31, 2005; each of which is incorporated herein by reference in its entirety. U.S. patent application Ser. No. 12/017,405 also claims priority to U.S. Provisional Application Ser. No. 60/885,969, entitled "Medicament Delivery Devices with Wireless Communication," filed Jan. 22, 2007, which is incorporated herein by reference in its entirety. U.S. patent application Ser. Nos. 11/671,025 and 11/621,236 each claim priority to U.S. Provisional Application Ser. No. 60/787,046, entitled "Devices, Systems and Methods for Medicament Delivery," filed Mar. 29, 2006, which is incorporated herein by reference in its entirety.

BACKGROUND

The invention relates generally to medical devices, and more particularly to medical systems, medicament delivery devices and methods for delivering a medicament into a body of a patient and outputting an electronic signal in response to such delivery.

Self-administered medicament delivery devices, such as, for example pre-filled medical injectors, inhalers, transdermal delivery devices and the like are often used as a part of a patient's medication regimen. For example, known self-administered medicament delivery devices can be used as a part of a patient's emergency care regimen. Emergency care regimens can include, for example, using an auto-injector to rapidly self-administer a medicament in response to an allergic reaction or for the treatment of other emergency conditions (e.g., nerve-agent poisoning on the battlefield). Known self-administered medicament delivery devices can also be used as a part of a patient's chronic care regimen. Chronic care regimens can include, for example, using a pen injector to self-administer a medicament according to a prescribed plan. Examples of chronic care regimens can include, for example, the injection of insulin, the injection of human growth hormone (HGH), erythropoiesis-stimulating agents (ESA), DeMab, Interferons and other chronic therapies, or the like. Furthermore, self-administered medicament delivery devices can also be used for preventive/prophylactic therapies. Examples of preventive/prophylactic therapies include certain vaccines, such as an influenza vaccine.

In the pharmaceutical industry, it can be important to understand patient compliance with self-administered medicament delivery devices. Patient compliance can include any measure of a patient's conformance to a particular therapeutic drug delivery regimen or other indication as mandated by a health care provider or pharmaceutical manufacturer. More particularly, patient compliance measures can include the location where the device was activated, time of day, dose regimen, dosage and route of administration, frequency of device usage, functionality of the device once used, expiration date of the device, device status, medicament status, and any adverse event experienced by the user following the use of the device. Patient compliance can also include providing communication to the patient regarding their therapy (e.g., a notification of when to take their medication, etc.). Understanding patient compliance with medicament delivery devices can enhance the ability of a health care provider to effectively manage a patient's medication regimen, which can lead to improved patient outcomes. Patient compliance data can also be used to inform the manufacturer of the device about potential issues with the device (e.g., data demonstrating poor compliance with a particular device may trigger a manufacturer to investigate the cause of poor compliance and/or change the design or functionality of the device to improve patient care and outcome), alert emergency contacts (including family members, patient guardians, and individuals with Power of Attorney privileges), and aid the patient with adhering to their prescribed therapy. Increasing patient compliance can also generate considerable cost savings for health care providers, pharmaceutical benefits managers (PBM), specialty pharmacies, clinical trial administrators, insurance companies and/or payors.

Ensuring patient compliance with some known medicament delivery devices can be problematic. For example, some known medicament delivery devices (e.g., emergency care devices, as described above and/or chronic care devices) can be bulky and conspicuous, which can make carrying them inconvenient and undesirable. Accordingly, the patient may not carry the medicament delivery device at all times, resulting in the failure to use the medicament delivery device as prescribed.

Similarly, to actuate some known medicament delivery devices, the user may be required to execute a series of operations. For example, to actuate some known auto-injectors, the user must remove a protective cap, remove a locking device, place the auto-injector in a proper position against the body and then press a button to actuate the auto-injector. Failure to complete these operations properly can result in an incomplete injection and/or injection into an undesired location of the body.

The likelihood of improper use of known medicament delivery devices can be compounded by the nature of the user and/or the circumstances under which such devices are used. For example, many users are not trained medical professionals and may have never been trained in the operation of such devices. Moreover, in certain situations, the user may not be the patient, and may therefore have no experience with the medicament delivery device. Similarly, because some known medicament delivery devices are configured to be used relatively infrequently in response to an allergic reaction or the like, even those users familiar with the device and/or who have been trained may not be well practiced at operating the device. Finally, such devices often can be used during an emergency situation, during which even experienced and/or trained users may be subject to confusion, panic and/or the physiological effects of the condition requiring treatment.

Monitoring the patient's compliance with known medicament delivery devices can also be problematic. For example, some known medicament delivery systems include a medicament delivery device and an electronic system to assist the user in setting the proper dosage and/or maintaining a compliance log. Such known medicament delivery systems and the accompanying electronic systems can be large and therefore not conveniently carried by the user. Such known medicament delivery systems and the accompanying electronic systems can also be complicated to use and/or expensive to manufacture.

Thus, a need exists for medicament delivery systems and/or devices that can provide compliance information associated with the use of the device. Moreover, a need exists for medicament delivery systems and/or devices that can communicate electronically with other communications devices.

SUMMARY

Medicament delivery systems and devices are described herein. In some embodiments, a system includes a medicament delivery device and a container configured to receive at least a portion of the medicament delivery device. The medicament delivery device includes an actuator and a first electronic circuit system. The actuator is configured to initiate delivery of a medicament into a body when the actuator is moved from a first position to a second position. The first electronic circuit system is configured to output a first electronic signal when the actuator is moved from the first position to the second position. The container includes a second electronic circuit system configured to receive the first electronic signal. The second electronic circuit system is configured to output a second electronic signal associated with the first electronic signal.

BRIEF DESCRIPTION OF THE DRAWINGS

FIGS. 29-31 are perspective views of a medical system according to an embodiment of the invention, in a first configuration, a second configuration, and a third configuration, respectively.

DETAILED DESCRIPTION

Figure 1:
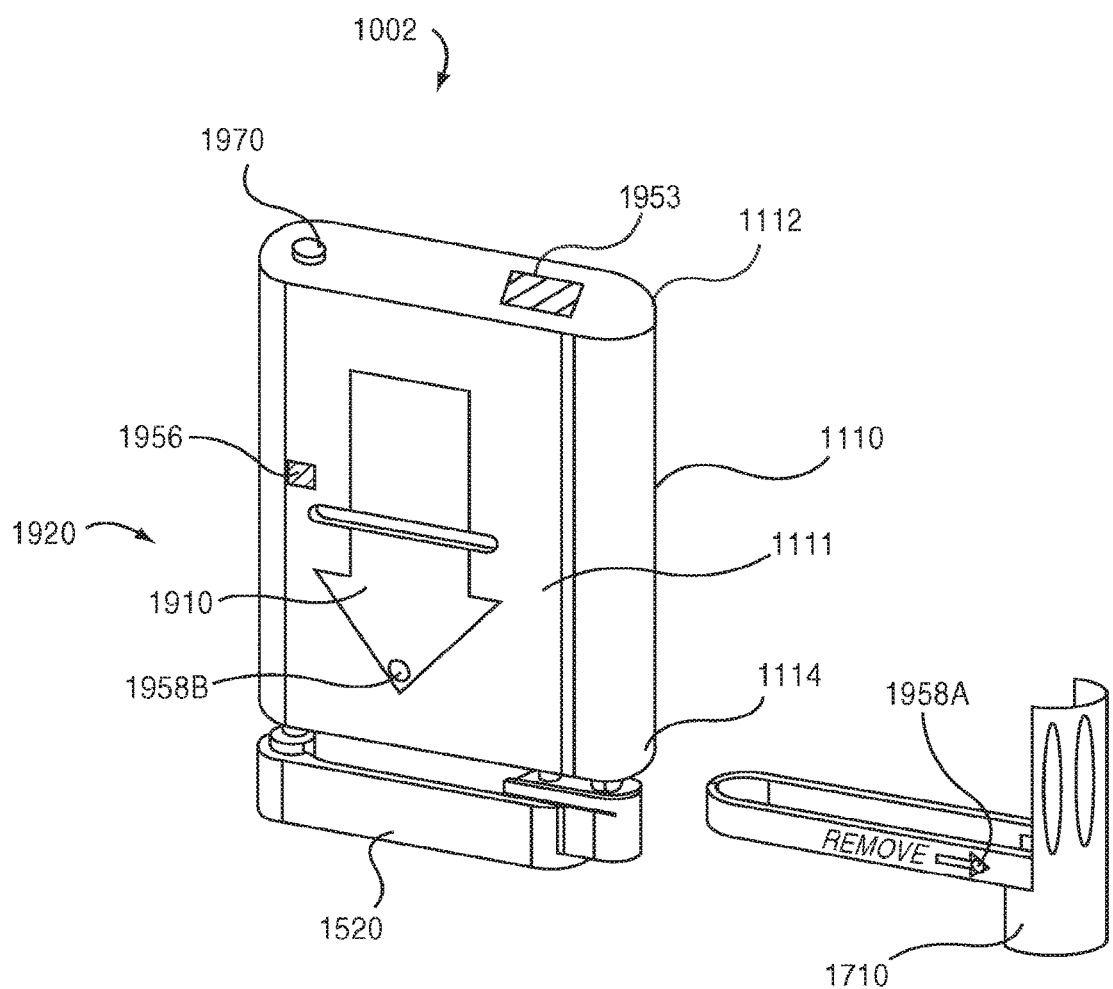
FIG. 1 is a perspective view of an auto-injector according to an embodiment of the invention.

In some embodiments, a system includes a medicament delivery device and a container configured to receive at least a portion of the medicament delivery device. The medicament delivery device, which can be, for example, a single-use medical injector, includes an actuator and a first electronic circuit system. The actuator is configured to initiate delivery of a medicament into a body when the actuator is moved from a first position to a second position. The first electronic circuit system is configured to output a first electronic signal when the actuator is moved from the first position to the second position. The first electronic signal can be, for example, a short-range radio frequency signal having a range of approximately 100 meters or less. The container includes a second electronic circuit system configured to receive the first electronic signal. The second electronic circuit system is configured to output a second electronic signal associated with the first electronic signal.

In some embodiments, an apparatus includes a medicament delivery device and an electronic circuit system coupled to the medicament delivery device. The medicament delivery device includes an actuator configured to initiate delivery of a medicament into a body when the actuator is moved from a first position to a second position. The electronic circuit system includes a first radio frequency identification tag configured to output a first electronic signal and a second radio frequency identification tag configured to output a second electronic signal. The second electronic signal has a characteristic (e.g., a frequency) different than a characteristic of the first electronic signal. The actuator is configured to prevent the second radio frequency identification tag from outputting the second electronic signal when the actuator is moved from the first position to the second position. In some embodiments, for example, the actuator is configured to sever at least a portion of the second radio frequency identification tag when the actuator is moved from the first position to the second position.

In some embodiments, an apparatus includes a housing, a medicament container disposed within the housing, a needle, and an electronic circuit system. The needle has a proximal end and a distal end, and is configured to be in fluid communication with the medicament container. The needle is configured to be moved between a first position and a second position. The distal end of the needle is disposed within the housing when the needle is in the first position. At least a portion of the distal end of the needle is disposed outside of the housing when the needle is in the second position. The electronic circuit system is configured to be coupled to the housing. The electronic circuit system is configured to output an electronic signal associated with an impedance between the distal end of the needle and a portion of the housing.

In some embodiments, a method includes moving an actuator of a medicament delivery device to initiate delivery of a medicament into a body. The actuator can be, for example, a mechanical actuator configured to release a spring, an energy storage member, or the like to initiate medicament delivery when the actuator is moved from the first position to the second position. A first electronic signal is output from a first electronic circuit system in response to the movement of the actuator between the first position and the second position. The first electronic signal is a short-range radio frequency signal having a range of approximately 100 meters or less. A second electronic signal associated with the first electronic signal is output from a second electronic circuit system.

As used herein, the term "regimen" or "medication regimen" can include any program, schedule and/or procedure to enhance, improve, sustain, alter, and/or maintain a patient's well-being. A regimen can include, for example, a schedule of medicament delivery events (e.g., injections, oral doses, etc.) that are prescribed or otherwise suggested for the patient. For example, a regimen can include daily insulin injections. A regimen can also include a single medicament delivery event that can be prescribed or otherwise suggested for the patient to administer in response to given a set of circumstances. For example, a regimen can include a injection of epinephrine in response to an allergic reaction. A regimen can also include the delivery of a placebo or inactive ingredient. For example, a clinical trial can include a regimen including various injections of a placebo. Finally, a regimen can also include activities other than the delivery of drugs to the patient. For example, a regimen can include certain procedures to be followed to enhance the patient's well-being (e.g., a schedule of rest, a dietary plan, etc.).

Figure 2:
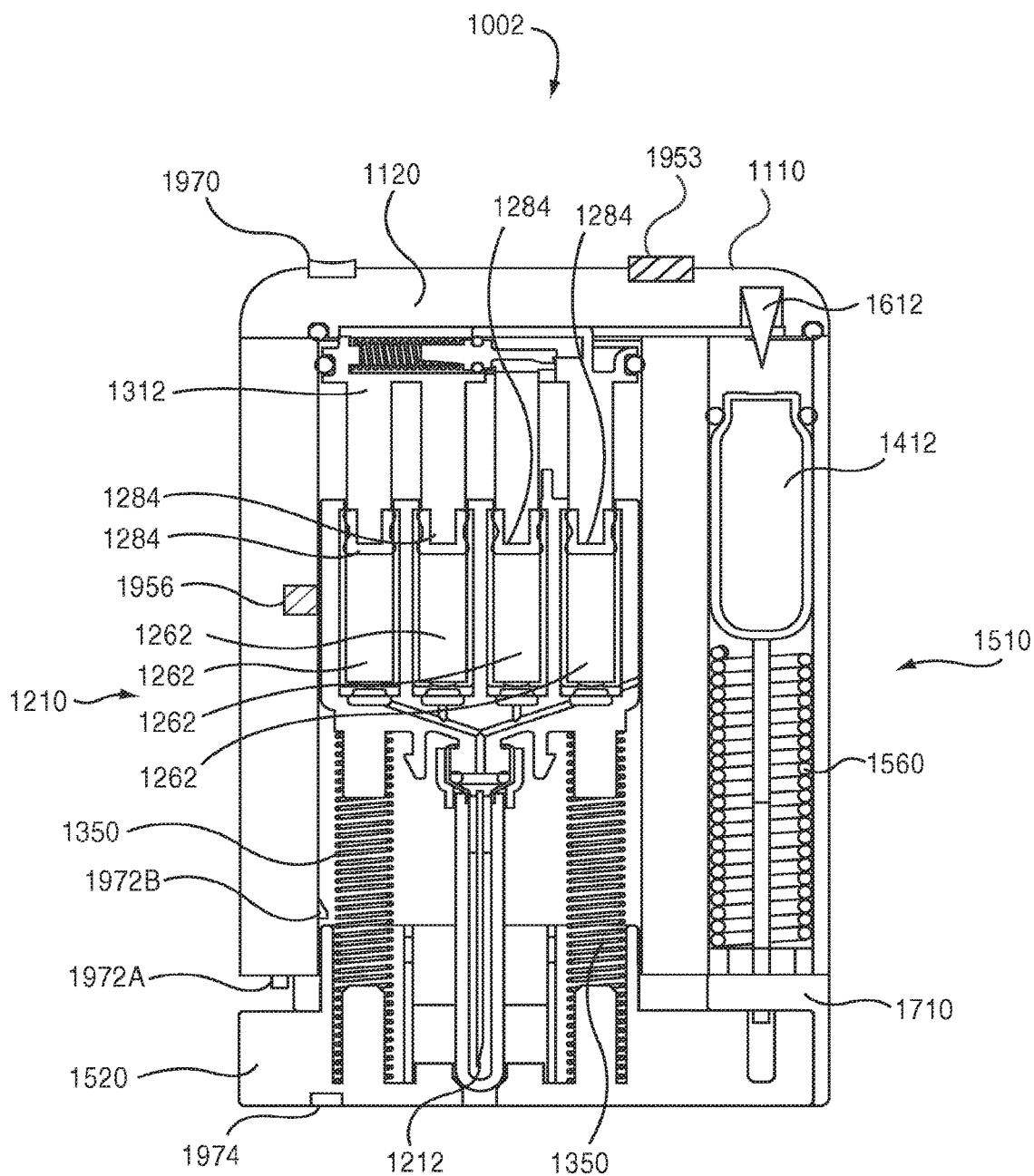
FIG. 2 is a front cross-sectional view of the auto-injector shown in FIG. 1.

FIGS. 1 and 2 are a perspective view and a partial cutaway front view, respectively, of an auto-injector 1002 according to an embodiment of the invention. The auto-injector 1002 is similar to the auto-injectors described in U.S. patent application Ser. No. 11/562,061, entitled "Devices, Systems and Methods for Medicament Delivery," filed Nov. 21, 2006, which is incorporated herein by reference in its entirety. Accordingly, only an overview of the mechanical components and related operation of the auto-injector 1002 is included below.

The auto-injector 1002 includes a housing 1110 that defines a gas chamber 1120. The housing 1110 has a proximal end portion 1112 and a distal end portion 1114. A base 1520 is movably coupled to the distal end portion 1114 of the housing 1110. A safety lock 1710 is removably coupled to the base 1520. As discussed in more detail herein, when the safety lock 1710 is coupled to the base 1520, the auto-injector 1002 cannot be actuated. When the safety lock 1710 is removed from the base 1520, the base 1520 can be moved relative to the housing 1110, thereby actuating the auto-injector 1002. Accordingly, to inject a medicament into the body, the distal end portion 1114 of the housing 1110 is oriented towards the user such that the base 1520 is in contact with the portion of the body where the injection is to be made. The base 1520 is then moved towards the proximal end 1112 of the housing 1110 to actuate the auto-injector 1002.

The auto-injector 1002 includes a medicament injector 1210 and a system actuator 1510 disposed non-coaxially within the housing 1110. The medicament injector 1210 includes multiple medicament vials 1262, a plunger 1284 movably disposed within each medicament vial 1262, a movable member 1312 engaged with each plunger 1284 and a needle 1212. Retraction springs 1350 located within a portion of the base 1520 and the housing 1110 can push the needle 1212 back within the housing 1110 after injection. The system actuator 1510 includes a compressed spring 1560, a compressed gas cylinder 1412, and a puncturing mechanism 1612 to dispel the contents of the compressed gas cylinder 1412.

In use, when the auto-injector 1002 is actuated, the puncturing mechanism 1612 punctures the compressed gas cylinder 1412 allowing a pressurized gas to flow into the gas chamber 1120. In response to a force produced by the pressurized gas on the movable member 1312, the movable member 1312 moves distally within the housing 1110. As a result, the needle 1212 is extended through the housing 1110. The movement of the movable member 1312 also causes the plungers 1284 to move within the vials 1262, thereby expelling a medicament from the vials 1262.

The auto-injector 1002 includes an electronic circuit system 1920 configured to provide a predetermined sequence of electronic outputs and/or electronic signals during the use of the auto-injector 1002. The electronic circuit system 1920 is powered by a battery (not shown in FIGS. 1 and 2) and includes a processor (see e.g., FIG. 3), a start button 1970, two switches 1972A and 1972B, a proximity sensor 1974, two visual output devices 1958A and 1958B, an audio output device 1956, and a network interface device 1953. The components of the electronic circuit system 1920 are operatively coupled by any suitable mechanism, such as, for example, a printed circuit board (not shown in FIGS. 1 and 2) having conductive traces.

The start button 1970 is disposed on the proximal end of the housing 1110 and can be manually actuated by the user to begin the sequence of electronic outputs. The first switch 1972A is disposed on the distal portion 1114 of the housing 1110 adjacent the base 1520 and the locking member 1710. The locking member 1710 is configured to engage the first switch 1972A such that when the locking member 1710 is removed, as shown in FIG. 1, the first switch 1972A changes states. In this manner, removal of the locking member 1710 can trigger the processor to output a predetermined electronic output. Said another way, the electronic circuit system 1920 can produce and/or output an electronic signal and/or an electronic output when the auto-injector 1002 is moved from a "storage" configuration (i.e., a configuration in which the locking member 1710 will prevent the actuation of the auto-injector 1002) to a "ready" configuration (i.e., a configuration in which the auto-injector 1002 can be actuated).

The proximity sensor 1974 is disposed on the base 1520 and is configured to produce an output when the base 1520 engages the body. The proximity sensor can be, for example, a temperature sensor, an optical sensor, pressure sensor, impedance sensor or the like. In this manner, the processor can be prompted to output a predetermined electronic output when the base 1520 is positioned against the body.

Similarly, the second switch 1972B is disposed on the housing 1110 adjacent the medicament injector 1210. The medicament injector 1210 is configured to engage the second switch 1972B such that when the medicament injector 1210 is moved distally within the housing 1110 the second switch 1972B changes states. In this manner, the processor can be prompted to output a predetermined electronic output based on the position of the medicament injector 1210. Said another way, the electronic circuit system 1920 can produce and/or output an electronic signal and/or an electronic output in response to the actuation of the auto-injector 1002.

In some embodiments, the electronic circuit system 1920 can be configured to output an electronic signal and/or an electronic output based on the output of the proximity sensor 1974 and the output from the second switch 1972B. For example, in some embodiments, the electronic circuit system 1920 can output a first electronic signal when the output from the proximity sensor 1974 indicates that the base 1520 of the auto-injector 1002 is in contact with the body when the second switch 1972B changes states, and a second electronic signal when the output from the proximity sensor 1974 indicates that the base 1520 of the auto-injector 1002 is disposed apart from the body when the second switch 1972B changes states. Said another way, in some embodiments, the electronic circuit system 1920 can be configured to output a first electronic signal associated with the occurrence of a valid injection event (i.e., an injection event during which there was a high likelihood that the medicament was properly injected into the body) and a second electronic signal associated with the occurrence of an invalid injection event (i.e., an injection event during which there was a high likelihood that the medicament was not injected into the body).

The first visual output device 1958A is disposed on the locking member 1710. Similarly, the second visual output device 1958B is disposed on the outer surface 1111 of the housing 1110. The visual output devices 1958A and 1958B are in electronic communication with the processor and are configured to produce an output in response to an electronic signal output by the processor. The visual output devices 1958A and 1958B, as well as any other visual output devices referenced herein, can be any suitable visual indicia, such as, light-emitting diodes (LEDs), liquid-crystal display (LCD) screens, optical polymers, fiber optic components or the like. In some embodiments, the visual output devices 1958A and 1958B can be coupled to the housing 1110 and/or the locking member 1710 by a label 1910.

The audio output device 1956 is disposed within the housing 1110 such that it can project sound outside of the housing 1110. The audio output device 1956, as well as any other audio output devices referenced herein, can be any suitable device for producing sound, such as a micro-speaker a piezo-electric transducer or the like. Such sound output can include, for example, an alarm, a series of beeps, recorded speech or the like. The audio output device 1956 is in electronic communication with the processor and is configured to produce an output in response to an electronic signal output by the processor.

Figure 3:
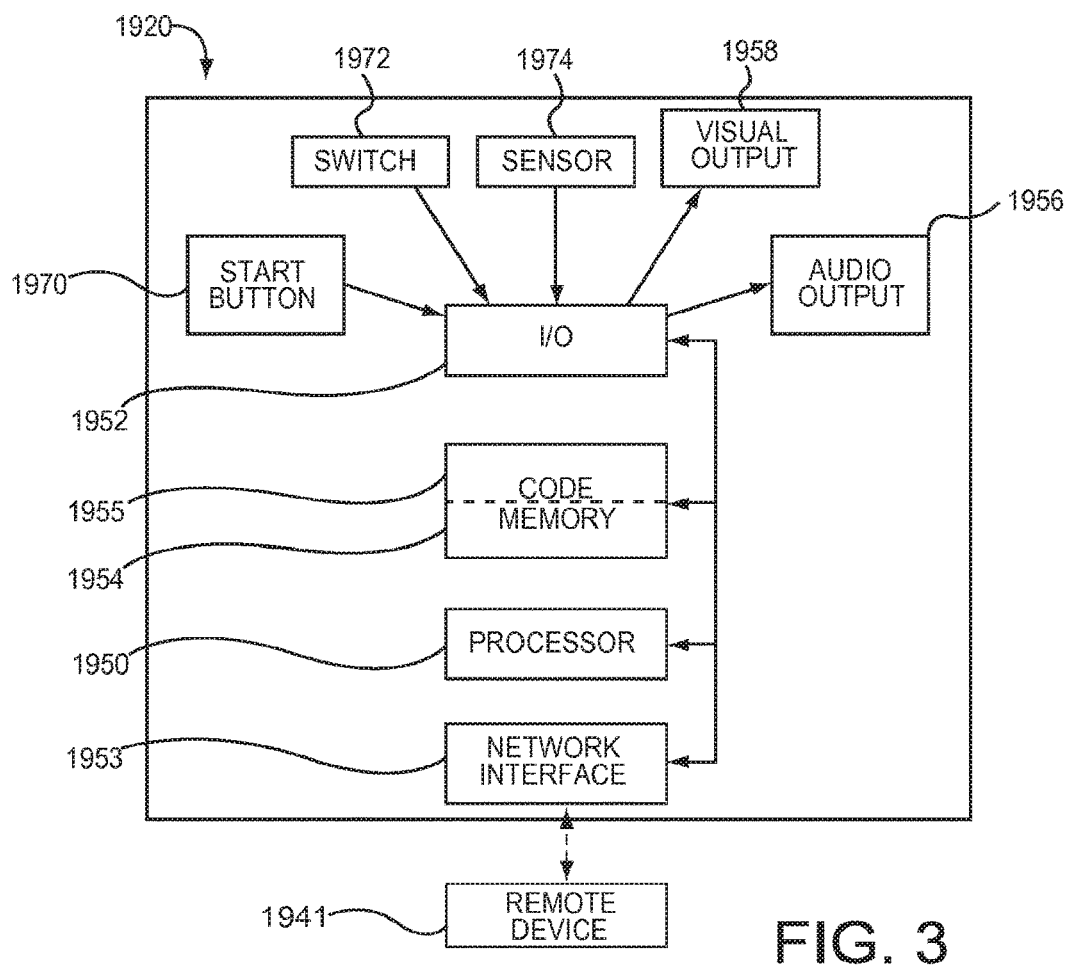
FIG. 3 is a schematic illustration of a portion of the auto-injector shown in FIG. 1.

The network interface device 1953 is configured to operatively connect the electronic circuit system 1920 to a remote device 1941 (see FIG. 3) and/or a communications network (not shown in FIGS. 1-3). In this manner, the electronic circuit system 1920 can send information to and/or receive information from the remote device 1941. The remote device 1941 can be, for example, a remote communications network, a computer, a compliance monitoring device, a cell phone, a personal digital assistant (PDA) or the like. Such an arrangement can be used, for example, to download replacement processor-readable code 1955 (see FIG. 3) from a central network to the memory device 1954 (see FIG. 3). In some embodiments, for example, the electronic circuit system 1920 can download information associated with a medicament delivery device 1002, such as an expiration date, a recall notice, updated use instructions or the like. Similarly, in some embodiments, the electronic circuit system 1920 can upload compliance information associated with the use of the medicament delivery device 1002 via the network interface device 1953.

In use, the user activates the electronic circuit system by pushing the start button 1970 to activate the processor, thereby causing the processor to output a predetermined sequence of electronic outputs. In some embodiments, the start button 1970 can activate the processor by providing an input to the processor. In other embodiments, the start button 1970 can activate the processor by placing the battery (not shown in FIGS. 1 and 2) in electronic communication with the processor.

In some embodiments, upon activation, the processor can output an electronic signal to the audio output device 1956 thereby producing a first electronic output instructing the user in how to use the auto-injector 1002. Such a message can state, for example, "please remove the safety tab." Additionally, the first visual output device 1958A can produce a flashing light to further indicate to the user where the locking member 1710 is located. The processor can be configured to repeat the first audible instruction if the locking member 1710 is not removed within a predetermined time period.

When the user removes the locking member 1710, the first switch 1972A changes states thereby triggering the processor to output an electronic output providing a second instruction to the user. The second instruction can be, for example, an audible speech output instructing the user to "please place the base of the device on the outer portion of your thigh." The first visual output device 1958A can produce a lighted output during this audible instruction, thereby visually indicating where the base 1520 is located and/or what portion of the base 1520 should be placed on the thigh.

When the user places the base 1520 against the body, the proximity sensor 1974 provides an input to the processor, thereby triggering the processor to output an electronic output providing a third instruction to the user. The third instruction can be, for example, an audible speech output instructing the user to "push down on the top of the device to activate the injector."

When the injection is completed, the medicament injector 1210 is configured to engage the second switch 1972B, thereby triggering the processor to output an electronic output providing a fourth instruction to the user. Such a post-use instruction can be, for example, an audible speech output instructing the user to seek further medical attention, providing instructions for the safe disposal of the auto-injector 1002 or the like.

In some embodiments, the processor 1950 can output an electrical signal associated with the second switch 1972B that is received by a remote device 1941, which can be, for example, a compliance tracking device. Said another way, in some embodiments, the electronic circuit system 1920 can output, to the remote device 1941, an electrical signal associated with the end of the injection event. In this manner the electronic circuit system 1920 on the auto-injector 1002 can cooperate with the remote device 1941 to electronically and/or automatically track the details of the use of the auto-injector 1002. Similarly stated, the electronic circuit system 1920 on the auto-injector 1002 and the remote device 1941 can electronically and/or automatically track the patient compliance data associated with the use of the auto-injector 1002.

FIG. 3 is a schematic illustration of the electronic circuit system 1920 of the auto-injector 1002. The electronic circuit system 1920 includes a processor 1950 operatively coupled to a memory device 1954. The memory device 1954 can be configured to store processor-readable code 1955 instructing the processor 1950 to perform the functions described above. In some embodiments, the processor-readable code 1955 can be modified and/or updated as circumstances dictate. The electronic circuit system 1920 includes an input/output device 1952 configured to receive electronic inputs from the switches 1972A and 1972B, the proximity sensor 1974 and/or the start button 1970. The input/output device 1952 is also configured to provide electronic signals to the various output devices, such as the visual output devices 1958A and 1958B and the audio output device 1956.

As described above, the electronic circuit system 1920 also includes a network interface 1953 configured to couple the electronic circuit system 1920 to a remote device 1941 and/or a communications network (not shown in FIG. 3). Such an arrangement can be used, for example, to download replacement processor-readable code 1955 from a central network (not shown) to the memory device 1954. The network interface 1953 can also be configured to transmit information from the electronic circuit system 1920 to a central network and/or the remote device 1941 (e.g., the user's home computer, the user's cell phone or the like). The network interface 1953 can include any hardware, software and/or firmware suitable for establishing communication between the electronic circuit system 1920 and the remote device 1941. For example, in some embodiments, the network interface 1953 can include a microprocessor, a transmitter, a receiver, a transceiver, a microchip, a radio chipset, a wireless interface card (WIC), a host controller interface (HCI), a universal asynchronous receiver/transmitter (UART), a power source (e.g., a battery), one or more sensors, a transponder, an antenna, a crystal, a circuit board, a liquid crystal display (LCD), a Small Computer System Interface (SCSI and ports), a FireWire (or other IEEE 1394 interfaces), a data uplink, a data downlink, a point-to-point link, a fiber optic link, a storage device (e.g., hard drive, flash drive or the like), a personal computer cards, a docking stations, a parallel and/or bit-serial connections, a Universal Serial Bus (USB) port or other serial ports, radiofrequency identification (RFID) devices and/or other common electronic components used to establish electronic communication.

Figure 4:
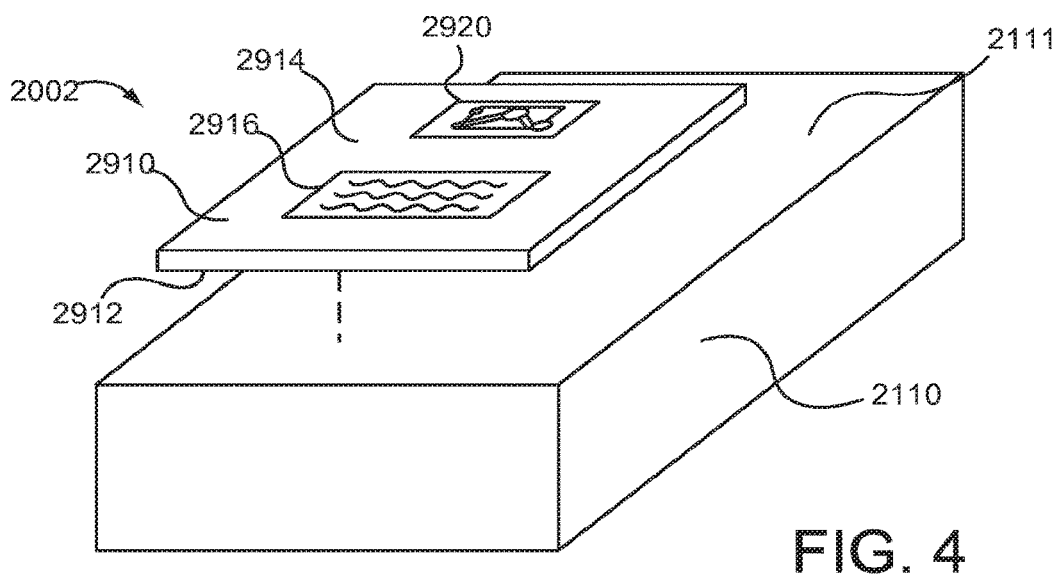
FIG. 4 is a schematic illustration of a medicament delivery device according to an embodiment of the invention.

FIG. 4 is a schematic illustration of a medical device 2002 according to an embodiment of the invention. The medical device 2002, which can be, for example, a medicament delivery device such as an auto-injector, a pen injector, an inhaler, a transdermal delivery system or the like, includes a housing 2110 and a label 2910. The label 2910 is coupled to an outer surface 2111 of the housing 2110. The label 2910 includes a first surface 2912, a second surface 2914 and an electronic circuit system 2920. The first surface 2912 is configured to engage the outer surface 2111 of the housing 2110 to couple the label 2910 to the housing 2110. In some embodiments, the first surface 2912 can include an adhesive to fixedly couple the label 2910 to the housing 2110. The second surface 2914 includes a textual indicia 2916. The textual indicia 2916 can include, for example, a description of the medicament delivery device, a source of the medicament delivery device and/or an instruction associated with the use of the medicament delivery device. Although the first surface 2912 is shown as being opposite the second surface 2914, in other embodiments, the first surface 2912 and the second surface 2914 can be adjacent each other and/or co-planar.

The electronic circuit system 2920 is configured to output an electronic signal of the types shown and described herein. As discussed in more detail herein, the electronic circuit system 2920 can include many components, such as, for example, a processor, a switch, a visual output device and/or an audio output device. The electronic signal can be, for example, an electronic signal communicated to an output device, such as, for example, a visual output device, an audio output device, a haptic output device or the like. In some embodiments, the electrical signal can be a communications signal configured to be received by a remote device, in a manner similar to that described herein.

In some embodiments, the electronic signal can be associated with an aspect of the medical device 2002, such as an instruction associated with an initial use of the medical device 2002. For example, in some embodiments, the electronic circuit system 2920 can output a text message to a display screen (not shown) disposed on the medical device 2002 instructing the user in the use of the medical device 2002. In other embodiments, the electronic circuit system 2920 can produce an audio output, such as recorded speech, instructing the user in the use of the medical device 2002. In yet other embodiments, the electronic circuit system 2920 can produce and/or transmit an electrical signal associated with a medicament delivery event. In this manner, the electronic circuit system 2920 can be used to track the patient compliance data associated with the use of the medicament delivery device 2002.

Although the electronic circuit system 2920 is shown as being disposed on the second surface 2914 of the label 2910, in other embodiments, the electronic circuit system can be disposed on the first surface 2912 of the label 2910. In yet other embodiments, the electronic circuit system 2920 can be disposed between the first surface 2912 and the second surface 2914 of the label 2910. In yet other embodiments, the label 2910 can include multiple discrete layers coupled together, within which portions of the electronic circuit system can be disposed.

Figure 5:
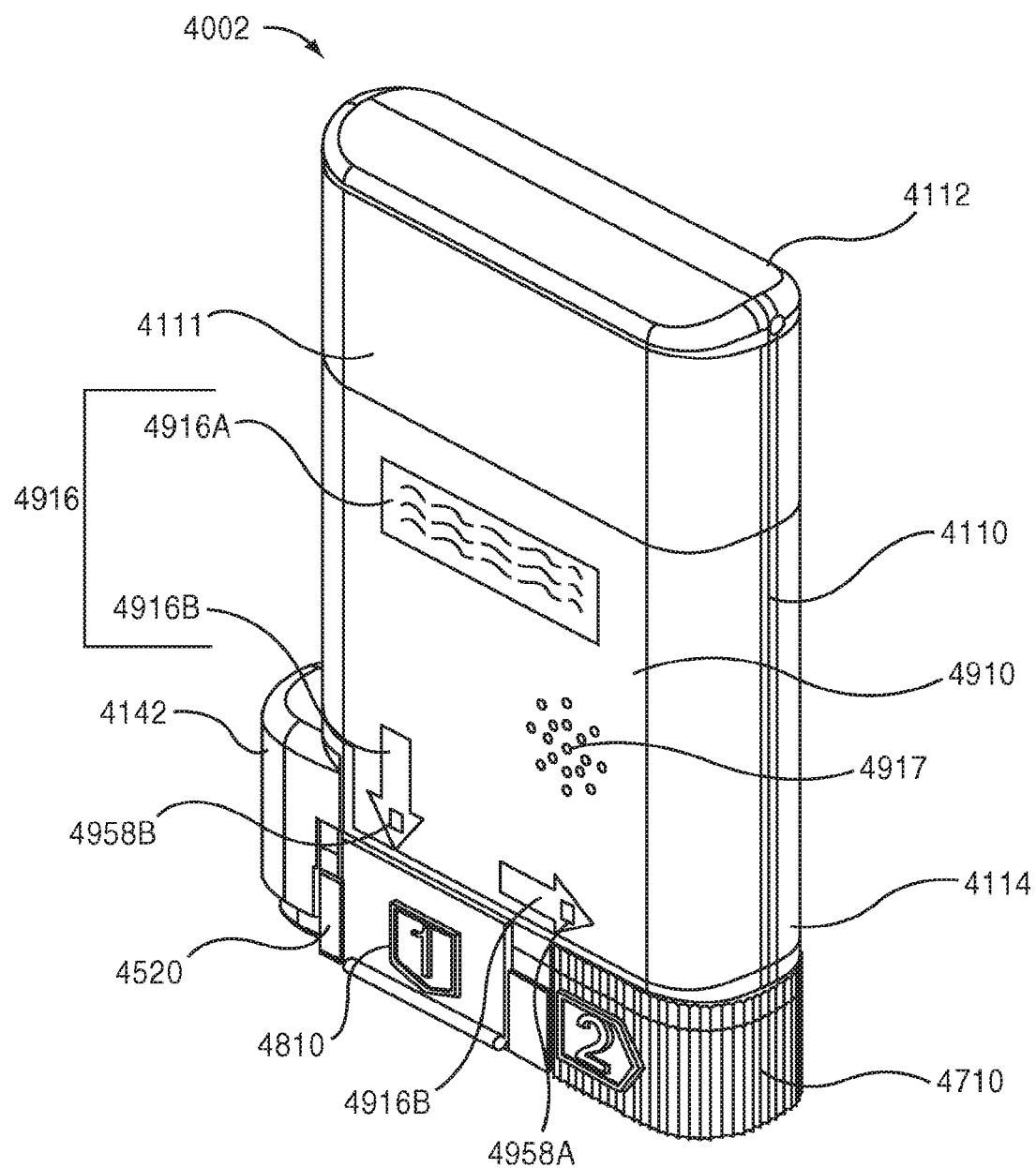
FIG. 5 is a perspective view of an auto-injector according to an embodiment of the invention.

FIG. 5 is a perspective view of an auto-injector 4002 according to an embodiment of the invention. The auto-injector 4002 is similar to the auto-injectors described in U.S. patent application Ser. No. 11/562,061, entitled "Devices, Systems and Methods for Medicament Delivery," filed Nov. 21, 2006, which is incorporated herein by reference in its entirety. Accordingly, the mechanical components and operation of the auto-injector 4002 are not described in detail herein.

The auto-injector 4002 includes a housing 4110 having a proximal end portion 4112 and a distal end portion 4114. The distal end portion 4114 of the housing 4110 includes a protrusion 4142 to help a user grasp and retain the housing 4110 when using the auto-injector 4002. Said another way, the protrusion 4142 is configured to prevent the auto-injector 4002 from slipping from the user's grasp during use. A base 4520 is movably coupled to the distal end portion 4114 of the housing 4110. A needle guard assembly 4810 is removably coupled to the base 4520. Similarly, a safety lock 4710 is removably coupled to the base 4520. To inject a medicament into the body, the distal end portion 4114 of the housing is oriented towards the user such that the base 4520 is in contact with the portion of the body where the injection is to be made. The base 4520 is then moved towards the proximal end 4112 of the housing 4110 to actuate the auto-injector 4002.

Figure 6:
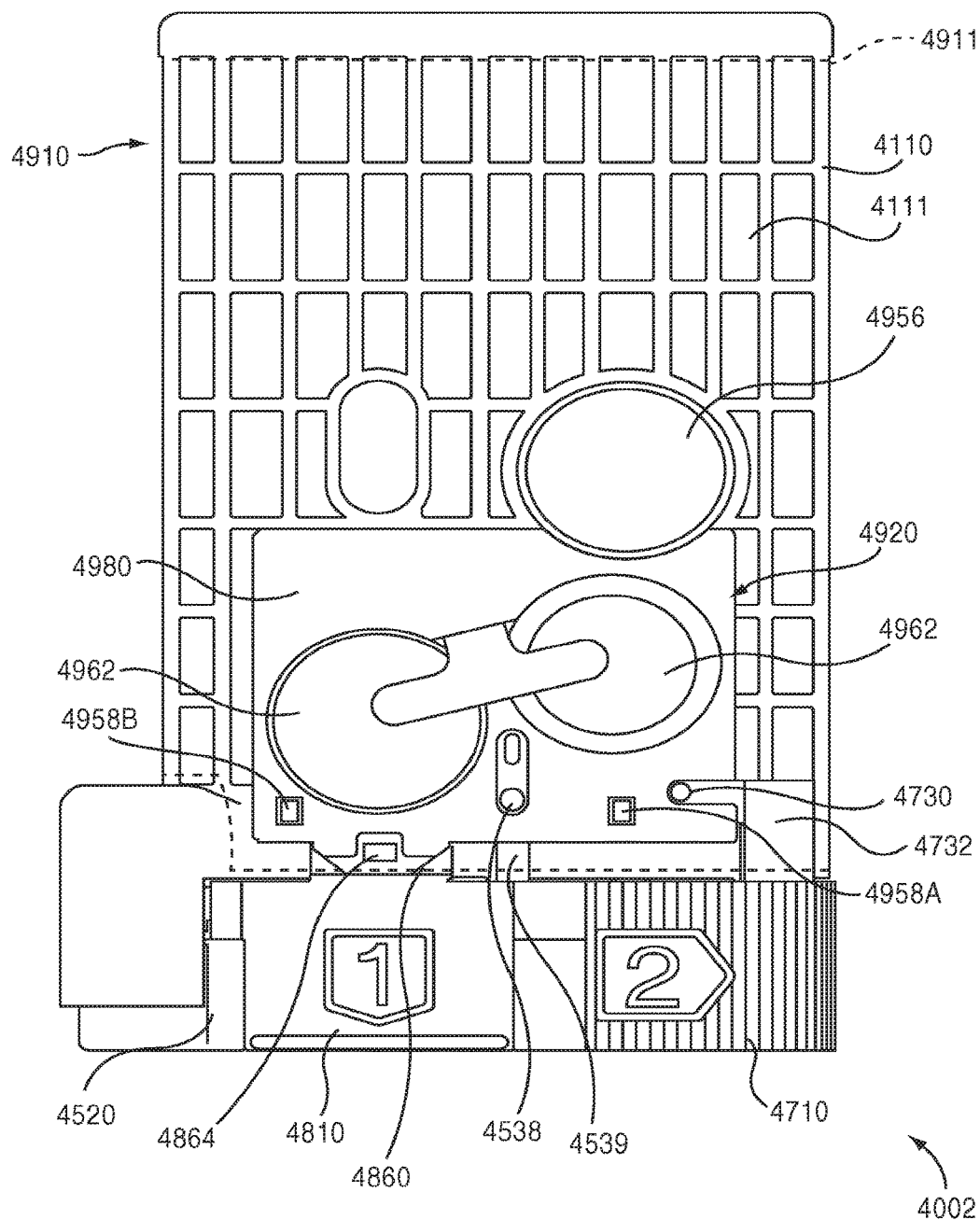
FIG. 6 is a front view of the auto-injector illustrated in FIG. 5, with a portion of the auto-injector illustrated in phantom lines for ease of reference.
Figure 7:
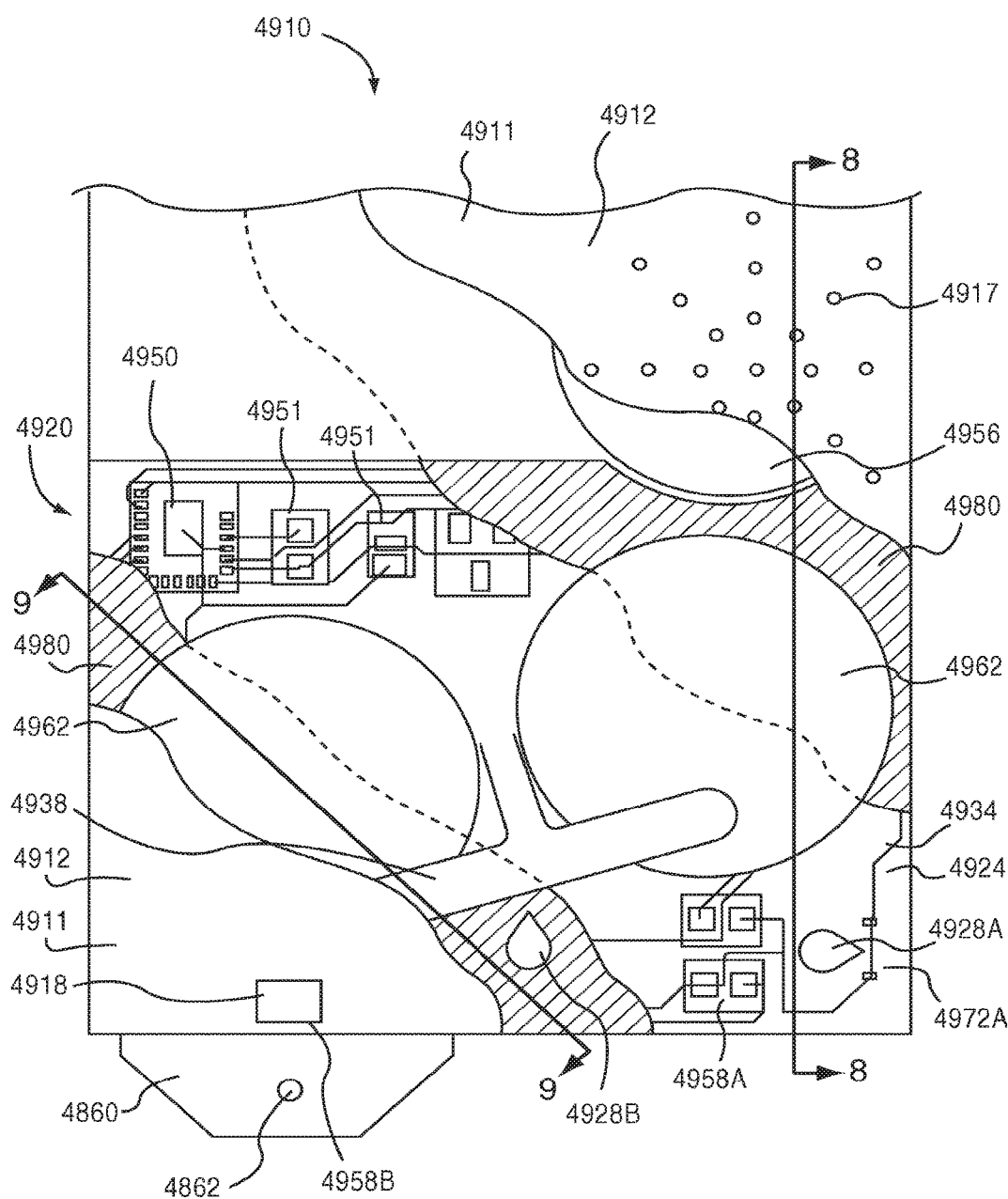
FIG. 7 is a partial cut-away front view of a portion of the auto-injector illustrated in FIG. 5.
Figure 8:
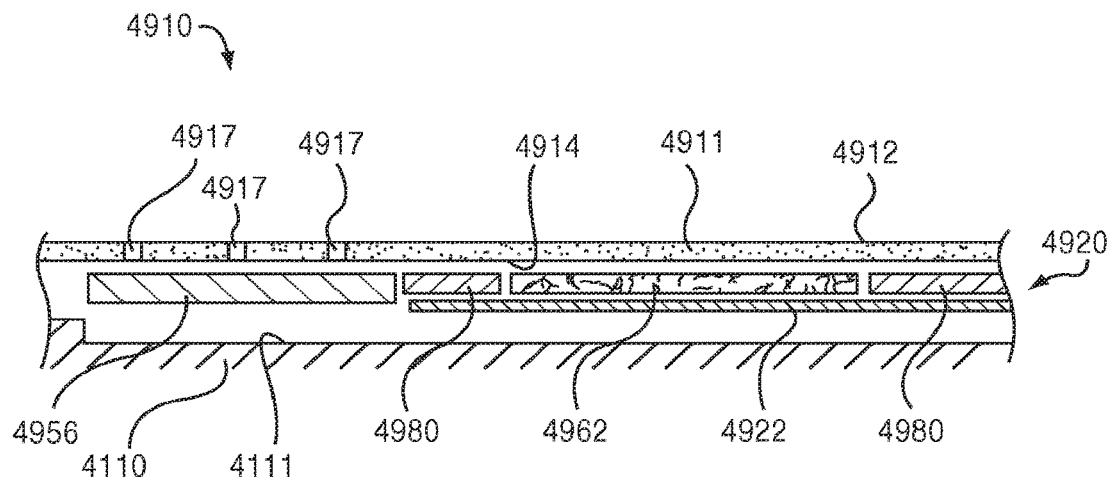
FIG. 8 is a cross-sectional view of a portion of the auto-injector illustrated in FIG. 5 taken along line 8-8 in FIG. 7.
Figure 9:
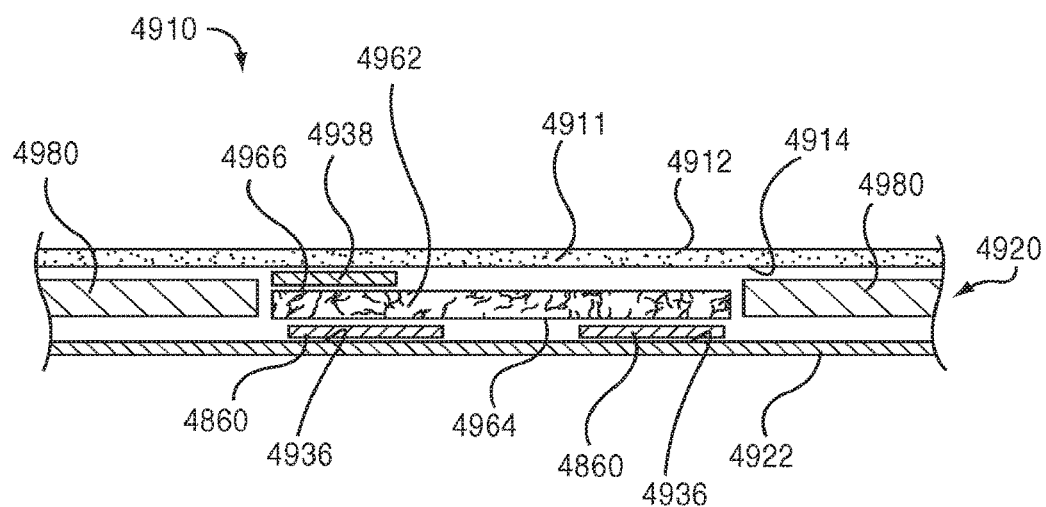
FIG. 9 is a cross-sectional view of a portion of the auto-injector illustrated in FIG. 5 taken along line 9-9 in FIG. 7.

The auto-injector 4002 includes a label 4910 coupled to an outer surface 4111 of the housing 4110. The label 4910 includes an outer layer 4911, an intermediate layer 4980 and an electronic circuit system 4920 (see FIGS. 7-9). FIG. 6 is a front view of the auto-injector 4002 showing the outer layer 4911 of the label 4910 in phantom lines so that the intermediate layer 4980 and an electronic circuit system 4920 can be more clearly seen. As shown in FIGS. 7-9, the outer layer 4911, which, in some embodiments, can be constructed from paper, has a first surface 4912 and a second surface 4914 opposite the first surface 4912. Multiple indicia 4916 are disposed on the first surface 4912. The indicia 4916 include a textual indicia 4916A and two symbolic indicia 4916B. The textual indicia 4916B can be written text describing the medicament delivery device, indicating a source of the medicament delivery device and/or instructing a user in the use of the medicament delivery device. The symbolic indicia 4916B can include, for example, arrows, pointers, trademarks, symbols describing the use of the medicament delivery device or the like. The label 4910 is coupled to the outer surface 4111 of the housing 4110 such that the portion of the first surface 4912 including the indicia 4916 is visible.

A portion of the second surface 4914 of the outer layer 4911 can be coupled to the outer surface 4111 of the housing 4110 by any suitable method. For example, in some embodiments, the second surface 4914 of the outer layer 4911 includes an adhesive configured to bond the outer layer 4911 to the outer surface 4111 of the housing 4110. Other portions of the second surface 4914 of the outer layer 4911 are adjacent the intermediate layer 4980 and portions of the electronic circuit system 4920. In this manner, the outer layer 4911 of the label 4910 retains the intermediate, or spacer, layer 4980 and the electronic circuit system 4920 in a predetermined position against the outer surface 4111 of the housing 4110.

The outer layer 4911 of the label 4910 includes multiple openings 4917 adjacent the audio output device 4956. In this manner, sound waves produced by the audio output device 4956 can be transmitted to an area outside of the housing 4110. Similarly, the outer layer 4911 of the label 4910 includes openings 4918 adjacent the light emitting diodes (LEDs) 4958A and 4958B to allow the user to see the visual output. In some embodiments, the outer layer 4911 of the label 4910 can include a transparent portion adjacent the LEDs 4958A and 4958B to allow the user to see the visual output.

The electronic circuit system 4920 includes a printed circuit board 4922 upon which a microprocessor 4950, two LEDs 4958A and 4958B, two switches 4972A and 4972B and various electronic components 4951, such as, for example, resistors, capacitors and diodes, are mounted. The electronic circuit system 4920 also includes an audio output device 4956, such as, for example, a micro-speaker, coupled to the outer surface 4111 of the housing 4110 adjacent the printed circuit board 4922. The printed circuit board 4922 includes a substrate 4924 upon which a series of electrical conductors 4934, such as for example, copper traces, are etched. The substrate 4924 can be constructed from any material having suitable electrical properties, mechanical properties and flexibility, such as, for example Mylar®, Kapton® or impregnated paper.

A mask layer (not shown) is disposed over the substrate 4924 to electrically isolate selected portions of the electrical conductors 4934 from adjacent components. The electrical conductors 4934 operatively couple the above-mentioned circuit components in a predetermined arrangement. In this manner, the electronic circuit system 4920 can be configured to output, via the LEDs 4958A and 4958B and/or the audio output device 4956, a predetermined sequence of electronic outputs during the use of the auto-injector 4002.

Power is supplied to the electronic circuit system 4920 by two batteries 4962 connected in series. The batteries can be, for example, three volt, "watch-style" lithium batteries. As shown in FIG. 9, each of the batteries 4962 has a first surface 4964 and a second surface 4966 opposite the first surface. The first surface 4964 can be, for example, an electrically negative terminal. Similarly, the second surface 4966 can be an electrically positive terminal. As discussed in more detail herein, the batteries 4962 are positioned such that a first electrical contact portion 4936 of the printed circuit board 4922 can be placed in contact with the first surface 4964 of the battery 4962 and a second electrical contact portion 4938 of the printed circuit board 4922 can be placed in contact with the second surface 4966 of the battery 4962. In this manner, the batteries 4962 can be operatively coupled to the electronic circuit system 4920.

As shown in FIGS. 7 and 9, a battery isolation tab 4860 is movably disposed between the first electrical contact portion 4936 of the printed circuit board 4922 and the first surface 4964 of one of the batteries 4962. The battery isolation tab 4860 can be constructed from any electrically isolative material, such as, for example, Mylar®. As discussed in more detail herein, in this manner, the batteries 4962 can be selectively placed in electronic communication with the electronic circuit system 4920.

The intermediate, or spacer, layer 4980 is disposed between the outer layer 4911 and the electronic circuit system 4920. The intermediate layer 4980 includes openings (not shown) within which various components of the electronic circuit system, such as, for example, the batteries 4962 are disposed. The intermediate layer 4980 is sized to maintain a predetermined spacing between the various components included in the label 4910. The intermediate layer can be constructed from any suitable material, such as, for example, flexible foam having an adhesive surface, polycarbonate or the like.

Figure 10:
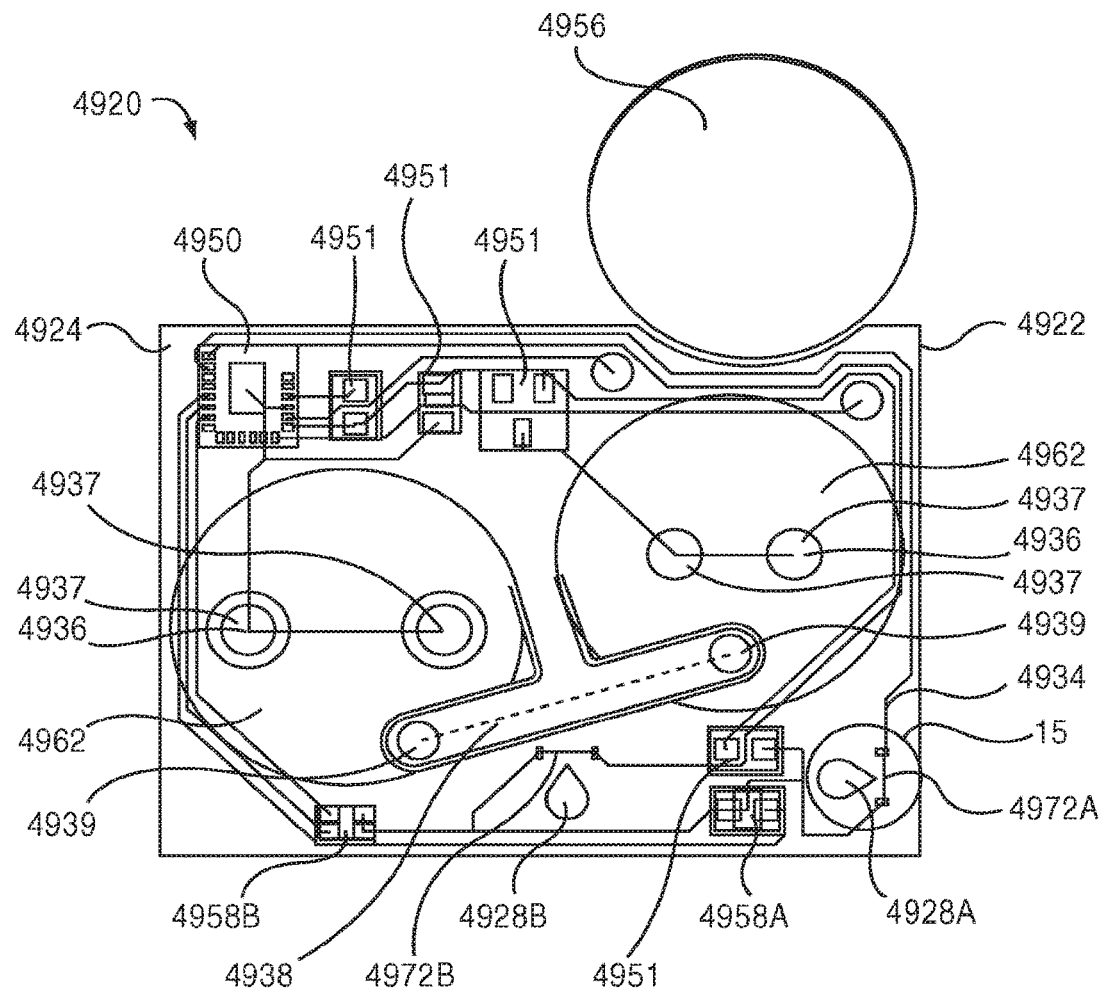
FIG. 10 is a front view of a portion of the auto-injector illustrated in FIG. 5.
Figure 11:
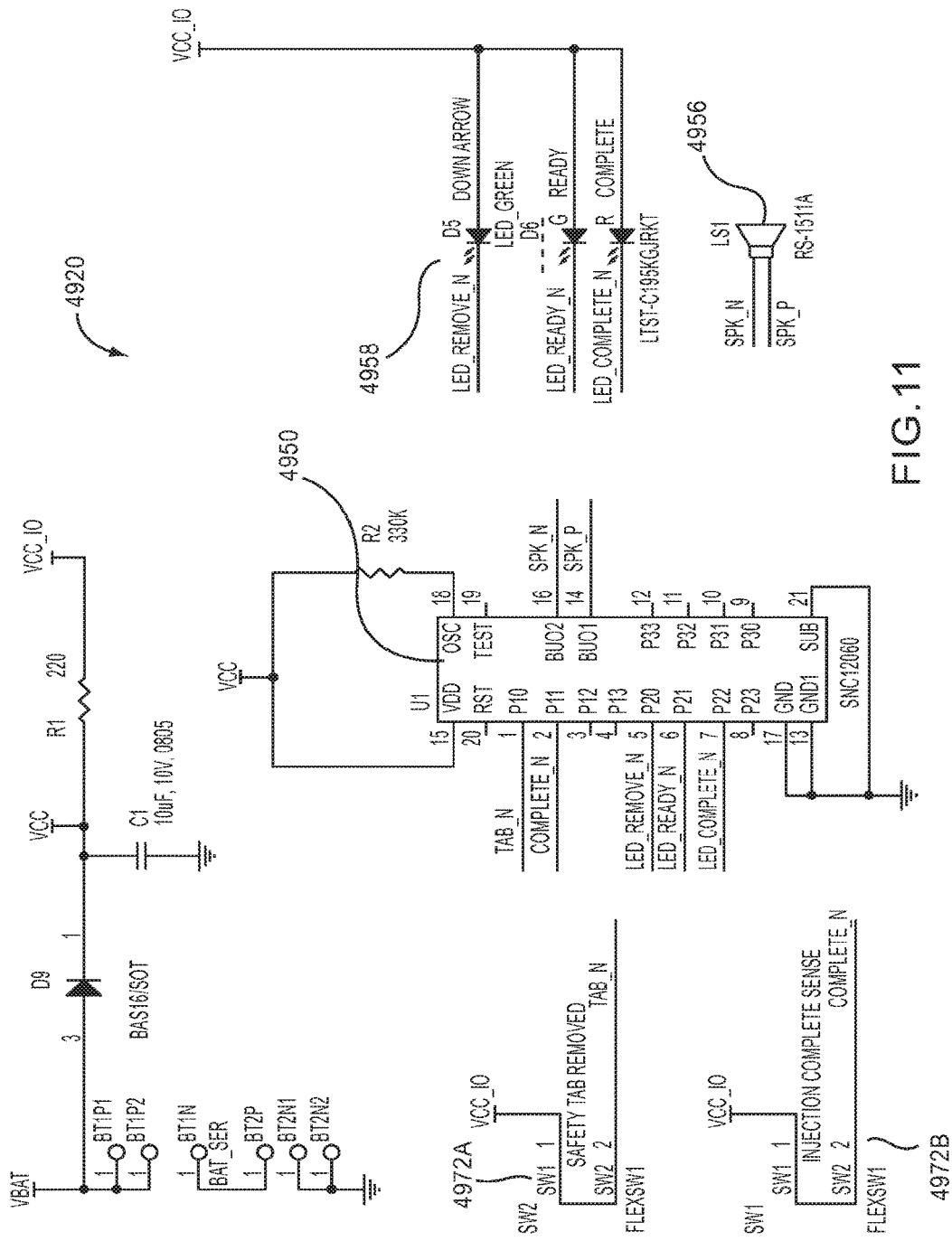
FIG. 11 is a schematic illustration of a portion of the auto-injector illustrated in FIG. 5.

FIG. 10 is a front view of the electronic circuit system 4920 showing the arrangement of the various components (i.e., the microprocessor 4950, LEDs 4958A and 4958B, switches 4972A and 4972B, audio output device 4956 or the like). FIG. 11 is a schematic illustration of the electronic circuit system 4920.

The operation of the auto-injector 4002 and the electronic circuit system 4920 is now discussed with reference to FIGS. 12-14. The actuation of the electronic circuit system 4920 is performed in multiple steps that correspond to operations that are incorporated into the procedures for using the auto-injector 4002. In this manner, the user can actuate various portions and/or functions of the electronic circuit system 4920 without completing any additional operations. Similarly stated, the electronic circuit system 4920 can produce and/or transmit electronic outputs in response to the various stages of operation of the auto-injector 4002. Although not explicitly shown in FIGS. 5-14, in some embodiments, the electronic circuit system 4920 can include a network interface device, as described herein. In this manner, the electronic outputs produced and/or transmitted by the electronic circuit system 4920 can be used to track the patient compliance associated with the use of the auto-injector 4002.

Figure 12:
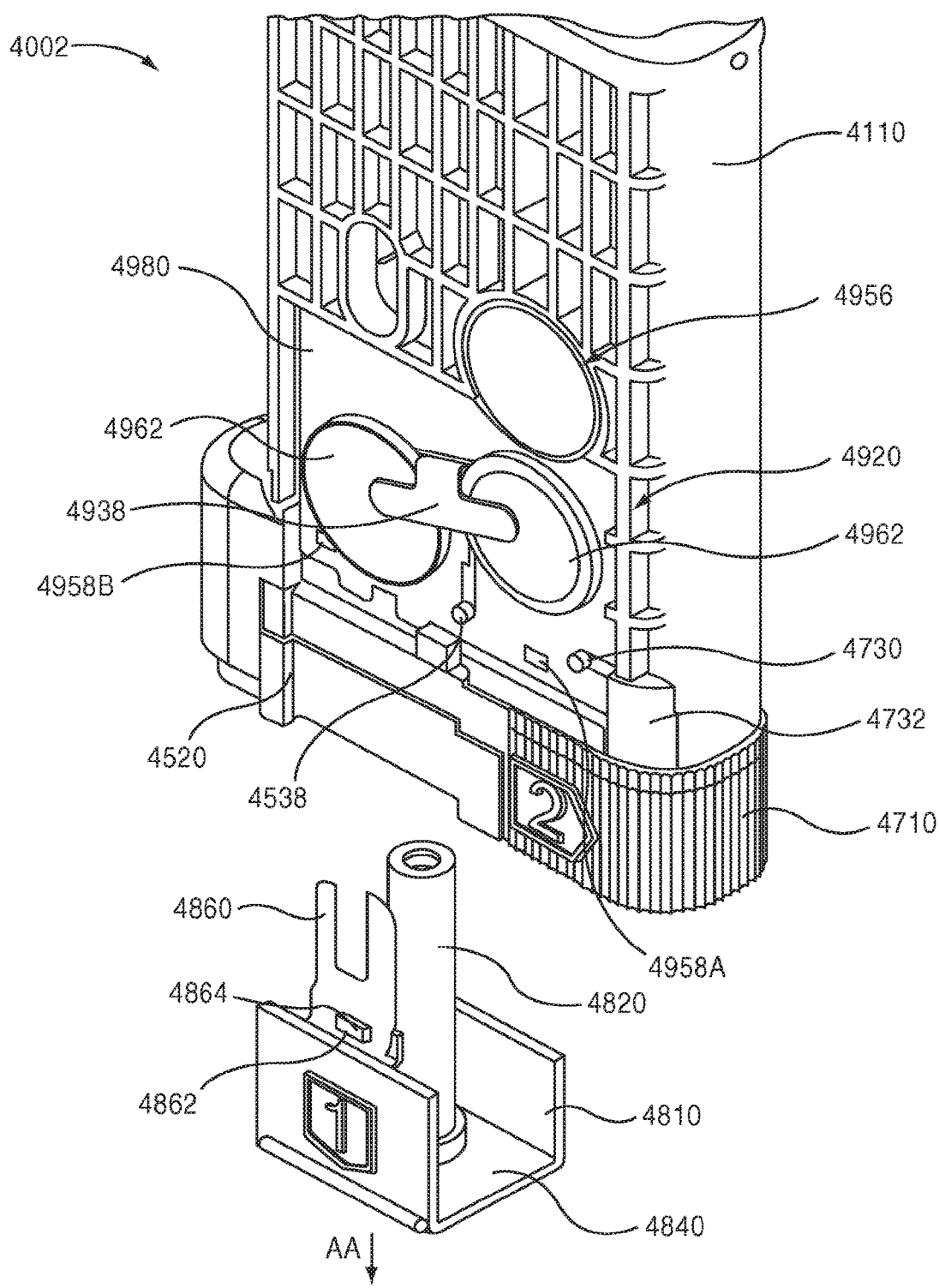
FIG. 12 is a perspective view of a portion of the auto-injector illustrated in FIG. 5 in a second configuration.
Figure 13:
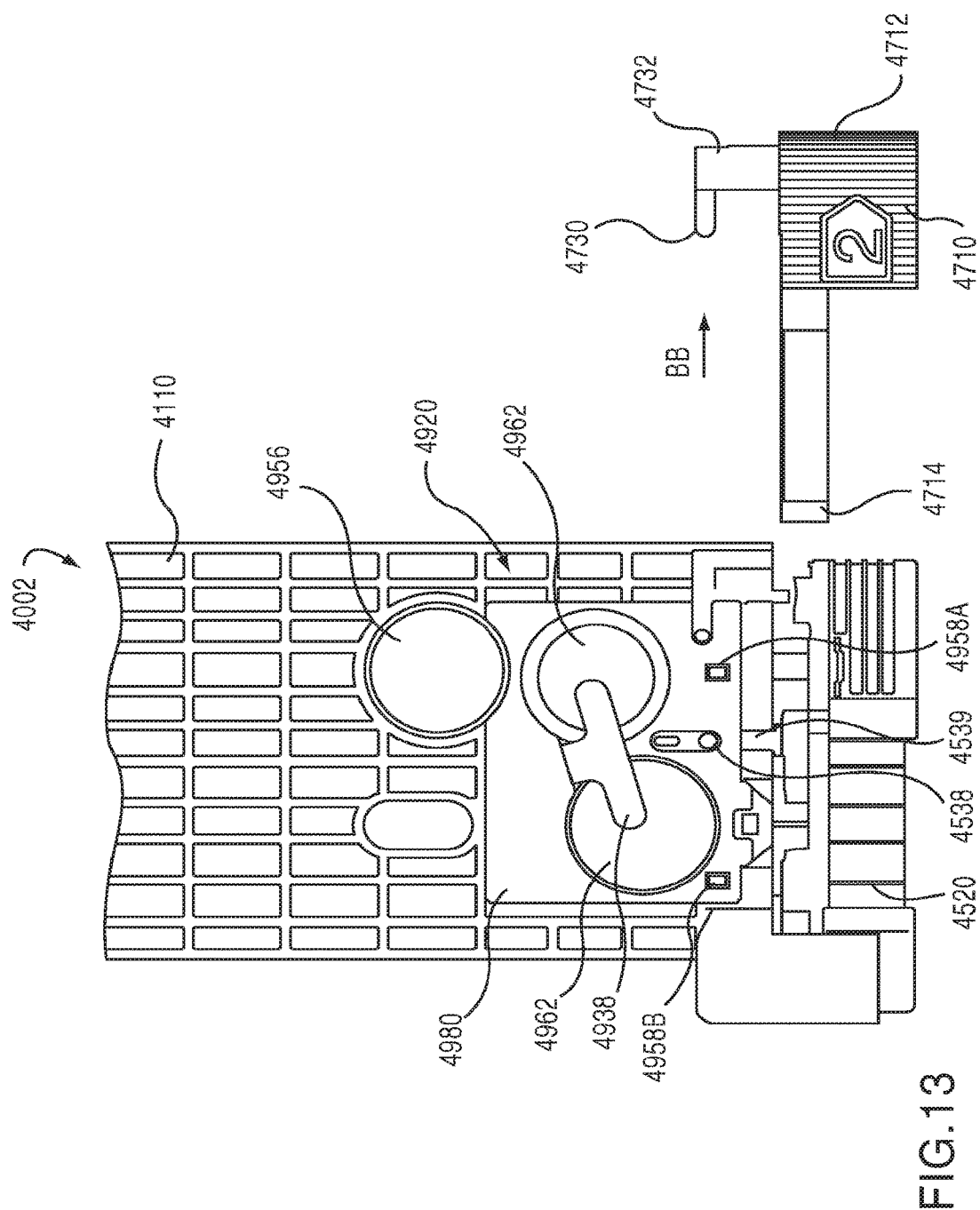
FIG. 13 is a front plan view of a portion of the auto-injector illustrated in FIG. 5 in a third configuration.

Prior to use, the auto-injector 4002 is first enabled by removing the needle guard 4810 and the safety lock 4710 (see FIGS. 12 and 13). As illustrated by arrow AA in FIG. 12, the needle guard 4810 is removed by moving it distally. The needle guard 4810 includes a sheath retainer 4840 and a sheath 4820. The sheath 4820 is configured to receive a portion of the needle (not shown) when the needle guard 4810 is in a first (or installed) position. The sheath retainer 4840 is coupled to the sheath 4820 such that when the sheath retainer 4840 is moved distally away from the base 4520 into a second (or removed) position, the sheath 4820 is removed from the needle.

The sheath retainer 4840 includes an actuator 4864 that is received by an opening 4862 in the isolation tab 4860. Accordingly, when the sheath retainer 4840 is moved distally away from the base 4520, the isolation tab 4860 is removed from the area between the first electrical contact portion 4936 of the printed circuit board 4922 and the first surface 4964 of one of the batteries 4962. In this manner, the batteries 4962 can be operatively coupled to the electronic circuit system 4920 when the needle guard 4810 is removed, thereby actuating the electronic circuit system 4920.

When actuated, the electronic circuit system 4920 can output one or more predetermined electronic outputs. For example, in some embodiments, the processor 4950 can output an electronic signal associated with recorded speech to the audible output device 4956. Such an electronic signal can be, for example, associated with a .WAV file that contains a recorded instruction instructing the user in the operation of the auto-injector 4002. Such an instruction can state, for example, "remove the blue safety tab near the base of the auto-injector." The processor can simultaneously output an electronic signal to the first LED 4958A, thereby causing the first LED 4958A, which is located near the safety lock 4710, to flash a particular color. In this manner, the electronic circuit system 4920 can provide both audible and visual instructions to assist the user in the initial operation of the auto-injector 4002.

In other embodiments, the electronic circuit system 4920 can output an electronic output associated with a description and/or status of the auto-injector 4002 and/or the medicament contained therein. For example, in some embodiments, electronic circuit system 4920 can output an audible message indicating the type of medicament contained in the auto-injector, the expiration date of the medicament, the dosage of the medicament or the like.

As illustrated by arrow BB in FIG. 13, the safety lock 4710 is removed by moving it substantially normal to the longitudinal axis of the housing 4110. The safety lock 4710 has a first end 4712 and a second end 4714. When the safety lock 4710 is in its first (or locked) position, the second end 4714 extends around a portion of the base 4520 to space the base 4520 apart from the distal end portion 4114 of the housing 4110. Additionally, the first end 4714 includes a locking protrusion (not shown) that obstructs portions of the system actuator (not shown) further preventing the base 4520 from being moved proximally towards the housing 4110. Accordingly, when the safety lock 4710 is in its first position, the auto-injector 4002 cannot be actuated.

Figure 15:
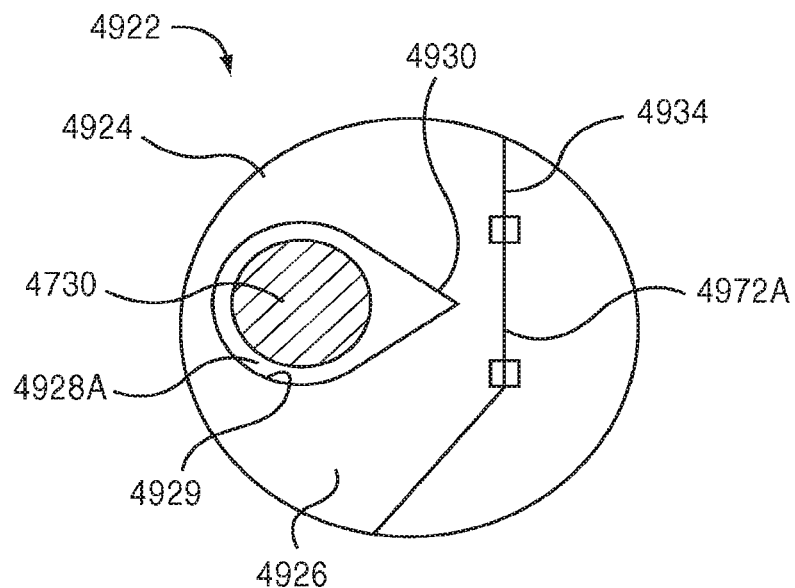
FIGS. 15 and 16 are front plan views of a portion of the auto-injector labeled as region 15 in FIG. 10, in a first configuration and a second configuration, respectively.
Figure 16:
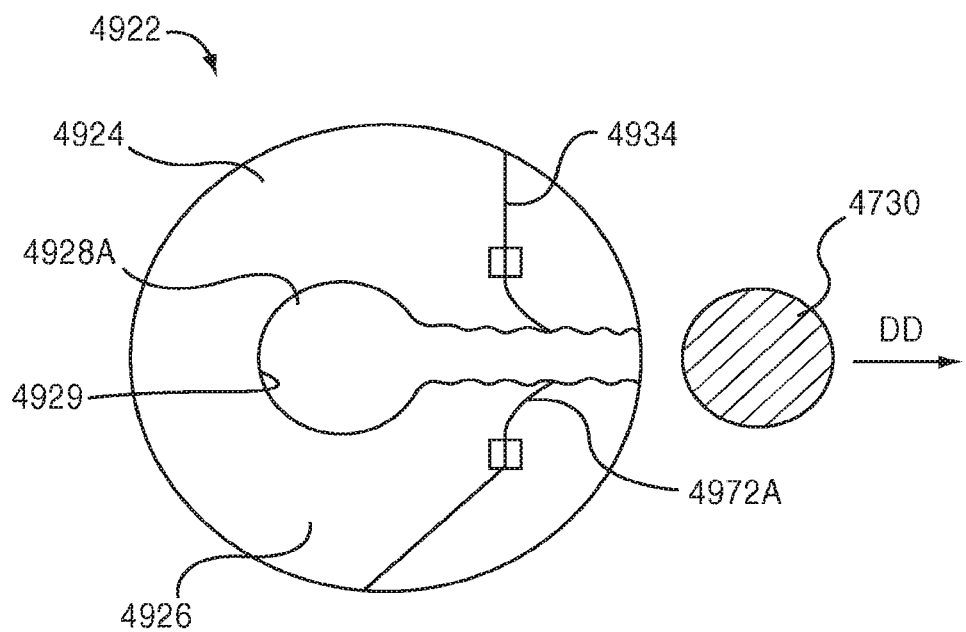

In some embodiments, the safety lock 4710 includes an actuator 4732 that actuates the electronic circuit 4920 to trigger a predetermined output or sequence of outputs when the safety lock 4710 is moved from the first position to a second (or unlocked) position, as shown in FIG. 13. More particularly, as shown in FIGS. 10, 15 and 16, the actuator 4732 includes a protrusion 4730 that is received within a first opening 4928A defined by an actuation portion 4926 of the substrate 4924 when the safety lock 4710 is in the first position. The boundary 4929 of the first opening 4928A has a discontinuous shape, such as, for example, a teardrop shape, that includes a stress concentration riser 4930. The discontinuity and/or the stress concentration riser 4930 of the boundary 4929 can be of any suitable shape to cause the substrate 4924 to deform in a predetermined direction when the protrusion 4730 is moved relative to the first opening 4928A.

As shown in FIGS. 15 and 16, the first opening 4928A is defined adjacent an electrical conductor 4934 that, as discussed above, electronically couples the components included in the electronic circuit system 4920. The electrical conductor 4934 includes a first switch 4972A, which can be, for example a frangible portion of the electrical conductor 4934. In use, when the safety lock 4710 is moved from the first position to the second position, the actuator 4732 moves in a direction substantially parallel to a plane defined by a surface of the actuation portion 4926 of the substrate 4924. The movement of the actuator 4732 causes the protrusion 4730 to move within the first opening 4928A, as indicated by the arrow DD in FIG. 16. The movement of the protrusion 4730 tears the actuation portion 4926 of the substrate 4924, thereby separating the portion of the electrical conductor 4934 including the first switch 4972A. Said another way, when the safety lock 4710 is moved to the second position, the actuator 4732 moves irreversibly the first switch 4972A from a first state (e.g., a state of electrical continuity) to a second state (e.g., a state of electrical discontinuity).

When the actuator 4732 actuates the electronic circuit system 4920 as described above, the electronic circuit system 4920 can output one or more predetermined electronic outputs. For example, in some embodiments, the processor 4950 can output an electronic signal associated with recorded speech to the audible output device 4956. Such an electronic signal can be, for example, associated with a recorded message notifying the user of the status of the auto-injector 4002. Such a status message can state, for example, "The auto-injector is now enabled." The processor can also simultaneously output an electronic signal to the first LED 4958A, thereby causing the first LED 4958A to stop flashing, change color or the like.

In some embodiments, the electronic circuit system 4920 can be configured to output the status message for a predetermined time period, such as, for example, five seconds. After the predetermined time period has elapsed, the electronic circuit system 4920 can output an audible message further instructing the user in the operation of the auto-injector 4002. Such an instruction can state, for example, "Place the base of the auto-injector against the patient's thigh. To complete the injection, press the base firmly against the patient's thigh." In some embodiments, the processor can simultaneously output an electronic signal to the second LED 4958B, thereby causing the second LED 4958B, which is located near the base 4520, to flash a particular color. In this manner, the electronic circuit system 4920 can provide both audible and visual instructions to assist the user in the placement and actuation of the auto-injector 4002. In some embodiments, the electronic circuit system 4920 can be configured to repeat the instructions after a predetermined time period has elapsed.

Figure 14:
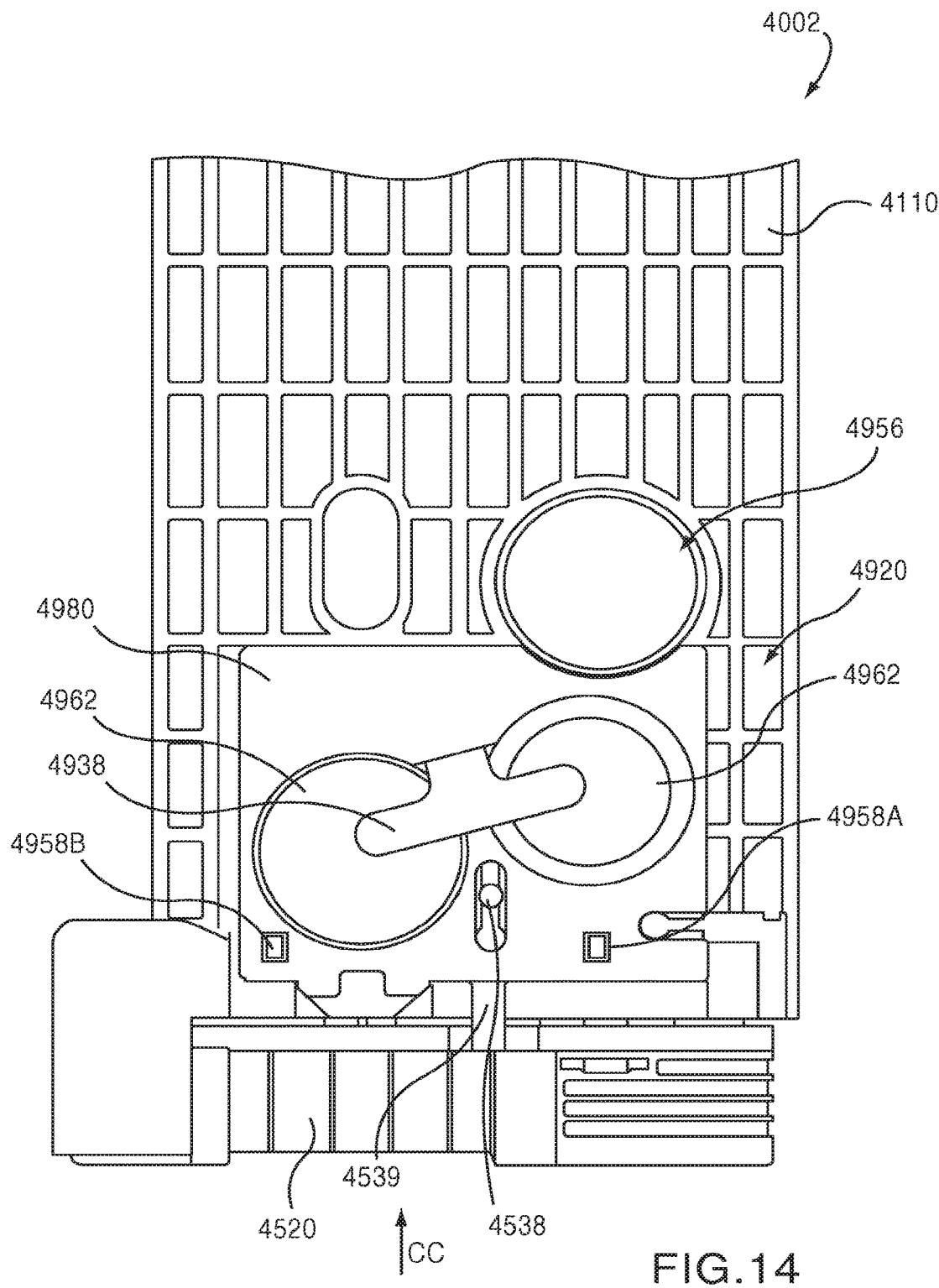
FIG. 14 is a front plan view of a portion of the auto-injector illustrated in FIG. 5 in a fourth configuration.

After the auto-injector 4002 is enabled and placed against the body of the patient, the auto-injector 4002 is actuated by moving the base 4520 proximally towards the housing 4110, as illustrated by arrow CC in FIG. 14. The base 4520 includes an actuator 4538 that actuates the electronic circuit 4920 to trigger a predetermined output or sequence of outputs when the base 4520 is moved from a first position to a second position, as shown in FIG. 13. The actuator 4538 includes a protrusion 4539 that is received within a second opening 4928B (see FIG. 10) defined by the substrate 4924 when the base 4520 is in the first position. The configuration and operation of the protrusion 4539, the second opening 4928B and the second switch 4972B are similar to the configuration and operation of the protrusion 4730, the first opening 4928A and the first switch 4972A, and are therefore not described in detail.

When the actuator 4538 actuates the electronic circuit system 4920, the electronic circuit system 4920 can output one or more predetermined electronic outputs. For example, in some embodiments, the processor 4950 can output an electronic signal associated with recorded speech to the audible output device 4956. Such an electronic signal can be, for example, associated with a recorded message notifying the user that the injection is complete, instructing the user on post-injection disposal and safety procedures, instructing the user on post-injection medical treatment or the like. Such a status message can state, for example, "The injection is now complete. Please seek further medical attention from a doctor." The processor can also simultaneously output an electronic signal to the first LED 4958A, thereby causing the first LED 4958A to stop flashing, change color or the like, to provide a visual indication that the injection is complete.

As described above, the audio output device 4956, can include, for example, a micro-speaker. In some embodiments, for example, the audio output device 4956 can include an RS-1511A micro-speaker manufactured by Regal Electronics, Inc.

Similarly, the microprocessor 4950 can be a commercially-available processing device dedicated to performing one or more specific tasks. For example, in some embodiments, the microprocessor 4950 can be a commercially-available microprocessor, such as the Sonix SNC 12060 voice synthesizer. Alternatively, the microprocessor 4950 can be an application-specific integrated circuit (ASIC) or a combination of ASICs, which are designed to perform one or more specific functions. In yet other embodiments, the microprocessor 4950 can be an analog or digital circuit, or a combination of multiple circuits.

The microprocessor 4950 can include a memory device (not shown) configured to receive and store information, such as a series of instructions, processor-readable code, a digitized signal, or the like. The memory device can include one or more types of memory. For example, the memory device can include a read only memory (ROM) component and a random access memory (RAM) component. The memory device can also include other types of memory suitable for storing data in a form retrievable by the microprocessor 4950, for example, electronically-programmable read only memory (EPROM), erasable electronically-programmable read only memory (EEPROM), or flash memory.

Figure 17:
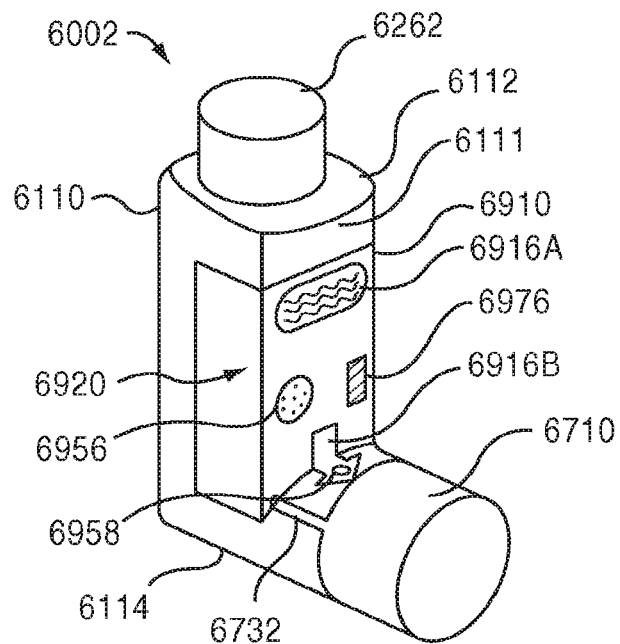
FIGS. 17 and 18 are perspective views of an inhaler according to an embodiment of the invention, in a first configuration and a second configuration, respectively.
Figure 18:
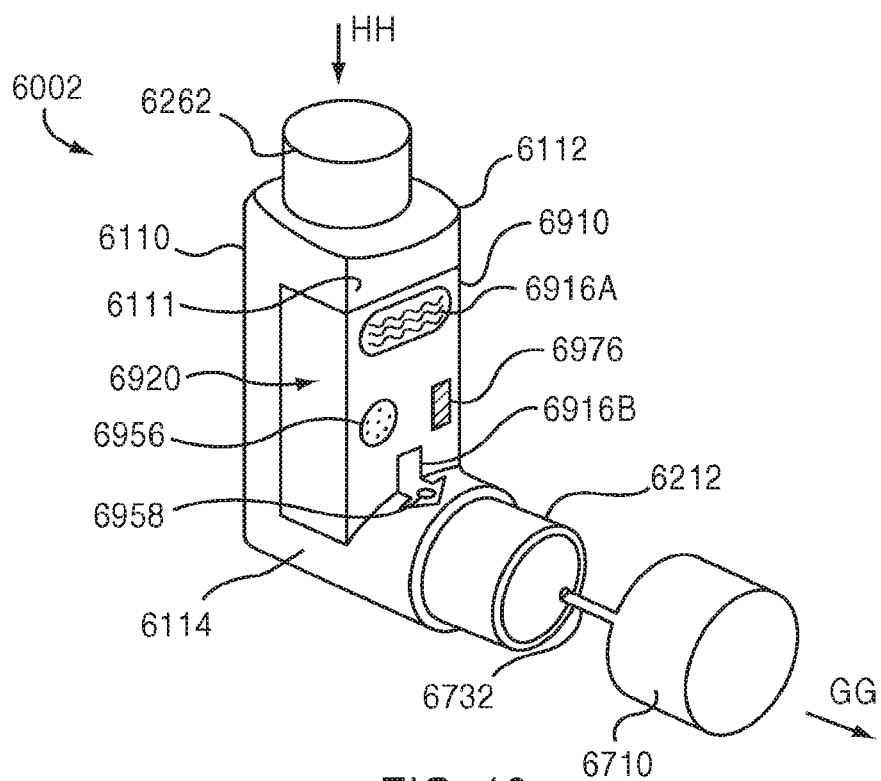

FIGS. 17 and 18 show an inhaler 6002 according to an embodiment of the invention. The inhaler 6002 includes a housing 6110 and a medicament container 6262 movably disposed within the housing 6110. The medicament container 6262 includes a metering mechanism (not shown in FIGS. 17 and 18) configured to discharge a predetermined volume of medicament when the inhaler 6002 is actuated.

The housing 6110 has a proximal end portion 6112 and a distal end portion 6114. An label 6910, which includes at least a portion of an electronic circuit system 6920, is disposed on an outer surface 6111 of the housing 6110. As described above, a portion of the label 6910 can include a textual indicia 6916. Similar to the electronic circuit systems shown and described above, the electronic circuit system 6920 is configured to output at least one electronic signal associated with the user of the inhaler 6002. The electronic circuit system 6920 includes a microprocessor (not shown), a microspeaker 6956 and an LED 6958. The electronic circuit system 6920 also includes a motion sensor 6976, the function of which is discussed in more detail below.

The distal end portion 6114 of the housing 6110 includes a mouthpiece 6212 about which a protective cap 6710 is disposed. Prior to use, the inhaler 6002 is first enabled by removing the protective cap 6710, as shown by the arrow GG in FIG. 18. The protective cap 6710 includes an actuator 6732 that actuates the electronic circuit system 6920 to trigger a predetermined output or sequence of outputs when the protective cap 6710 is removed. In some embodiments, the actuator 6732 can include a protrusion that is received by an actuation portion of the electronic circuit system 6920, in a similar manner as described above. In other embodiments, the actuator 6732 can be configured to engage a microswitch that can be repeatedly moved between a first state and a second state.

When actuated, the electronic circuit system 6920 can output one or more predetermined electronic outputs. For example, in some embodiments, the electronic circuit system 6920 can output an audible message via the microspeaker 6956 instructing the user to "vigorously shake the inhaler for five seconds." The processor can simultaneously enable the motion sensor 6976.

Upon receiving a predetermined input from the motion sensor 6976, which can be any sensor suitable for detecting the rapid motion of the inhaler 6002, the processor can then send an electronic signal to produce a second audible message. Such a message can state, for example, "the inhaler is now sufficiently shaken and is ready for use." In some embodiments, the electronic circuit system 6920 can also output an instruction associated with the correct placement of the inhaler 6002. For example, the electronic circuit system 6920 can output an audible message stating "please place the mouthpiece in your mouth and firmly press down on the medicament container." The electronic circuit system 6920 can also simultaneously output a signal to the LED 6958 to provide a visual indication of where the mouthpiece 6212 is located.

After the inhaler 6002 is enabled and placed within the mouth of the patient, the inhaler 6002 is actuated by moving the medicament container 6262 distally within housing 6110, as illustrated by arrow HH in FIG. 18. In some embodiments, the medicament container 6262 can include an actuator (not shown) that actuates the electronic circuit 6920, in a manner similar to those described above, to trigger a predetermined output or sequence of outputs. For example, in some embodiments, the processor can output an electronic signal associated with recorded speech to the microspeaker 6956. Such an electronic signal can be, for example, associated with a recorded message notifying the user that the medicament delivery is complete, instructing the user on post-inhalation procedures, instructing the user on post-inhalation medical treatment or the like. Such a status message can state, for example, "The delivery of medication is now complete."

As described above, although not explicitly shown in FIGS. 5-14, in some embodiments, an electronic circuit system of a medicament delivery device can include a network interface device. Similarly stated, in some embodiments, the auto-injector 4002 can be configured to send electronic signals to and/or receive electronic signals from a communications network and/or a remote device. The remote device can be, for example, a compliance monitoring device, a computer, a cell phone, a personal digital assistant (PDA) or the like. In this manner, the auto-injector 4002 can facilitate electronic and/or automatic compliance monitoring associated with its use.

Figure 19:
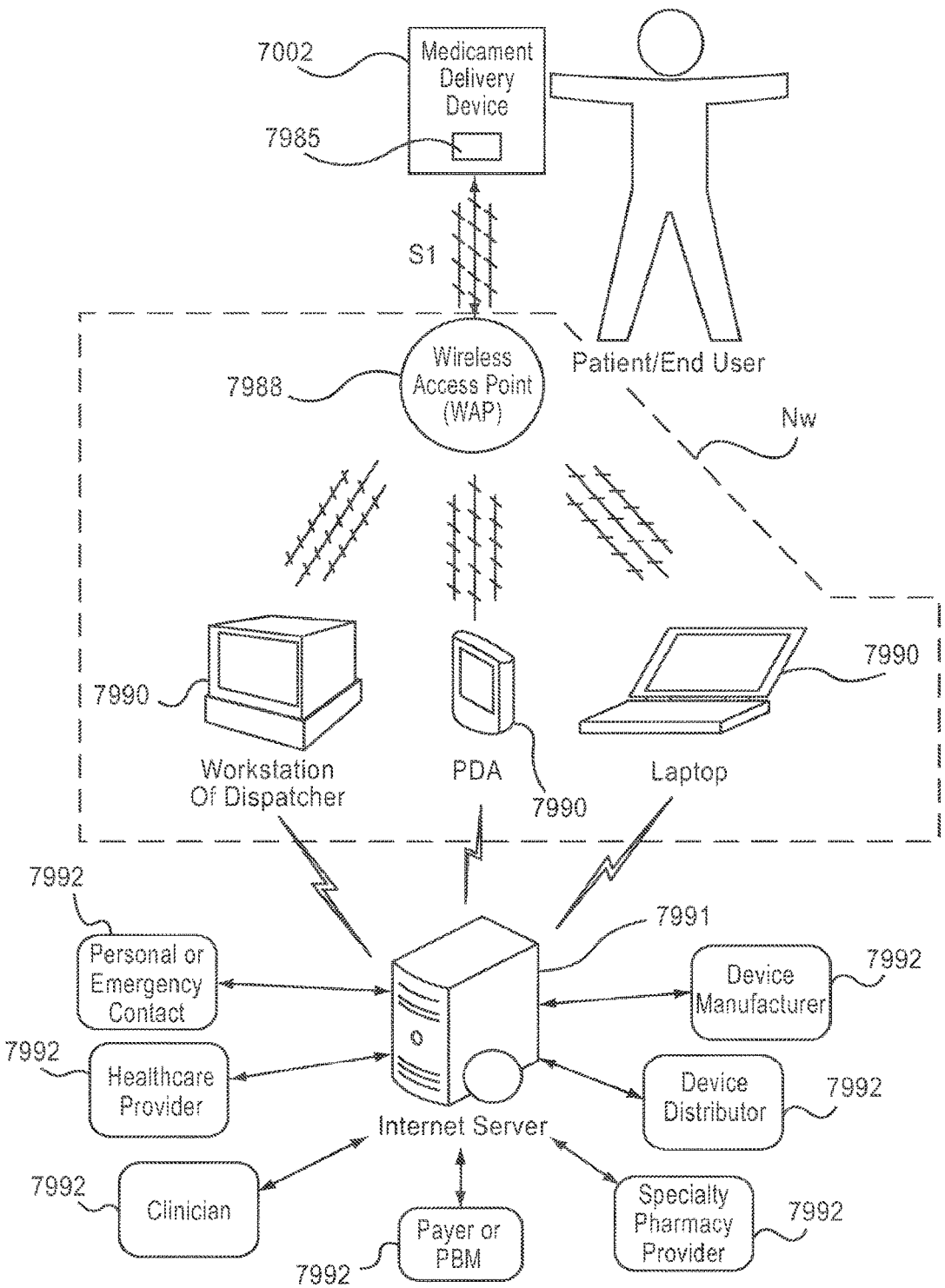
FIG. 19 is a schematic illustration of a medicament delivery device according an embodiment of the invention.

In some embodiments, for example, a medicament delivery device can include a network interface device configured to send and/or receive electrical signals via a wireless network. For example, FIG. 19 is a schematic illustration of a medicament delivery device 7002 according an embodiment of the invention that includes a wireless communications system 7985. The wireless communications system 7985 is configured to send and/or receive one or more electronic signals S1 to a variety of communications devices 7990 via a wireless communications network $N_W$. The wireless communication network $N_W$ includes a wireless access point (WAP) 7988 configured to operatively connect the communications devices 7990 and the wireless communications system 7985 on the medicament delivery device 7002 to form the wireless communications network $N_W$. As described herein, the communications devices 7990 can include, for example, a laptop computer, a personal digital assistant, a compliance monitoring device, a stand-alone processor, a workstation and/or the like. Moreover, as shown in FIG. 19, the communications devices 7990 can be configured to communicate electronically to an internet server 7991 by sending electronic signals to and/or receiving electronic signals from the internet server. In this manner, the wireless communications system 7985 can transmit information associated with the medicament delivery device 7002 to and/or receive information associated with the medicament delivery device 7002 from any number of third party devices 7992 located anywhere in the world.

In use, the wireless communications system 7985 can be used to send and/or receive information associated with the medicament delivery device 7002. Such information can include, for example, information associated with the frequency with which medicament delivery device 7002 is used (e.g., a compliance log), the functionality of the medicament delivery device 7002 after use (e.g., the number of doses remaining), the date and/or time of use, a parameter measuring the success of the latest use of the medicament delivery device 7002, an expiration date of the medicament delivery device 7002 and/or the medicament contained therein, a status of the medicament delivery device 7002 and/or the medicament contained therein, instructions for using the medicament delivery device 7002, the need for additional medical devices, the need for additional drug dosages, and/or any other information that may be useful to users and/or medical professionals associated with the medicament delivery device 7002. For example, in some embodiments, the wireless communications system 7985 can send one or more signals S1 including information related to a user's compliance to the user's home computer and/or a compliance monitoring device. In this manner, the user can use their home computer to track their compliance with a prescribed medication regimen or other usage of the medicament delivery device 7002. In other embodiments, the wireless communications system 7985 can send one or more signals S1 including information related to a user's compliance to a third party. Such third parties can include, for example, a health care provider, an emergency contact, a manufacturer of the medicament delivery device 7002, a pharmaceutical benefits manager (PBM), a specialty pharmacy, a payor (e.g., an insurance company), a clinical trial administrator, an on-line support group or forum, and/or a pharmaceutical company. For example, in some embodiments, the wireless communications system 7985 can send one or more signals S1 including information related to a user's compliance to the user's health care provider. In this manner, the health care provider can monitor the user's compliance with the prescribed medication regimen.

The wireless communications system 7985 can include any hardware, software and/or firmware suitable for wireless communication. For example, in some embodiments, the wireless communications system 7985 can include a microprocessor, a transmitter, a receiver, a transceiver, a microchip, a radio chipset, a wireless interface card (WIC), a host controller interface (HCI), a universal asynchronous receiver/transmitter (UART), a power source (e.g., a battery), one or more sensors, a transponder, an antenna, a crystal, a circuit board, a liquid crystal display (LCD), a Small Computer System Interface (SCSI and ports), a FireWire (or other IEEE 1394 interfaces), a data uplink, a data downlink, a point-to-point link, a fiber optic link, a storage device (e.g., hard drive, flash drive or the like), a personal computer cards, a docking stations, a parallel and/or bit-serial connections, a Universal Serial Bus (USB) port or other serial ports, a light emitting diode (LEDs), a speaker, an amplifier, radiofrequency identification (RFID) devices and/or other common electronic components used for wireless communication. The electronic components can be operatively coupled to form the wireless communications system 7985 by any suitable circuitry. In some embodiments, the wireless communications system 7985 can include the components used for wireless communication on a single chip, such as, for example, the Bluetooth™ radio chip LMX9830 manufactured by National Semiconductor.

As described above, the wireless access point WAP is configured to establish the wireless network $N_W$ and to transmit electronic signals between the medicament delivery device 7002 (which can be referred to as a wireless client device), wireless communications devices 7990 (which can be referred to as other wireless client devices) and/or other third party devices 7992. In some embodiments, the wireless communications devices 7990 and/or other third party devices 7992 can include, for example, laptops (computers), personal digital assistants (PDAs), wireless IP phones, servers, routers, and other wireless enabled network devices. Although the wireless access point WAP is shown and described as being distinct from the wireless communications system 7985, in some embodiments, the wireless communications system 7985 can include the functionality of a wireless access point. In this manner, the medicament delivery device 7002 can be utilized as a wireless access point. In yet other embodiments, the wireless communications system 7985 can send and/or receive electronic signal S1 without the use of a wireless access point. In such embodiments, which can be referred to as peer-to-peer networks or ad-hoc networks, the wireless communications system 7985 can communicate directly with the wireless communications devices 7990 and/or other third party devices 7992.

The wireless communication system 7985 can employ any suitable protocol or protocols for sending and/or receiving the electronic signals S. Such protocols can include, for example, Wi-Fi, Bluetooth™, Zigbee, Wi-Max, 802.XX, HomeRF, any protocols associated with Radio Frequency Identification (RFID) transmission and/or a combination thereof. In some embodiments, the wireless communications system 7985 can employ a protocol having heightened security, such as for example, varying levels of encryption. In this manner any information associated with the medical records of a user can be protected against unauthorized access.

In addition to encryption, in some embodiments, the information transmitted and/or received by the wireless communication system 7985 can be in a format configured to prevent the identification of the user. For example, in some embodiments, the information transmitted and/or received by the wireless communication system 7985 can be associated with a unique identification number known only by certain parties, such as, for example, the end user and the end user's physician.

The wireless communications network $N_W$ can have any suitable range. For example, in some embodiments, the wireless communications network $N_W$ can be a wireless local area network (WLAN). A WLAN can be suitable in certain conditions in which the communications devices 7990 are confined to a limited geographical area, such as, for example, within a hospital, a nursing home or a triage unit. In other embodiments, the wireless communications network $N_W$ can be a wireless metropolitan area network (WMAN). A WMAN can be suitable in certain conditions in which the communications devices 7990 are used within a predefined area that cannot easily be covered by a WLAN, such as, for example, within a city. In yet other embodiments, the wireless communications network $N_W$ can be a wireless wide area network (WWAN).

Although the arrangement shown in FIG. 19 shows the wireless communication system 7985 sending information to and/or receiving information from the third party devices 7992 via the wireless access point 7988 and the wireless communications devices 7990, in other embodiments, the wireless communication system 7985 can transmit information to and/or receive information from the third party devices 7992 directly. For example, in some embodiments, third party devices 7992 can be included within the wireless communications network $N_W$, which can be, for example, a wireless wide area network (WWAN).

The medicament delivery device 7002 can be any device suitable for delivering one or more doses of a medicament into a patient's body. As described herein, such devices can include, for example, auto-injectors, pen injectors, inhalers, transdermal patches, pre-filled syringes (PFS), syringes, catheters, stents, implantable vehicles, topical vehicles, pill dispensers or the like. In some embodiments, for example, the medicament delivery device 7002 can be a single-dose device typically used in emergency situations. For example, in some embodiments, the medicament delivery device 7002 can be a single-use medical injector, similar to auto-injector 4002 shown and described above with reference to FIGS. 5-16. In such embodiments, the wireless communications system 7985 can be configured to send automatically data to a workstation and/or a compliance monitoring device during the various stages of operation of the medicament delivery device 7002. In this manner, the details of each stage of operation of the medicament delivery device 7002 can be electronically and/or automatically recorded to track patient compliance. Such details can include, for example, a time stamp associate with the removal of a safety mechanism (i.e., the "arming" of the medicament delivery device), a time stamp associated with the actuation of the medicament delivery device, an indicator associated with the validity of the medicament delivery event and/or the like.

In other embodiments, the medicament delivery device 7002 can be a chronic-care medicament delivery device containing multiple doses of medicament configured to be delivered on a regular schedule. In some embodiments, for example, the medicament delivery device 7002 can be a chronic-care pen injector used for injectable pharmaceuticals that require daily, weekly and/or monthly injections, such as, for example, insulin or human growth hormone (HgH). In such embodiments, the wireless communication system 7985 can track the usage of the pen injector and transmit the use information to the patient's physician, specialty pharmacy, payor (e.g., an insurance company), PBM, clinical trial administrator or other provider. In this manner, for example, the patient's physician can ensure that the therapy regime is effective.

In yet other embodiments, the medicament delivery device 7002 can be a single-use and/or disposable chronic-care medicament delivery device. As described in more detail herein, in such embodiments the medicament delivery device 7002 can be included within a kit containing the desired number of doses of medicament.

Figure 20:
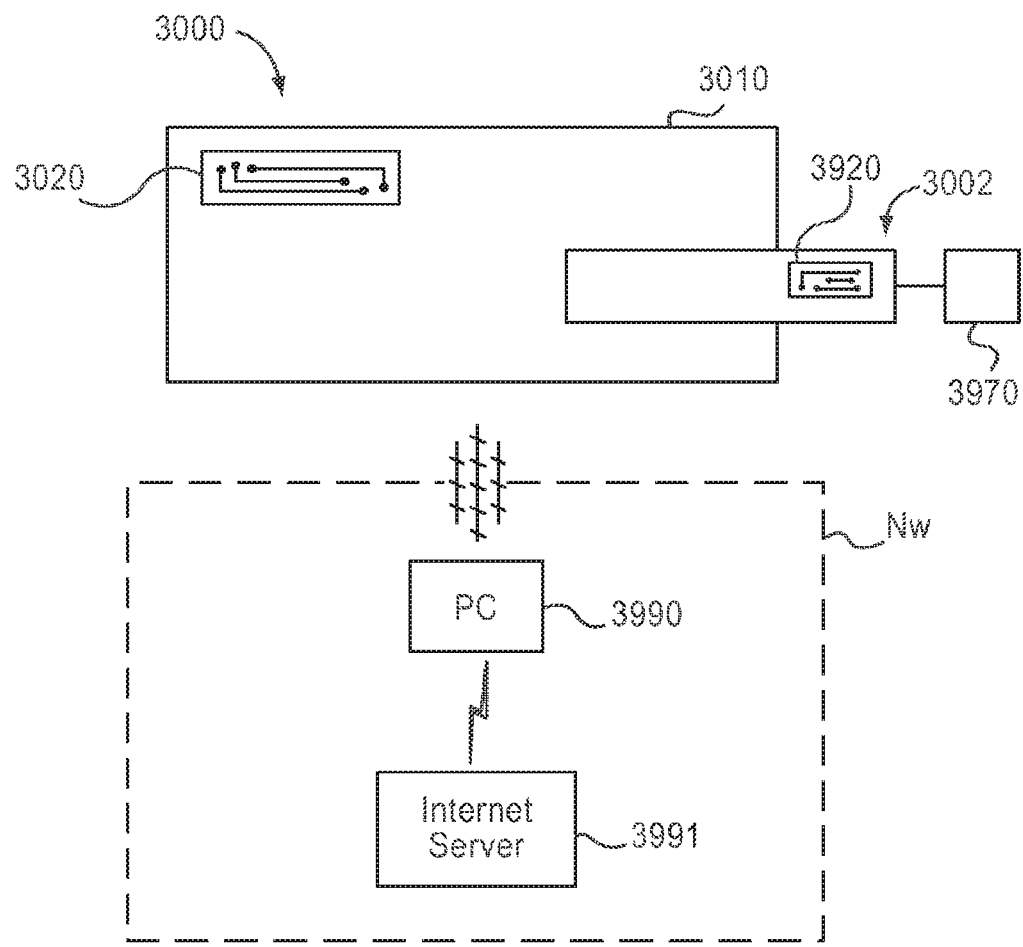
FIGS. 20-22 are schematic illustrations of a medical system according to an embodiment of the invention, in a first configuration, a second configuration and a third configuration, respectively.
Figure 21:
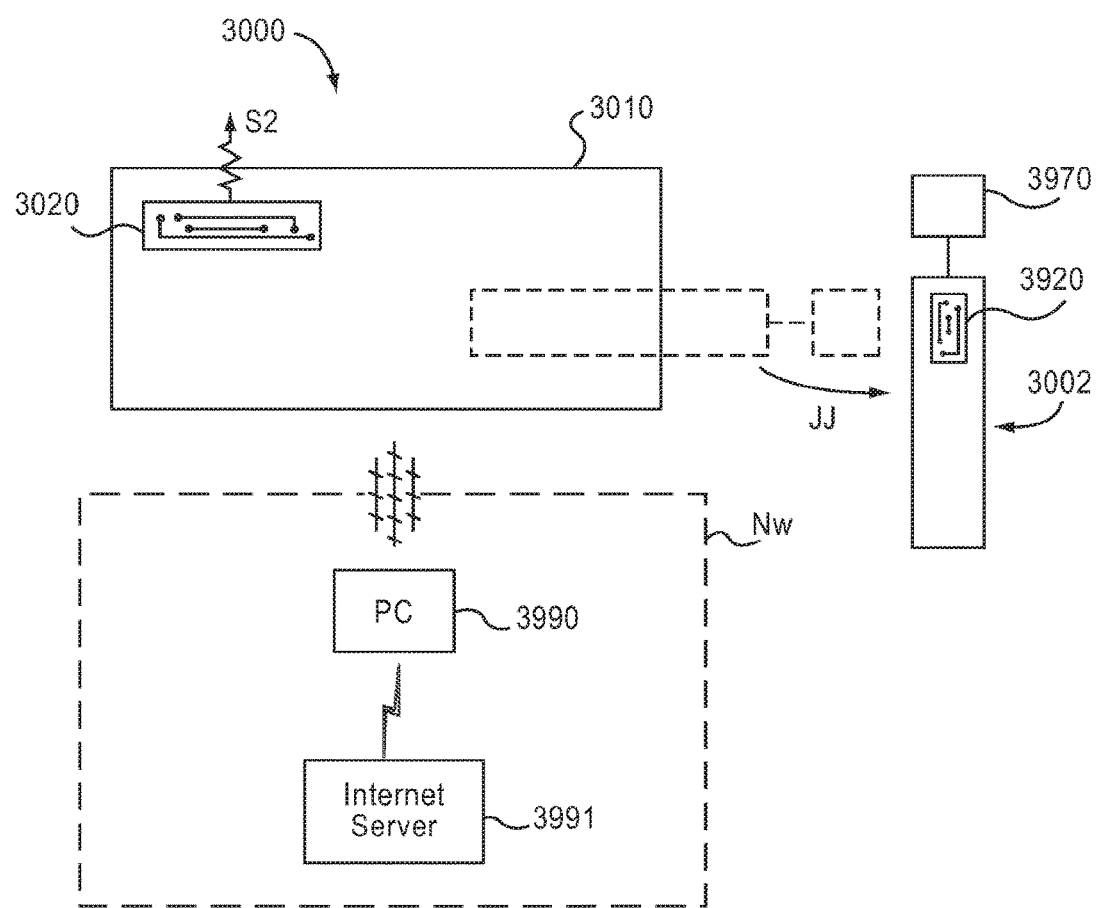
Figure 22:
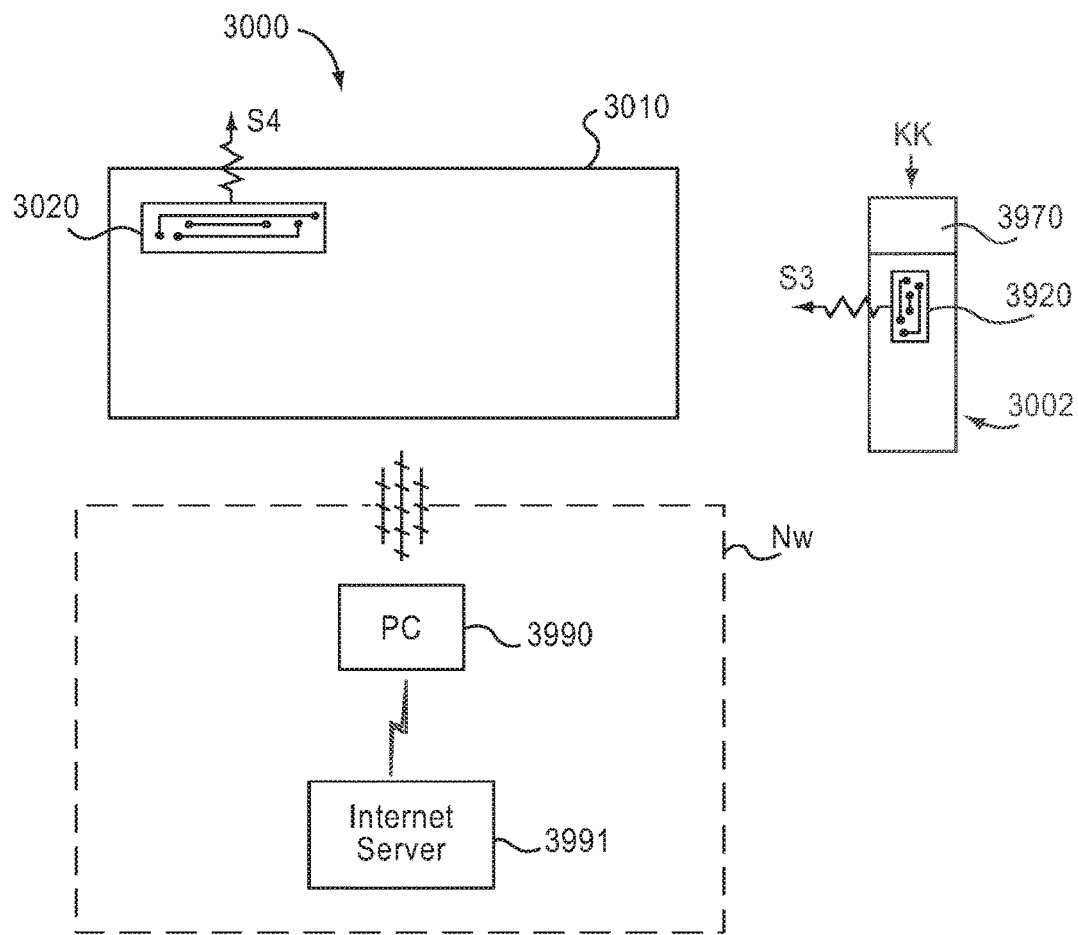

As described above, in some embodiments, a medicament delivery device can be configured to produce and/or output an electrical signal when the medicament delivery device is actuated. In this manner, patient compliance data, such as, for example, the frequency of use, the date and time of use and/or a parameter measuring the success and/or validity of the use of the medicament delivery device can be monitored based on the actuation of the medicament delivery device, rather than on the removal of a safety interlock from the medicament delivery device. For example, FIGS. 20-22 are schematic illustrations of a medical system 3000 according to an embodiment of the invention, in a first configuration, a second configuration and a third configuration, respectively. The medical system 3000 includes a medicament delivery device 3002 and a container 3010. As shown in FIG. 20, the container 3010 is configured to receive at least a portion of the medicament delivery device 3002. For example, in some embodiments, the container 3010 can include a recessed portion, a retainer, and/or any other suitable structure that matingly receives at least a portion of the medicament delivery device 3002.

The container 3010 includes an electronic circuit system 3020 configured to output at least electronic signals S2 and S4, as described in more detail herein. The electronic circuit system 3020 can include any suitable electronic components operatively coupled to produce and/or output the electronic signal S2 and S4, and/or to perform the functions described herein. The electronic circuit system 3020 is operatively coupled to the communications network $N_W$, which includes at least a personal computer (PC) 3990 or other processor, and an internet server 3991. In some embodiments, for example, the electronic circuit system 3020 can include a wireless communications device, similar to the wireless communications system 7985 shown and described above with reference to FIG. 19, to wirelessly connect the electronic circuit system 3020 to the PC 3990 and/or the communications network $N_W$. In other embodiments, the electronic circuit system 3020 can be operatively coupled to the PC 3990 and/or the communications network $N_W$ via a wired connection. In this manner, as described in more detail herein, the electronic circuit system 3020 of the container 3010 can transmit information associated with the medical system 3000 to and/or receive information associated with the medical system 3000 from any number of remotely located third party devices (not shown in FIGS. 20-22).

The medicament delivery device 3002 can be any device for delivering a medicament into a body, such as, for example, a medical injector (which can include an auto-injector, a pen injector, a multiple-use injector, a syringe or the like), an inhaler or the like. The medicament delivery device 3002 includes an actuator 3970 and an electronic circuit system 3920. The actuator 3970 is movable between a first position (FIGS. 20 and 21) and a second position (FIG. 22). When the actuator 3970 is moved from the first position to the second position, the actuator 3970 initiates the delivery of the medicament into the body. In some embodiments, the actuator 3970 can be configured to release a spring, an energy storage member, or the like, to initiate medicament delivery when the actuator 3970 is moved from the first position to the second position. For example, in some embodiments, the actuator can be similar to the base 4520 shown and described above with reference to FIGS. 5-16.

The electronic circuit system 3920 of the medicament delivery device 3002 is configured to output at least an electronic signal S3 (see FIG. 22) when the actuator 3970 is moved from the first position to the second position. The electronic circuit system 3920 of the medicament delivery device 3002 can include any suitable electronic components operatively coupled to produce and/or output the electronic signal S3 and/or to perform the functions described herein. In some embodiments, for example, the electronic circuit system 3920 of the medicament delivery device 3002 can be similar to the electronic circuit system 4920 shown and described above with reference to FIGS. 5-16.

The medical system 3000 can be used to manage the patient's medication regimen and/or track the patient's compliance in following the prescribed medication regimen. When the medical system 3000 is in the first configuration (i.e., the "storage configuration"), as shown in FIG. 20, at least a portion of the medicament delivery device 3002 is disposed within the container 3010, and the electronic circuit system 3020 of the container 3010 is operatively coupled to the communications network $N_W$, and/or the personal computer (PC) 3990. In some embodiments, when the medical system 3000 is in the first configuration, the electronic circuit system 3020 can optionally output one or more electronic signals (not shown in FIG. 20) associated with the medication regimen and/or the medicament delivery device 3002. Such electronic signals can include, for example, a visual and/or an audible output reminding the patient of the date and time of the next dosage, indicating the expiration date of the medicament delivery device, providing instructions in the use of the medicament delivery device, providing instructions for monitoring compliance, or the like.

To move the medical system 3000 from the first configuration to the second configuration (i.e., a "pre-delivery" configuration), the medicament delivery device 3002 is removed from the container 3010, as shown by the arrow JJ in FIG. 21. When the medicament delivery device 3002 is removed from the container 3010, the electronic circuit system 3020 of the container 3010 produces the first electronic signal S2. The first electronic signal S2 can be associated with the prescribed medication regimen (including, for example, compliance data), an identification of the medicament delivery device 3002, a status of the medicament delivery device 3002, a use instruction associated with the medicament delivery device 3002, a status of the container 3010 (including, for example, an indication of whether the electronic circuit system 3020 of the container 3010 is connected to the network $N_W$, the remaining battery life of a battery powering the electronic circuit system 3020, or the like), a use instruction associated with the container 3010 and/or the like. In some embodiments, for example, the first electronic signal S2 can include a visual output, an audible output and/or a haptic output that instructs and/or provides cues to a user in the use of the container 3010 to track the patient's compliance. In other embodiments, the first electronic signal S2 can include a communications signal that can be transmitted via the PC 3990 and the internet server 3991 to a remotely located third party device (not shown in FIGS. 20-22).

To move the medical system 3000 from the second configuration to the third configuration (i.e., a "post-delivery" configuration), the medicament delivery device 3002 is actuated by moving the actuator 3970 from the first position (FIG. 21) to the second position (FIG. 22), as shown by the arrow KK in FIG. 22. When the actuator 3970 is moved from the first position to the second position, actuation of the medicament delivery device is initiated. Said another way, the actuator 3970 is configured to initiate delivery of the medicament when the actuator 3970 is moved from the first position to the second position. As described above, the actuator 3970 can be configured to release a spring, an energy storage member, or the like, to initiate medicament delivery when the actuator 3970 is moved from the first position to the second position.

When the actuator 3970 is moved from the first position to the second position, the electronic circuit system 3920 of the medicament delivery device 3002 outputs the second electronic signal S3. Said another way, when actuator 3970 is moved from the first position to the second position, the actuator 3970 actuates the electronic circuit system 3920 of the medicament delivery device 3002 such that the electronic circuit system 3920 produces and/or outputs the second electronic signal S3. In some embodiments, the movement of the actuator 3970 produces an input that is received by the electronic circuit system 3920, thereby triggering the electronic circuit system 3920 to produce and/or out the second electronic signal S3. Said another way, in some embodiments, the movement of the actuator 3970 changes the state of a switch (not shown in FIGS. 20-22) within the electronic circuit system 3920, thereby triggering the electronic circuit system 3920 to produce and/or output the second electronic signal S3. Such a switch can be either reversible or irreversible, as described above. For example, in some embodiments, the movement of the actuator 3970 can separate, tear, deform and/or sever an electrical conductor (not shown in FIGS. 20-22) within the electronic circuit system 3920. For example, in some embodiments, the actuator 3970 can include a protrusion (not shown in FIGS. 20-22) configured to be received within and sever a portion of the electronic circuit system 3920, similar to the protrusion 4730 shown and described above with reference to FIGS. 14-16. In other embodiments, the movement of the actuator 3970 can electronically couple and/or decouple a power source (not shown in FIGS. 20-22) to a portion of the electronic circuit system 3920. For example, in some embodiments, the actuator 3970 can include a battery isolation tab (not shown in FIGS. 20-22) configured to isolate a battery from a portion of the electronic circuit system 3920, similar to the battery isolation tab 4860 shown and described above with reference to FIGS. 7, 9 and 12.

The second electronic signal S3 is received by the electronic circuit system 3020 of the container 3010, which then produces the third electronic signal S4. The third electronic signal S4 is associated with the second electronic signal S3. In this manner, the electronic circuit system 3020 of the container 3010 and the electronic circuit system 3920 of the medicament delivery device 3002 can cooperatively monitor the patient's compliance in using the medicament delivery device 3002. By utilizing two electronic circuit systems, the electronic circuit system 3920 and the electronic circuit system 3020 can be cooperatively designed to provide the desired functionality. For example, in some embodiments, the container 3010 can be a reusable compliance tracking device and the medicament delivery device 3002 can be a single-use, disposable device. In such an arrangement, the electronic circuit system 3020 of the container 3010 can include complicated circuit elements, circuit elements having a higher cost, and/or circuit elements having higher power consumption (e.g., speakers, long-range wireless communications systems and the like). Conversely, the electronic circuit system 3920 of the medicament delivery device 3002 can include fewer circuit elements, circuit elements having a lower cost, and/or circuit elements having lower power consumption. In some embodiments, for example, the electronic circuit system 3920 of the medicament delivery device 3002 can include a transceiver (not shown in FIGS. 20-22) that consumes less than approximately 100 mA (at a supply voltage of approximately 1.8 volts) when outputting the second electronic signal S3. In other embodiments, the electronic circuit system 3920 of the medicament delivery device 3002 can include a transceiver (not shown in FIGS. 20-22) that consumes less than approximately 20 mA (at a supply voltage of approximately 1.8 volts) when outputting the second electronic signal S3. Such an arrangement can facilitate the use of the electronic circuit system 3920 on a single-use, disposable medicament delivery device.

The second electronic signal S3 can be any suitable communications signal (e.g., a radio frequency signal) that can be received by the electronic circuit system 3020 of the container 3010. For example, in some embodiments, the second electronic signal S3 can be a short-range radio frequency signal having a range of approximately 100 meters or less. In some embodiments, the second electronic signal S3 can be a Bluetooth™-compatible electronic signal, including either a class 1, class 2 or class 3 signal. Said another way, in some embodiments, the electronic circuit system 3920 of the medicament delivery device 3002 and the electronic circuit system 3020 of the container 3010 can be Bluetooth™-enabled circuits. In this manner, the medicament delivery device 3002 can electronically communicate with the container 3010 using low-cost circuit elements and/or using circuit elements having minimal power consumption.

The third electronic signal S4 can be any suitable electronic signal that can be produced and/or output by the electronic circuit system 3020 of the container 3010. For example, in some embodiments, the third electronic signal S4 can be output to an audio output device and/or a video output device (not shown in FIGS. 20-22) within the electronic circuit system 3020. In this manner, the electronic circuit system 3020 of the container 3010 can produce an audible and/or a visual output associated with the actuation of the medicament delivery device 3002. For example, in some embodiments, the third electronic signal S4 can be output to a speaker of the types shown and described above, thereby providing the user with a message associated with the use of and/or the compliance with the medicament delivery device 3002. In some embodiments, the third electronic signal S4 can be associated with a message instructing the user on post-injection disposal, safety procedures, post-injection medical treatment or the like. Such a message can state, for example, "THE DOSAGE OF XXX HAS BEEN SUCCESSFULLY ADMINISTERED. PLEASE SEEK FURTHER MEDICAL ATTENTION FROM A DOCTOR IF THE FOLLOWING SYMPTOMS OCCUR . . . " In other embodiments, the third electronic signal S4 can be associated with a message related to procedures for tracking compliance with the medication regimen. Such a message can state, for example, "THE SUCCESSFUL DOSAGE OF XXX HAS BEEN RECORDED TO YOUR ELECTRONIC COMPLIANCE LOG. NO FURTHER ACTION IS REQUIRED." In other embodiments, such a message can state, "PLEASE ENSURE THAT YOU RECORD THE CORRECT DOSAGE IN YOUR ELECTRONIC LOGBOOK." In yet other embodiments, such a message can state, "PLEASE DO NOT EAT OR DRINK UNTIL XX P.M." In yet other embodiments, such a message can state, "THE COMPLIANCE MONITOR IS CURRENTLY DISCONNECTED FROM THE NETWORK. PLEASE ENSURE THAT THE COMPLIANCE MONITOR IS CONNECTED TO YOUR HOME COMPUTER."

In some embodiments, the third electronic signal S4 can be a communications signal (e.g., a radio frequency signal) that can be transmitted from the electronic circuit system 3020 of the container 3010 to the PC 3990 and/or the communications network $N_W$. Such transmission can occur using any suitable method and/or protocol. The third electronic signal S4 can be transmitted, for example, in the form of an e-mail, a phone call, a data stream or the like.

In some embodiments, for example, the third electronic signal S4 can be associated with the patient's compliance in using the medicament delivery device 3002. For example, in some embodiments, the third electronic signal S4 can be sent via the communications network $N_W$ to the patient's pharmacy to automatically order additional pre-filled medicament delivery devices and/or replacement cartridges for the medicament delivery device. In other embodiments, the third electronic signal S4 can be sent via the communications network $N_W$ to a health care provider, thereby allowing the health care provider to remotely monitor the patient's medication regimen. In yet other embodiments, the third electronic signal S4 can be sent via the communications network $N_W$ to a clinical trial administrator, thereby allowing the clinical trial administrator to ensure that the clinical trial protocols are being properly followed.

Figure 23:
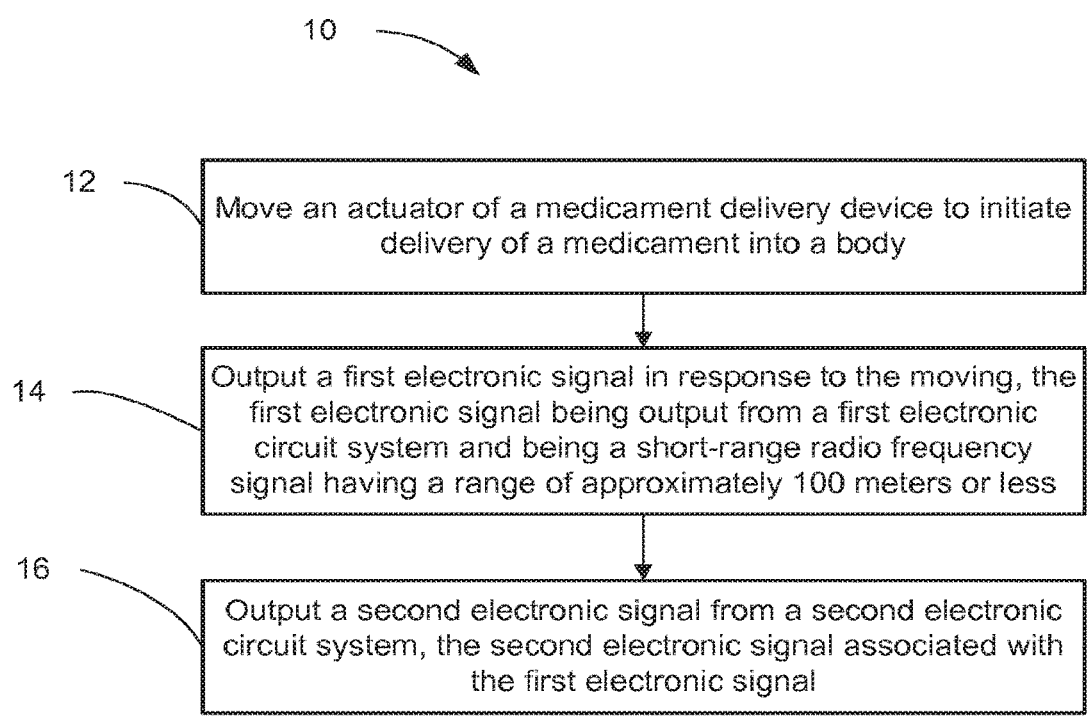
FIG. 23 is a flow chart of a method according to an embodiment of the invention.
Figure 24:
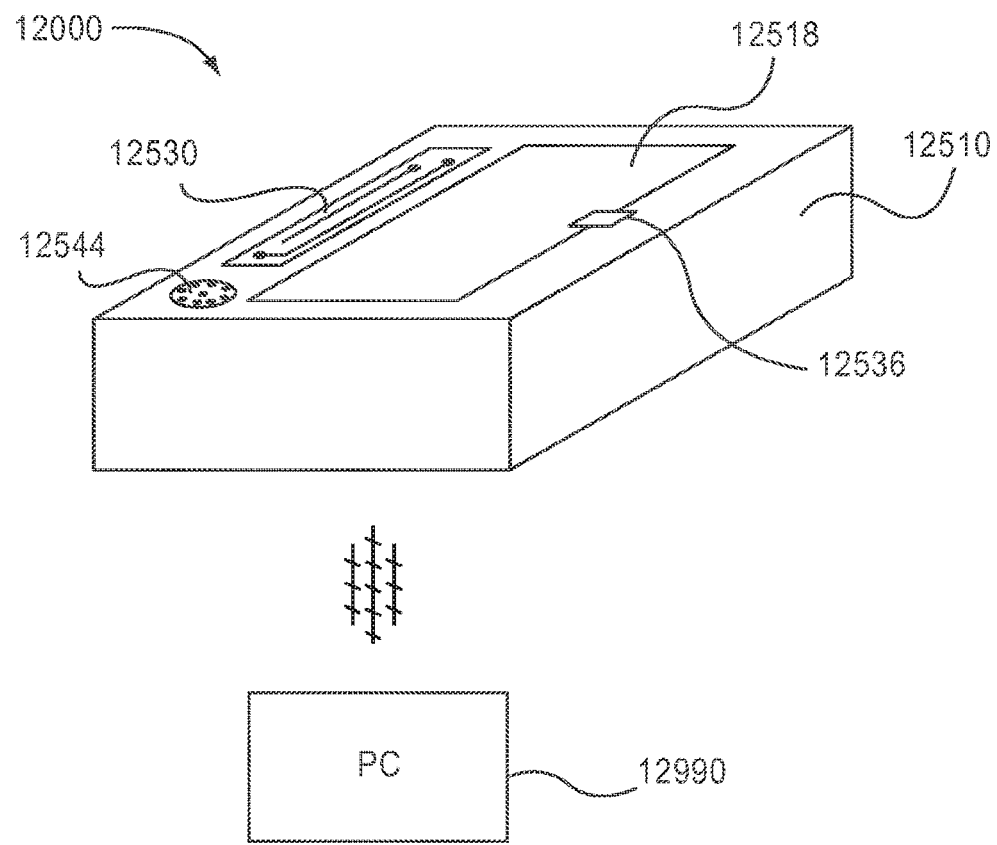
FIGS. 24-27 are perspective views of a medical system according to an embodiment of the invention, in a first configuration, a second configuration, a third configuration, and a fourth configuration, respectively.

FIG. 23 is a flow chart of a method 10 according to an embodiment of the invention. The method includes moving an actuator on a medicament delivery device to initiate delivery of a medicament into a body, 12. The actuator can be any suitable actuator configured to initiate the delivery of medicament into the body, as described above. For example, in some embodiments, the actuator can be configured to release a spring, an energy storage member, or the like, to initiate medicament delivery when the actuator is moved. In some embodiments, the method can optionally include moving one or more safety locks before the actuator is moved. Such safety locks can be similar to the safety lock 4710 shown and described above with reference to FIGS. 5-16, and can be configured to prevent the actuator from being moved.

A first electronic signal is then output from a first electronic system in response to the movement of the actuator, 14. The first electronic signal is a short-range radio frequency signal having a range of approximately 100 meters or less. In some embodiments, for example, the first electronic signal can be a Bluetooth™-compatible electronic signal, including either a class 1, a class 2 or a class 3 signal. In other embodiments, the first electronic signal can be a short-range signal produced by a radio frequency identification ("RFID") tag within the first electronic circuit system. In this manner, the first electronic circuit system can produce and/or output the first electronic signal using electronic devices having a low power consumption, as described above. As described in more detail herein, in some embodiments, the first electronic circuit system can be devoid of a battery.

The first electronic circuit system can be any suitable electronic circuit system of the types shown and described herein. For example, in some embodiments, at least a portion of the first electronic circuit system can be disposed on the housing of the medicament delivery device. In other embodiments, at least a portion of the first electronic circuit system can be disposed on a portion of the medicament delivery device that is removably coupled to the housing of the medicament delivery device (e.g., a removable protective sheath, a removable safety lock or the like). In some embodiments, for example, a medicament delivery device can include a protective sheath that includes a first portion of the first electronic circuit system, and a housing that includes a second portion of the first electronic circuit system. In such embodiments, the first portion of the first electronic circuit system can include a processor configured to control the second portion of the first electronic circuit system and/or a battery configured to provide power to the second portion of the first electronic circuit system. Similarly, the second portion of the first electronic circuit system can include a processor configured to control the first portion of the first electronic circuit system and/or a battery configured to provide power to the first portion of the first electronic circuit system.

A second electronic signal is then output from a second electronic circuit system, 16. The second electronic signal is associated with the first electronic signal. Similarly stated, the second electronic circuit system outputs the second electronic signal in response to the first electronic signal. In some embodiments, for example, the second electronic signal can include information associated with and/or included within the first electronic signal, such as, for example, the date and time when the first electronic signal was received by the second electronic circuit system. In other embodiments, the second electronic signal can include information identifying the contents of the medicament delivery device (e.g., the amount and type of medicament contained therein), an expiration date of the medicament delivery device, or the like.

As described above, the second electronic signal can be any suitable electronic signal that can be produced and/or output by the second electronic circuit system. For example, in some embodiments, the second electronic signal can be output to an audio output device and/or a video output device. In other embodiments, the second electronic signal can be a communications signal (e.g., a radio frequency signal) that can be transmitted from the second electronic circuit system to the user's computer, a communications network $N_W$, and/or a remotely located device.

Figure 25:
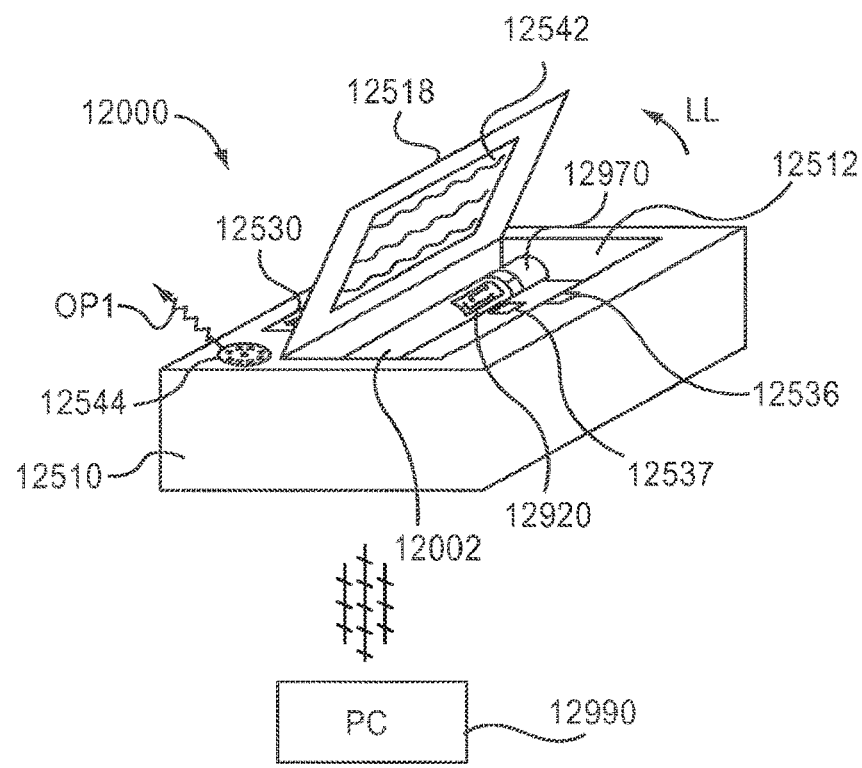

FIGS. 24-27 show a medical system 12000 according to an embodiment of the invention, in a first configuration, a second configuration, a third configuration, and a fourth configuration, respectively. The medical system 12000 includes a medicament delivery device 12002 (see e.g., FIG. 25) and a compliance monitoring device 12510. As shown in FIG. 25, the compliance monitoring device 12510 includes a hinged lid 12518, an electronic circuit system 12530, a first switch 12536 and a second switch 12537. Additionally, the compliance monitoring device 12510 defines an internal region 12512 within which the medicament delivery device 12002 can be contained.

The electronic circuit system 12530 of the compliance monitoring device 12510 is configured to produce and/or output one or more electronic outputs and/or electronic signals of the type described above. As described in more detail below, the electronic circuit system 12530 includes a speaker 12544 and an LCD screen 12542. Moreover, similar to the container 3010 shown and described above with reference to FIGS. 20-22, the electronic circuit system 12530 of the compliance monitoring device 12510 is operatively coupled to a personal computer (PC) 12990. In this manner, as described in more detail herein, the electronic circuit system 12530 of the compliance monitoring device 12510 can transmit information associated with the medical system 12000 to and/or receive information associated with the medical system 12000 from any number of remotely located third party devices (not shown in FIGS. 24-27) via the PC 12990.

Figure 26:
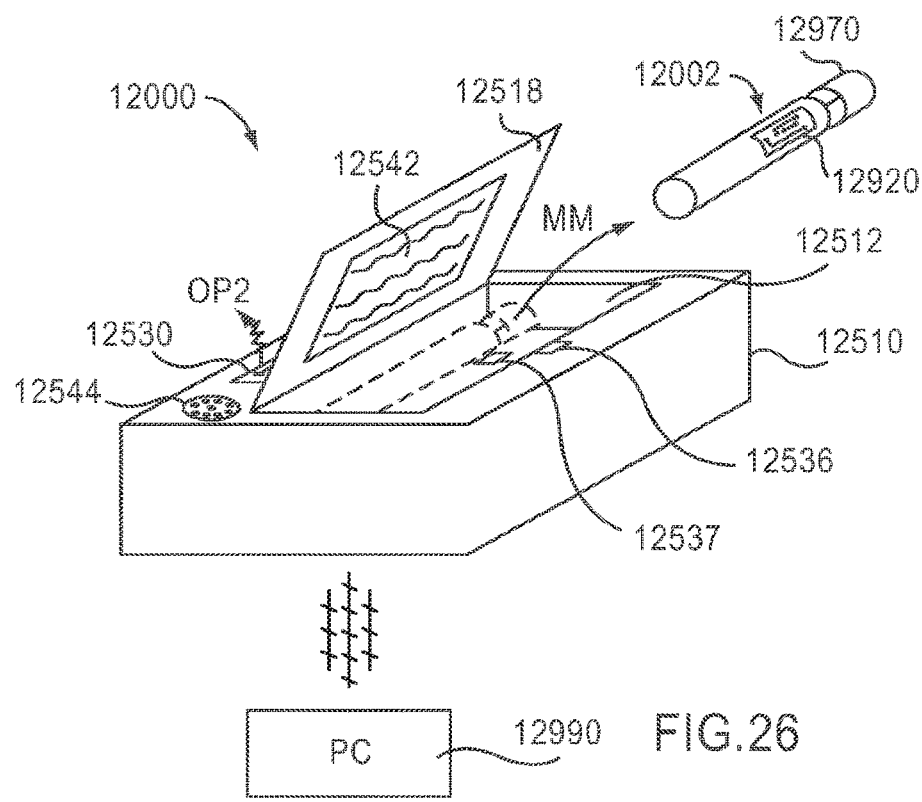
Figure 27:
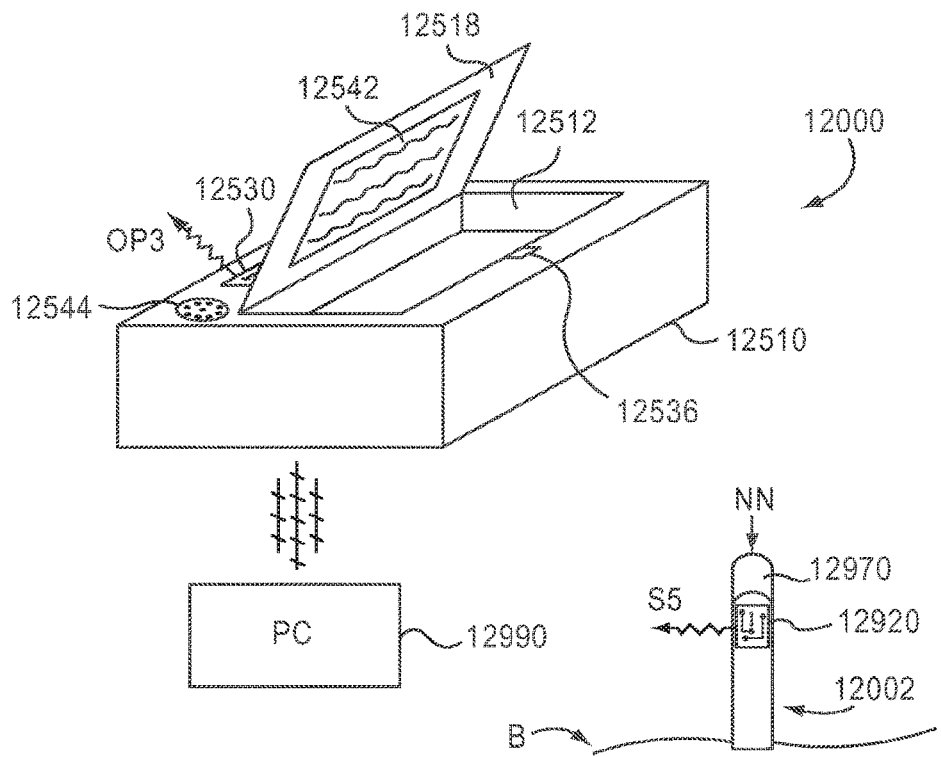

The hinged lid 12518 has a first position (see FIG. 24) and a second position (see FIGS. 25-27). When the hinged lid 12518 is in the first position, the hinged lid 12518 covers the internal region 12512 of the compliance monitoring device 12510. Conversely, when the hinged lid 12518 is in the second position, at least a portion of the internal region 12512 of the compliance monitoring device 12510 is exposed. Said another way, when the hinged lid 12518 is in the second position, the medicament delivery device 12002 can be removed from the internal region 12512 of the compliance monitoring device 12510.

The electronic circuit system 12530 of the compliance monitoring device 12510 is operatively coupled to the first switch 12536 and the second switch 12537. The first switch 12536 is configured to move between a first state (e.g., closed) and a second state (e.g., opened) when the hinged lid 12518 moves between its first position and its second position, as indicated by arrow LL in FIG. 25. The electronic circuit system 12530 is configured to produce and/or output a first output OP1 via the speaker 12544 when the first switch 12536 is moved from its first state to its second state. The first output OP1 can be a recorded speech output associated with an identification of the medicament delivery device 12002, an identification of patient symptoms (e.g., instructions for assessing the physical condition of the patient), an instruction for using the medicament delivery device 12002, an instruction for using the compliance monitoring device 12510, a message guiding the patient in procedures for adhering to the prescribed medication regimen, a status of the compliance monitoring device 12510 and/or a status of the patient's compliance with the prescribed medication regimen. For example, in some embodiments the first output OP1 can state "YOU HAVE ACTIVATED THE ALLERGIC REACTION RESPONSE KIT. THIS KIT INCLUDES AN AUTO-INJECTOR CONTAINING EPINEPHRINE. BEFORE USING THIS AUTO-INJECTOR, PLEASE ENSURE THAT THE PATIENT IS EXHIBITING THE FOLLOWING SYMPTOMS . . . " In other embodiments, the first output OP1 can state "YOUR NEXT DOSAGE IS NOT DUE UNTIL XX P.M. PLEASE DO NOT ADMINISTER THE DOSE AT THIS TIME." In yet other embodiments, the first output OP1 can state "BECAUSE THE MEDICAMENT HAS BEEN REFRIGERATED FOR STORAGE, THE MEDICAMENT IS CURRENTLY TOO COLD. THE CURRENT TEMPERATURE OF THE MEDICAMENT IS XX DEGREES, PLEASE LEAVE THE MEDICAMENT AT ROOM TEMPERATURE FOR XX MINUTES BEFORE ADMINISTERING THE DOSE." In yet other embodiments, the first output OP1 can state "THIS IS THE LAST DOSE IN THE CURRENT PRESCRIPTION. AFTER ADMINISTERING THIS DOSE, PLEASE CONTACT YOUR HEALTH CARE PROVIDER FOR FURTHER ADVICE." Although described as an audible output, in other embodiments, the first output OP1 can be any type of electronic output as described herein.

The second switch 12537 is configured to move between a first state (e.g., closed) and a second state (e.g., opened) when the medicament delivery device 12002 is removed from the internal region 12512 of the compliance monitoring device 12510, as indicated by the arrow MM in FIG. 26. The electronic circuit system 12530 of the compliance monitoring device 12510 is configured to output a second output OP2 via the speaker 12544 and/or the LCD screen 12542 when the second switch 12537 is moved from its first state to its second state. The second output OP2 can be, for example, a recorded speech output and/or a video output associated with an identification of the medicament delivery device 12002, an identification of patient symptoms (e.g., instructions for assessing the physical condition of the patient), an instruction for using the medicament delivery device 12002, an instruction for using the compliance monitoring device 12510, a status of the compliance monitoring device 12510 and/or a status of the patient's compliance with the prescribed medication regimen. For example, in some embodiments the second output OP2 can be an audiovisual output via both the speaker 12544 and the LCD screen 12542 providing step-by-step instructions for using the medicament delivery device 12002 and/or the compliance monitoring device 12510.

The medicament delivery device 12002 can be any device for delivering a medicament into a body, of the types shown and described herein. The medicament delivery device 12002 includes an actuator 12970 and an electronic circuit system 12920. The actuator 12970 is movable between a first position (FIG. 26) and a second position (FIG. 27). When the actuator 12970 is moved from the first position to the second position, the actuator 12970 initiates the delivery of the medicament into the body. In some embodiments, the actuator 12970 can be similar to the base 4520 shown and described above with reference to FIGS. 5-16.

The electronic circuit system 12920 of the medicament delivery device 12002 is configured to output at least an electronic signal S5 (see FIG. 27) when the actuator 12970 is moved from the first position to the second position. The electronic circuit system 12920 of the medicament delivery device 12002 can include any suitable electronic components operatively coupled to produce and/or output the electronic signal S5 and/or to perform the functions described herein. In some embodiments, for example, the electronic circuit system 12920 of the medicament delivery device 3002 can be similar to the electronic circuit system 4920 shown and described above with reference to FIGS. 5-16.

The medical system 12000 can be used to manage the patient's medication regimen and/or track the patient's compliance in following the prescribed medication regimen in a similar manner as described above with reference to the medical system 3000. To move the medical system 12000 from a storage configuration (FIG. 24) to a pre-delivery configuration (FIG. 26), the hinged lid 12518 is moved, as shown by the arrow LL in FIG. 25, and the medicament delivery device 12002 is removed from the compliance monitoring device 12510, as shown by the arrow MM in FIG. 26. As described above, the movement of the hinged lid 12518 produces an input to the electronic circuit system 12530 via the first switch 12536. The input from the first switch 12536 triggers the electronic circuit system 12530 to produce and/or output the first output OP1, as discussed above. Similarly, when the medicament delivery device 12002 is removed from the internal region 12512 of the compliance monitoring device 12510, the second switch 12537 produces an input to the electronic circuit system 12530. The input from the second switch 12537 triggers the electronic circuit system 12530 to produce and/or output the second output OP2, as discussed above.

To administer the medication (i.e., to move the medical system 12000 to a post-delivery configuration, as shown in FIG. 27), the medicament delivery device 12002 is first positioned adjacent a portion of a body B of a patient. Although the portion of the body B is shown as being a surface, such as, for example, the skin, in other embodiments, the portion of the body B can be any suitable location for delivering the medicament (e.g., the mouth, the nasal passages, or the like). The medicament delivery device 12002 is then actuated by moving the actuator 12970 from the first position (FIG. 26) to the second position (FIG. 27), as shown by the arrow NN in FIG. 27.

When the actuator 12970 is moved from the first position to the second position, the electronic circuit system 12920 of the medicament delivery device 12002 outputs the electronic signal S5. Said another way, when actuator 12970 is moved from the first position to the second position, the actuator 12970 actuates the electronic circuit system 12920 of the medicament delivery device 12002 such that the electronic circuit system 12920 produces and/or outputs the electronic signal S5. The actuator 12970 can actuate the electronic circuit system 12920 in any manner as described herein. The electronic signal S5 can be any suitable communications signal, as described herein.

In a similar manner as described above with reference to the medical system 3000, the electronic signal S5 is received by the electronic circuit system 12530 of the compliance monitoring device 12510, which then produces the third electronic output OP3. The third electronic output OP3 is associated with the electronic signal S5. For example, the third electronic output OP3 can include a date and time stamp documenting when the electronic signal S5 was received. In some embodiments, the third electronic output OP3 can include information included within the electronic signal S5, such as a unique identification of the medicament delivery device 12002. In this manner, the electronic circuit system 12530 of the compliance monitoring device 12510 and the electronic circuit system 12920 of the medicament delivery device 12002 can cooperatively monitor the patient's compliance in using the medicament delivery device 12002. As described above, in some embodiments, the third electronic output OP3 includes a communications signal (e.g., a radio frequency signal) that can be transmitted from the electronic circuit system 12530 of the of the compliance monitoring device 12510 to the PC 12990.

Although the electronic circuit system 12530 of the compliance monitoring device 12510 is shown and described as receiving the electronic signal S5 from medicament delivery device 12002 in real-time when the medicament delivery device 12002 is actuated, in other embodiments, the electronic signal S5 can be received by the electronic circuit system 12530 of the compliance monitoring device 12510 at any time after the medicament delivery device 12002 has been actuated. For example, in some embodiments, the electronic signal S5 can be a short-range radio frequency signal having a range of approximately 100 meters or less. Accordingly, in certain instances, the medicament delivery device 12002 may be actuated when the medicament delivery device 12002 is out of transmission range for transmitting the electronic signal S5 to the compliance monitoring device 12510. In some such embodiments, for example, the electronic circuit system 12530 of the compliance monitoring device 12510 and/or the electronic circuit system 12970 of the medicament delivery device 12002 can be configured to detect when the medicament delivery device is in range (e.g., when the patient returns home) and then transmit the electronic signal S5. In other such embodiments, the electronic circuit system 12530 of the compliance monitoring device 12510 can include a scanner (e.g., an optical scanner or the like; not shown in FIGS. 24-27) such that the patient can scan the medicament delivery device 12002 when in proximity to the compliance monitoring device 12510 such that the electronic circuit system 12970 of the medicament delivery device 12002 can transmit the electronic signal S5 to the electronic circuit system 12530 of the compliance monitoring device 12510.

Figure 28:
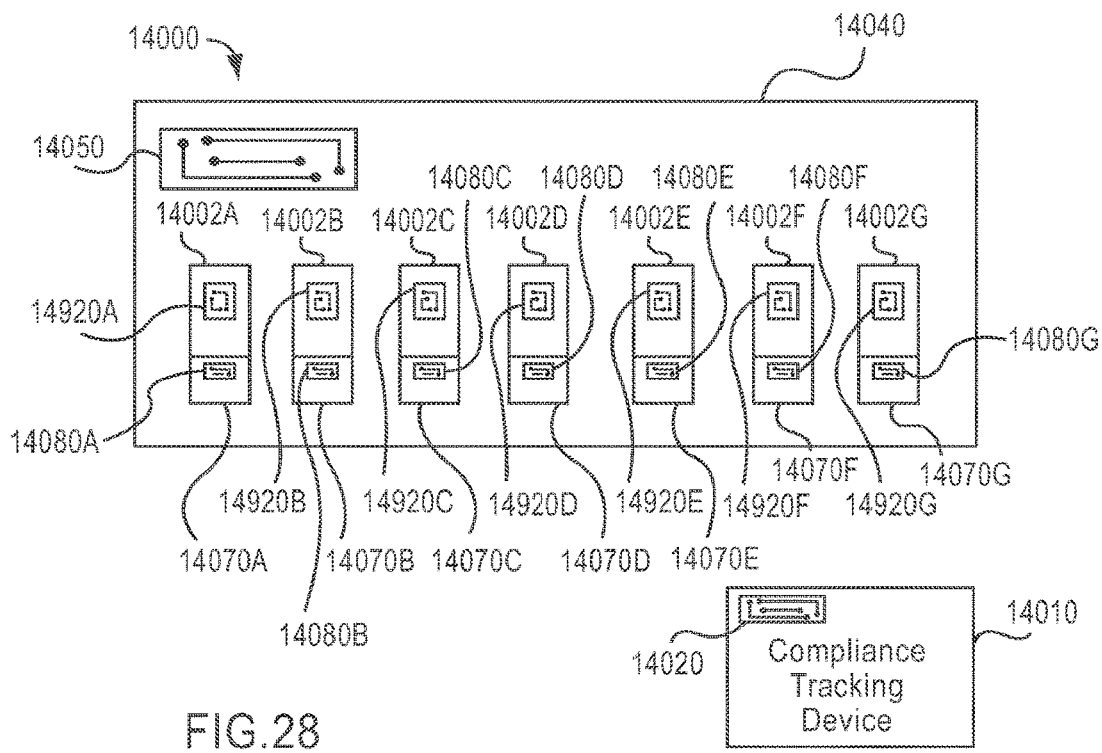
FIG. 28 is a schematic illustration of a medical system according to an embodiment of the invention.

Although the medical system 12000 is shown and described above as including one medicament delivery device 12002, in other embodiments, a medical system can include multiple medicament delivery devices. Such a system can be used, for example, as a part of a chronic-care medication regimen. For example, a medical system having multiple medicament delivery devices can be used to manage insulin delivery or the delivery of other medicaments (e.g., to treat Multiple Sclerosis, anemia, Rheumatoid Arthritis, Osteoporosis or the like), which can require daily, weekly and/or monthly injections. FIG. 28 is a schematic illustration of a medical system 14000 according to an embodiment of the invention, that includes multiple medical injectors 14002A-14002G. Because the medical system 14000 is similar in many respects to the medical systems shown and described above, the medical system 14000 is shown in only one configuration. The medical system 14000 includes a container 14040, a compliance tracking device 14010 and multiple medical injectors 14002A-14002G. The compliance tracking device 14010 is similar to the compliance tracking device 12010 shown and described above, except that the medical injectors 14002A-14002G need not be disposed within the compliance tracking device 14010.

The compliance tracking device 14010 includes an electronic circuit system 14020, which can be operatively coupled to a computer, a communications network, or the like, as discussed above.

The medical injectors 14002A-14002G can be, for example, single-use, disposable auto-injectors of the types shown and described herein. In some embodiments, the medical injectors 14002A-14002G can include the same dosage of a medicament, and can be prescribed as a part of a chronic-care medicament regimen, clinical trial, or the like. In other embodiments, the medical injectors 14002A-14002G can include the different dosages and/or different medicament compositions.

Each of the medical injectors 14002A-14002G includes a removable cover 14070A-14070G, a first electronic circuit system 14920A-14920G and a second electronic circuit system 14080A-14080G. The removable covers 14070A-14070G can be, for example, protective needle guards, safety locks, or any other protective device. As shown in FIG. 28, each of the second electronic circuit systems 14080A-14080G is coupled to the corresponding removable cover 14070A-14070G. The first electronic circuit systems 14920A-14920G are coupled to the medicament injectors 14002A-14002G, as shown and described above. The first electronic circuit systems 14920A-14920G and the second electronic circuit systems 14080A-14080G can each be similar in function and design to the electronic circuit systems shown and described above. By utilizing two electronic circuit systems on each medical injector (e.g., the first electronic circuit system 14920A and the second electronic circuit system 14080A), the first electronic circuit systems 14920A-14920G and the second electronic circuit systems 14080A-14080G can be cooperatively designed to provide the desired functionality, as described above. In other embodiments, however, each medical injector 14002A-14002G can include only a single electronic circuit system.

The container 14040 includes an electronic circuit system 14050, and is configured to receive and/or hold at least a portion of each of the medical injectors 14002A-14002G. For example, in some embodiments, the container 14040 can include multiple recessed portions, retainers, and/or any other suitable structure that matingly receives at least a portion of each medical injector 14002A-14002G. In some embodiments, the medical injectors 14002A-14002G can be arranged within the container 14040 in a specific order and/or orientation. Such an arrangement can be used, for example, to facilitate the medication regimen. Said another way, in some embodiments, the medical injectors 14002A-14002G can be arranged in the order reflecting the order in which they are to be administered by the user. In other embodiments, however, the medical injectors 14002A-14002G can be arranged within the container 14040 randomly. Moreover, in some embodiments, the container 14040 can be configured to receive different types of medical injectors. This can allow the container 14040 to be used in both current and future therapeutic regimens for a patient.

The electronic circuit system 14050 of the container 14040 can be similar to the electronic circuit systems shown and described above, and can, for example, transmit and/or receive electronic signals from the electronic circuit system 14020 of the compliance monitor, the first electronic circuit systems 14920A-14920G and/or the second electronic circuit systems 14080A-14080G. In some embodiments, the electronic circuit system 14050 of the container 14040 can include an RFID tag encoded with information associated with the medical injectors 14002A-14002G, the medication regimen or the like. In this manner, the electronic signals output and/or produced by the electronic circuit system 14050 of the container 14040 can include information characterizing the medical injectors 14002A-14002G and/or the medication regimen. Such information can include, for example, the number of medical injectors, the amount and type of medicament contained within each medical injector, an expiration date of each medical injector or the like. In this manner, when a patient receives a container 14040 for use, the electronic circuit system 14050 of the container 14040 can be electronically encoded with information that can received by the compliance tracking device 14010. Accordingly, when the patient electronically couples the container 14040 to the compliance tracking device 14010 (e.g., by wired connection or a wireless connection), the container 14040 and the compliance tracking device 14010 can electronically and/or automatically update the patient compliance data associated with the medication regimen.

In use, a container 14040 can include the medical injectors required to administer a predetermined medication regimen. For example, in some embodiments the container 14040 can be "loaded" by a pharmacy and delivered to the patient. The container 14040 is then operatively coupled to the compliance tracking device 14010. Said another way, the electronic circuit system 14050 of the container 14040 can be electronically coupled to the electronic circuit system 14020 of the compliance tracking device 14010. In this manner, the electronic information included within the electronic circuit system 14050 of the container 14040 can be received by the electronic circuit system 14020 of the compliance tracking device 14010 to initialize and/or update a compliance tracking schedule associated with the patient's medication regimen.

The compliance tracking device 14010 can then produce and/or output one or more electronic outputs, as described above. Such outputs can include, for example, visual and/or audible outputs reminding the patient of the date and time of the next dosage, indicating the expiration date of the medicament delivery device, providing instructions in the use of the medicament delivery device, a status of the compliance tracking device 14010, a use instruction associated with the compliance tracking device 14010 and/or the like.

To administer a dosage, the patient removes the appropriate medical injector (e.g., medical injector 14002A) from the container 14040. In some embodiments, the removal of the medical injector 14002A triggers the electronic circuit system 14050, the first electronic circuit system 14920A and/or the second electronic circuit system 14080A to output an electronic signal, as described above. Similarly, when the patient removes the removable cover 14070A to place the medical injector 14002A in a "ready" position, the first electronic circuit system 14920A and/or the second electronic circuit system 14080A can output an electronic signal, as described above. Finally, when the patient actuates the medical injector 14002A, the first electronic circuit system 14920A and/or the second electronic circuit system 14080A can output an electronic signal, as described above. In this manner, the medical injectors 14002A-14002G, the container 14040 and the compliance tracking device 14010 can cooperatively monitor the patient's compliance in adhering to the medication regimen.

Figure 31:
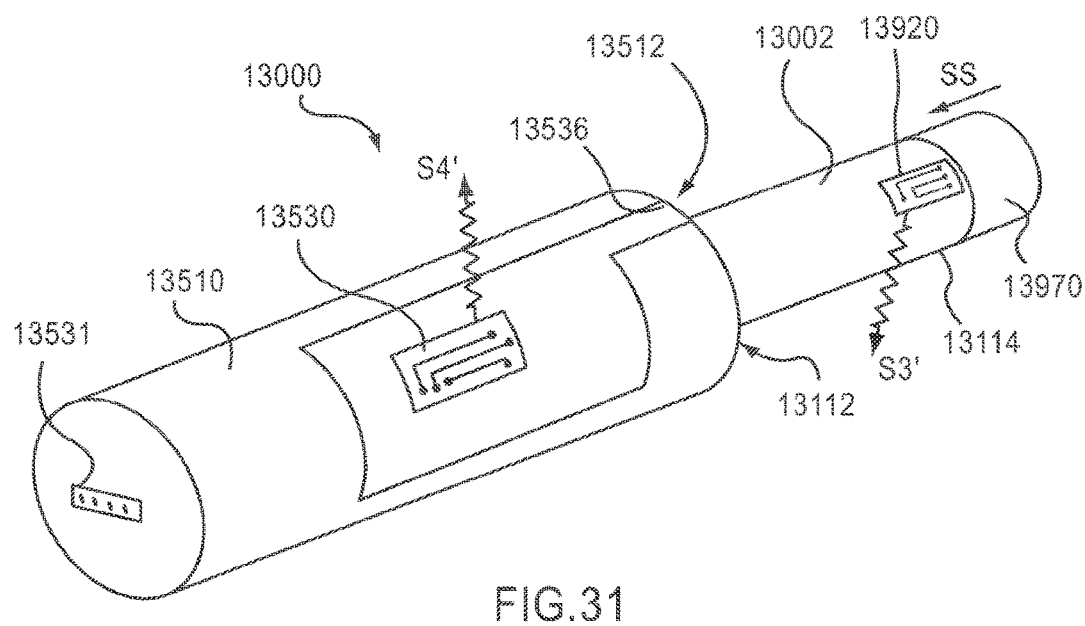

Although the medical system 3000 is shown and described above as including a medicament delivery device 3002 that is removed from a container 3010 during the medicament delivery event, in other embodiments, a medical system can include a medicament delivery device that remains at least partially disposed within the container during a medicament delivery event. For example, FIGS. 29-31 show a medical system 13000 according to an embodiment of the invention in a first configuration, a second configuration and a third configuration, respectively. The medical system 13000 includes a medicament delivery device 13002 and a container 13510. As shown in FIGS. 30 and 31, the medicament delivery device 13002 has a proximal end portion 13112 and a distal end portion 13114. The distal end portion 13114 includes an actuator 13970 configured to initiate the delivery of medicament from the medicament delivery device 13002, as described above. The medicament delivery device 13002 also includes an electronic circuit system 13920. The electronic circuit system 13920 of the medicament delivery device 13002 can include similar components and can have similar functionality as any of the electronic circuit systems described herein.

The container 13510 defines an internal region 13512 (see FIGS. 30 and 31) and a cover 13518 (FIG. 29). The container 13510 also includes an electronic circuit system 13530. As shown in FIGS. 30 and 31, the proximal end portion 13112 of the medicament delivery device 13002 is disposed within the internal region 13512 of the container 13510. In some embodiments, the internal region 13512 of the container 13510 can include a recessed portion, a retainer, and/or any other suitable structure that matingly receives at least a portion of the proximal end portion 13112 of the medicament delivery device 13002. In this manner, the medicament delivery device 13002 can be maintained within the container 13510 during use.

The cover 13518 is removably coupled to the container 13510. When the cover 13518 is coupled to the container 13510, the distal end portion 13114 of the medicament delivery device 13002 is within the cover 13518. In this manner, the cover 13518 can protect the medicament delivery device 13002 and/or prevent the inadvertent use thereof. In some embodiments, the cover 13518 can be coupled to the container 13510 via an interference fit, a threaded coupling, a mating protrusion and recess coupling, or the like.

The electronic circuit system 13530 of the container 13510 includes at least a switch 13536 and a communications port 13531. The switch 13536, which can be similar to the switch 12536 shown and described above, produces an electronic input to the electronic circuit system 13530 when the cover 13518 is removed from the container 13510. Said another way, the electronic circuit system 13530 is configured to produce and/or output one more electronic signals when the switch 13536 changes states in response to the cover 13518 being removed from the container 13510. For example, as shown in FIG. 30, in some embodiments, the electronic circuit system 13530 is configured to produce and/or output a first electronic signal S2' when the switch 13536 changes states (e.g., when the cover 13518 is removed from the container 13510). The first electronic signal S2' can be similar to any of the electronic signals and/or outputs described herein.

The communications port 13531 can be any suitable port for operatively coupling the electronic circuit system 13530 of the container 13510 to a remote device, such as a compliance monitoring device, a PC, a battery charger, or the like (not shown in FIGS. 29-31). The remote device can be coupled to the communications port 13531 via an electronic cable 13532 configured to be matingly coupled to the communications port 13531. In some embodiments, the internal region 13512 of the container 13510 can include a port and/or electronic coupling (not shown in FIGS. 29-31) such that the electronic circuit system 13920 of the medicament delivery device 13002 can be operatively coupled to the electronic circuit system 13530 of the container 13510 when the proximal end portion 13112 of the medicament delivery device 13002 is disposed within the container 13510. In this manner, the container 13510 can function as a docking station for the medicament delivery device 13002. Said another way, the electronic circuit system 13920 of the medicament delivery device 13002 can be powered by and/or use certain components of the electronic circuit system 13530 of the container 13510. Such an arrangement can facilitate the use of a low-cost electronic circuit system on a single-use, disposable medicament delivery device.

To move the medical system 13000 from the first configuration to the second configuration (i.e., a "pre-delivery" configuration), the cover 13518 is removed from the container 13510, as shown by the arrow RR in FIG. 29. When the cover 13518 is removed from the container 13510, the electronic circuit system 13530 of the container 13510 produces the first electronic signal S2'. The first electronic signal S2' can be associated with the prescribed medication regimen (including, for example, compliance data), an identification of the medicament delivery device 13002, a status of the medicament delivery device 13002, a use instruction associated with the medicament delivery device 13002, a status of the container 13510, a use instruction associated with the container 13510 and/or the like. In some embodiments, for example, the first electronic signal S2' can include a visual output, an audible output and/or a haptic output that instructs and/or provides cues to a user in the use of the container 13510 to track the patient's compliance. In other embodiments, the first electronic signal S2' can include a communications signal that can be transmitted via the port 15531 and/or by wireless transmission to a remote device (not shown in FIGS. 29-31).

To move the medical system 13000 from the second configuration to the third configuration (i.e., a "post-delivery" configuration), the medicament delivery device 13002 is actuated by moving the actuator 13970 as shown by the arrow SS in FIG. 31. The patient can move the actuator 13970, for example, by gripping the container 13510 and pressing the distal end portion 13114 of the medicament delivery device 13002 against the body. When the actuator 13970 is moved from the first position to the second position, actuation of the medicament delivery device is initiated. Moreover, when the actuator 3970 is moved, the electronic circuit system 13920 of the medicament delivery device 13002 outputs the second electronic signal S3'.

The second electronic signal S3' is received by the electronic circuit system 13530 of the container 13510, which then produces the third electronic signal S4'. As described above, the third electronic signal S4' is associated with the second electronic signal S3'. The electronic signals S3' and S4' can be similar to the electronic signals S3 and S4 described above with reference to FIGS. 20-22. For example, in some embodiments, the electronic signal S3' can include a time stamp associated with the actuation of the medicament delivery device 13002, and the electronic signal S4' can include information associated with the dosage, contents and/or status of the medicament delivery device 13002.

In this manner, the electronic circuit system 13530 of the container 13510 and the electronic circuit system 13920 of the medicament delivery device 13002 can cooperatively monitor the patient's compliance in using the medicament delivery device 13002. By utilizing two electronic circuit systems, the electronic circuit system 13920 and the electronic circuit system 13530 can be cooperatively designed to provide the desired functionality. For example, in some embodiments, the container 13530 can be a reusable compliance tracking device and the medicament delivery device 13002 can be a single-use, disposable device. Upon completion of the injection, the patient can subsequent re-load the container 13510 with next medicament delivery device 13002, as prescribed.

Figure 32:
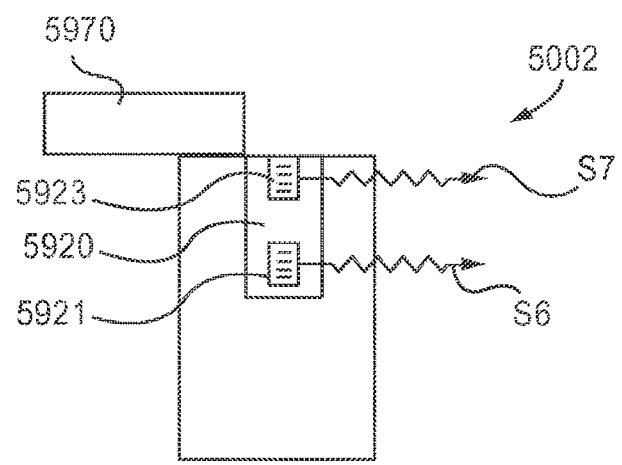
FIGS. 32 and 33 are schematic illustrations of a medicament delivery device according to an embodiment of the invention, in a first configuration and a second configuration, respectively.

Although the electronic circuit systems disposed on the medicament delivery devices are shown and described above as outputting an electronic signal in response to the movement of an actuator, in other embodiments, an electronic circuit system can be configured to prevent, eliminate, reduce and/or alter the transmission of an electronic signal in response to the actuation of the medicament delivery device. For example, FIGS. 32 and 33 are schematic illustrations of a medicament delivery device 5002 according to an embodiment of the invention, in a first configuration and a second configuration, respectively.

The medicament delivery device 5002, which can be medical injector (e.g., an auto-injector, a pen injector, a multiple-use injector, a syringe or the like), an inhaler or the like, includes an actuator 5970 and an electronic circuit system 5920. The actuator 5970 is movable between a first position (FIG. 32) and a second position (FIG. 33). When the actuator 5970 is moved from the first position to the second position, the actuator 5970 initiates the delivery of the medicament into the body. In some embodiments, for example, the actuator 5970 can be configured to release a spring, an energy storage member, or the like, to initiate medicament delivery when the actuator 5970 is moved from the first position to the second position.

The electronic circuit system 5920 includes at least a first RFID tag 5921 and a second RFID tag 5923. The first RFID tag 5921 is configured to output a first electronic signal S6, which can be received by a compliance monitoring device (not shown in FIGS. 32 and 33) of the types shown and described herein. Similarly, the second RFID tag 5923 is configured to output a second electronic signal S7, which can be received by a compliance monitoring device. The first electronic signal S6 has an electronic characteristic (e.g., frequency, amplitude, etc.) that is different from an electronic characteristic of the second electronic signal S7. In this manner, a receiving device (e.g., a compliance monitoring device) can distinguish the first electronic signal S6 from the second electronic signal S7.

Figure 33:
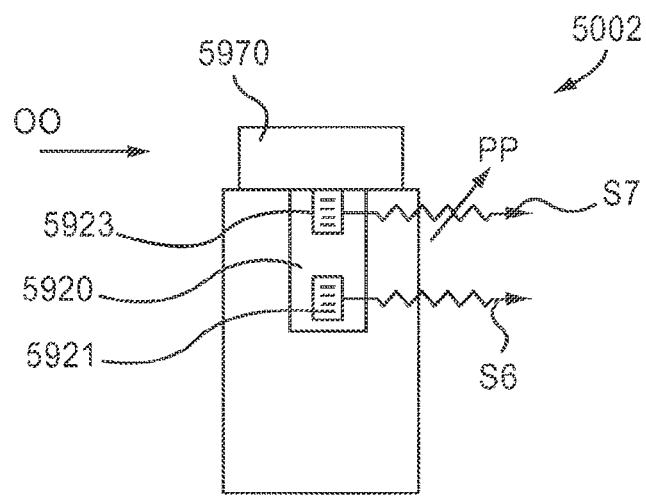

To deliver a dose of medicament, the patient moves the actuator 5970 from the first position to the second position, as shown by the arrow OO in FIG. 33. When the actuator 5970 is moved from the first position to the second position, actuation of the medicament delivery device 5002 is initiated. Said another way, the actuator 5970 is configured to initiate delivery of the medicament when the actuator 5970 is moved from the first position to the second position.

When the actuator 5970 is moved from the first position to the second position, the actuator 5970 eliminates, blocks, and/or alters the second electronic signal S7, as indicated by the arrow PP in FIG. 33. In this manner, the receiving device (e.g., a compliance monitoring device) can receive electronic feedback from the electronic circuit system 5920 corresponding to the actuation of the medicament delivery device 5002. Moreover, the electronic feedback (i.e., the elimination, blockage, and/or alteration of the second electronic signal S7) is provided without requiring the patient to execute any additional steps, other than those required to actuate the medicament delivery device 5002. In this manner, the medicament delivery device 5002 is configured to electronically and/or automatically track the details of its use.

When the actuator 5970 is moved from the first position to the second position, the first electronic signal S6 is not changed. Accordingly, the first electronic signal S6 can function as a validation signal to the receiving device during the actuation of the medicament delivery device 5002. Said another way, the electronic signal S6 can provide feedback associated with the functionality of the electronic circuit system 5920 (e.g., that the first electronic circuit system 5920 is within the transmission range of the receiving device, that the first electronic circuit system is receiving power, etc.).

The actuator 5970 can eliminate, block, and/or alter the second electronic signal S7 by any suitable mechanism. For example, in some embodiments, the movement of the actuator 5970 produces an input that is received by the electronic circuit system 5920, thereby triggering the electronic circuit system 5920 to eliminate, block, and/or alter the second electronic signal S7 output by the second RFID tag 5923. Said another way, in some embodiments, the movement of the actuator 5970 can change the state of a switch (not shown in FIGS. 32 and 33) within the electronic circuit system 5920 thereby triggering the electronic circuit system 5920 to eliminate, block, and/or alter the second electronic signal S7 output by the second RFID tag 5923.

In other embodiments, the movement of the actuator 5970 can disrupt at least a portion of the second RFID tag 5923, thereby eliminating, blocking, and/or altering the second electronic signal S7. For example, in some embodiments, the movement of the actuator 5970 can separate, tear, deform and/or sever a portion of the second RFID tag 5923. In other embodiments, the movement of the actuator 5970 can electronically shield a portion of the second RFID tag 5923, thereby eliminating, blocking, and/or altering the second electronic signal S7. For example, in some embodiments, the actuator 5970 can include a shield portion configured to be disposed about the second RFID tag 5923 when the actuator is in the second position. Such a shield can, for example, block the signal S7 from being output by the second RFID tag 5923.

In other embodiments, the movement of the actuator 5970 can electronically decouple a power source (not shown in FIGS. 32 and 33) from a portion of the electronic circuit system 5920 and/or the second RFID tag 5923. For example, in some embodiments, the actuator 5970 can include a battery isolation tab (not shown in FIGS. 32-33) configured to isolate a battery from a portion of the electronic circuit system 5920. In other embodiments, the actuator 5970 can include a shield portion configured to be disposed about the second RFID tag 5923 when the actuator is in the second position. In this manner, the shield can prevent the second RFID tag 5923 from receiving power from a remote source (e.g., a master RFID tag disposed on the receiving device).

As described herein, the first electronic signal S6 and/or the second electronic signal S7 can include information characterizing the first medicament delivery device 5002. For example, in some embodiments, the first electronic signal S6 and/or the second electronic signal S7 can be associated with the contents of the medicament delivery device 5002 (e.g., the amount and type of medicament contained therein), an expiration date of the medicament delivery device 5002, a dosage of the medicament delivery device 5002 and/or a use instruction associated with the medicament delivery device 5002. In this manner, the receiving device (not shown in FIGS. 32 and 33) can produce the electronic outputs associated with information contained within the first electronic signal S6 and/or the second electronic signal S7. Said another way, this arrangement allows the receiving device to produce an electronic output that is unique to the medicament delivery device 5002.

In some embodiments, the first RFID tag 5921 and/or the second RFID tag 5923 can be passive RFID tags. In such an arrangement, the first RFID tag 5921 and/or the second RFID tag 5923 can be powered remotely by a parent RFID tag, which can be disposed, for example on a compliance monitoring device (not shown in FIGS. 32 and 33). In this manner, the electronic circuit system 5920 of the medicament delivery device 5002 can be devoid of a power supply (e.g., a battery or any other energy storage device). Accordingly, the electronic circuit system 5920 can be a simple, low-cost circuit system 5920 that is suitable for use on a single-use, disposable medicament delivery device.

Figure 34:
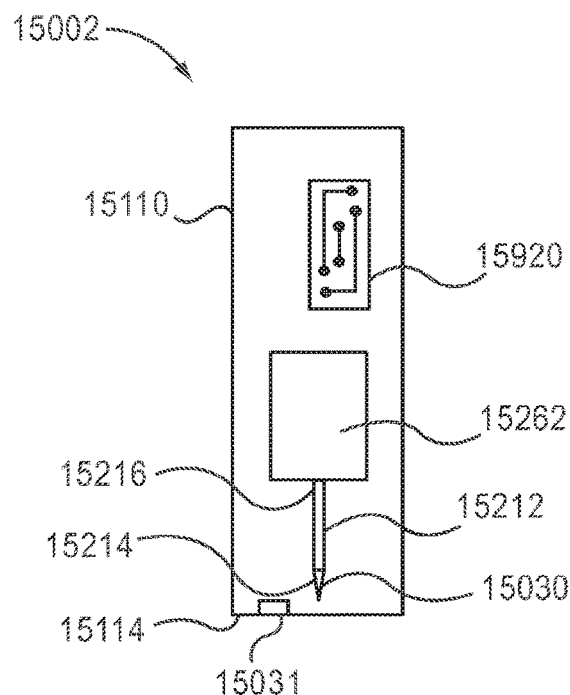
FIGS. 34 and 35 are schematic illustrations of a medicament delivery device according to an embodiment of the invention, in a first configuration and a second configuration, respectively.
Figure 35:
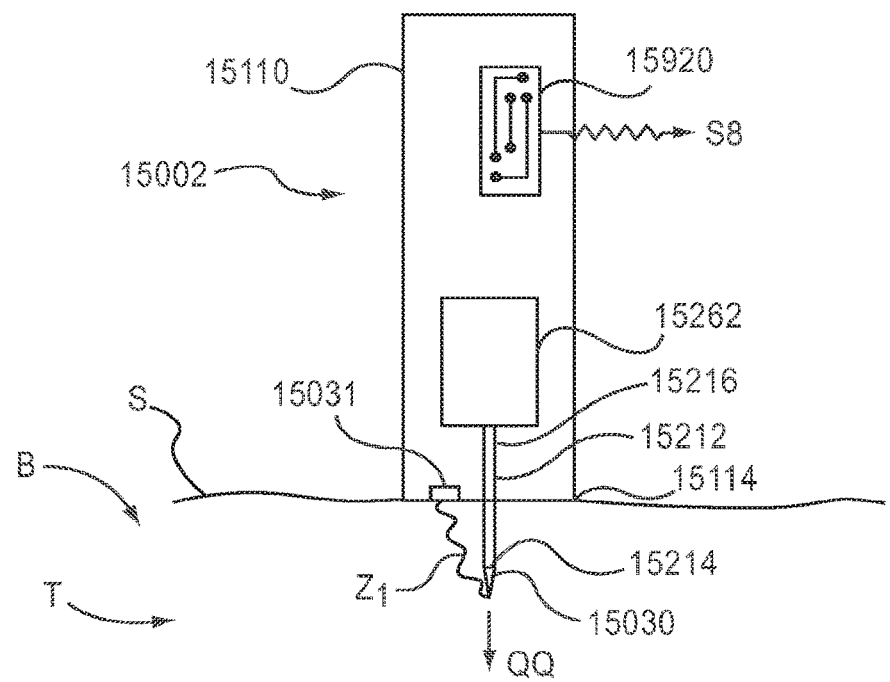

Although the medicament delivery devices are shown and described above as outputting an electronic signal in response to the movement of an actuator, in other embodiments, a medicament delivery device can include any suitable means for providing feedback associated with a dosage administration event. Moreover, although the electronic circuit system 1920 shown and described above with reference to FIGS. 1-3 include a proximity sensor 1974 to provide feedback associated with the validity of an injection event, in other embodiments, a medicament delivery device can include any suitable feedback mechanism for providing feedback associated with the validity of a medicament delivery event. For example, FIGS. 34 and 35 are schematic illustrations of a medical injector 15002 according to an embodiment of the invention, in a first configuration and a second configuration, respectively.

The medical injector 15002, which can be, for example, a single-use, disposable auto-injector of the types shown and described herein, includes a housing 15110, a medicament container 15262, a needle 15212, and an electronic circuit system 15920. The housing 15110 has a proximal end portion 15112 and a distal end portion 15114. The medicament container 15262 is disposed within the housing 15110. Although the medicament container 15262 is shown as being movably disposed within the housing 15110, in other embodiments, the medicament container 15262 can be fixedly disposed within the housing 15110.

The needle 15212 includes a proximal end 15216 and a distal end 15214, and is configured to be in fluid communication with the medicament container 15262. In this manner, the medicament within the medicament container 15262 can be conveyed into a body during an injection event via the needle 15212. The needle 15212 is movably disposed within the housing 15110 between a first position (FIG. 34) and a second position (FIG. 35). When the needle 15212 is in the first position, the distal end 15214 of the needle is disposed within the housing 15110. When the needle 15212 is in the second position, the distal end 15214 of the needle is disposed outside of the housing 15110. Accordingly, when the medical injector 15002 is actuated, the needle 15212 can be moved between the first position and the second position to penetrate the patient's skin S (see FIG. 35) and/or provide a passageway for delivering the medicament into the patient's body B.

The electronic circuit system 15920 is includes at least a first electrode 15030 and a second electrode 15031. The first electrode 15030 is disposed at the distal end 15214 of the needle 15212. The second electrode 15031 is disposed at the distal end portion 15114 of the housing 15110. The electronic circuit system 15920 is configured to output an electronic signal S8 associated with an impedance between the first electrode 15030 and the second electrode 15031.

The electronic signal S8 can be any suitable communications signal, of the types described herein, configured to be received by a compliance monitoring device (not shown in FIGS. 34 and 35) of the types shown and described herein. In this manner, as described in more detail below, the electronic circuit system 15920 can provide electronic and/or automatic feedback associated with the validity and/or administration of an injection event based on the impedance between the first electrode 15030 and the second electrode 15031.

To deliver a dose of medicament, the patient first places the distal end portion 15114 of the housing against the skin S of the body B. In some embodiments, the second electrode 15031 can include a proximity sensor, similar to the proximity sensor 1974 shown and described above with reference to FIGS. 1-3. Accordingly, in such embodiments, the electronic circuit system 15920 can produce one or more electronic outputs indicating that the medical injector 15002 is properly positioned and ready to be actuated. The patient then actuates the medical injector 15002 thereby causing the needle to move from the first position to the second position, as shown by the arrow QQ in FIG. 35. Accordingly, the needle penetrates the patient's skin S to provide a passageway for delivering the medicament into the patient's body B.

During the above-described injection event, the electronic circuit system 15920 is configured to measure the impedance $Z_1$ between the first electrode 15030 and the second electrode 15031. The electronic circuit system 15920 can then produce and/or output the electronic signal S8, which is associated with the impedance $Z_1$. In some embodiments, the electronic signal S8 can be processed, either by the electronic circuit system 15920 or by a compliance monitoring device (not shown in FIGS. 34 and 35) to characterize the validity of the injection event. For example, based on the impedance $Z_1$, the known depth of penetration of the needle 15212 (i.e., the distance between the distal end 15114 of the housing 15110 and the distal end 15214 of the needle 15212), and/or the characteristic impedance of various types of bodily tissue, a compliance monitoring device can determine whether the needle 15212 was disposed within bodily tissue T during the injection event. Said another way, because bodily tissue T has a characteristic impedance that is different from a characteristic impedance of other materials (e.g., a pillow, drywall, clothing materials or the like), the compliance monitoring device can evaluate the validity of the injection event based on the impedance $Z_1$ and/or the known depth of penetration of the needle 15212. Moreover, because different types of bodily tissue can have different characteristic impedance values, in some embodiments, the compliance monitoring device can evaluate whether the injection occurred within fatty tissue, muscle tissue, bone tissue or the like.

Figure 36:
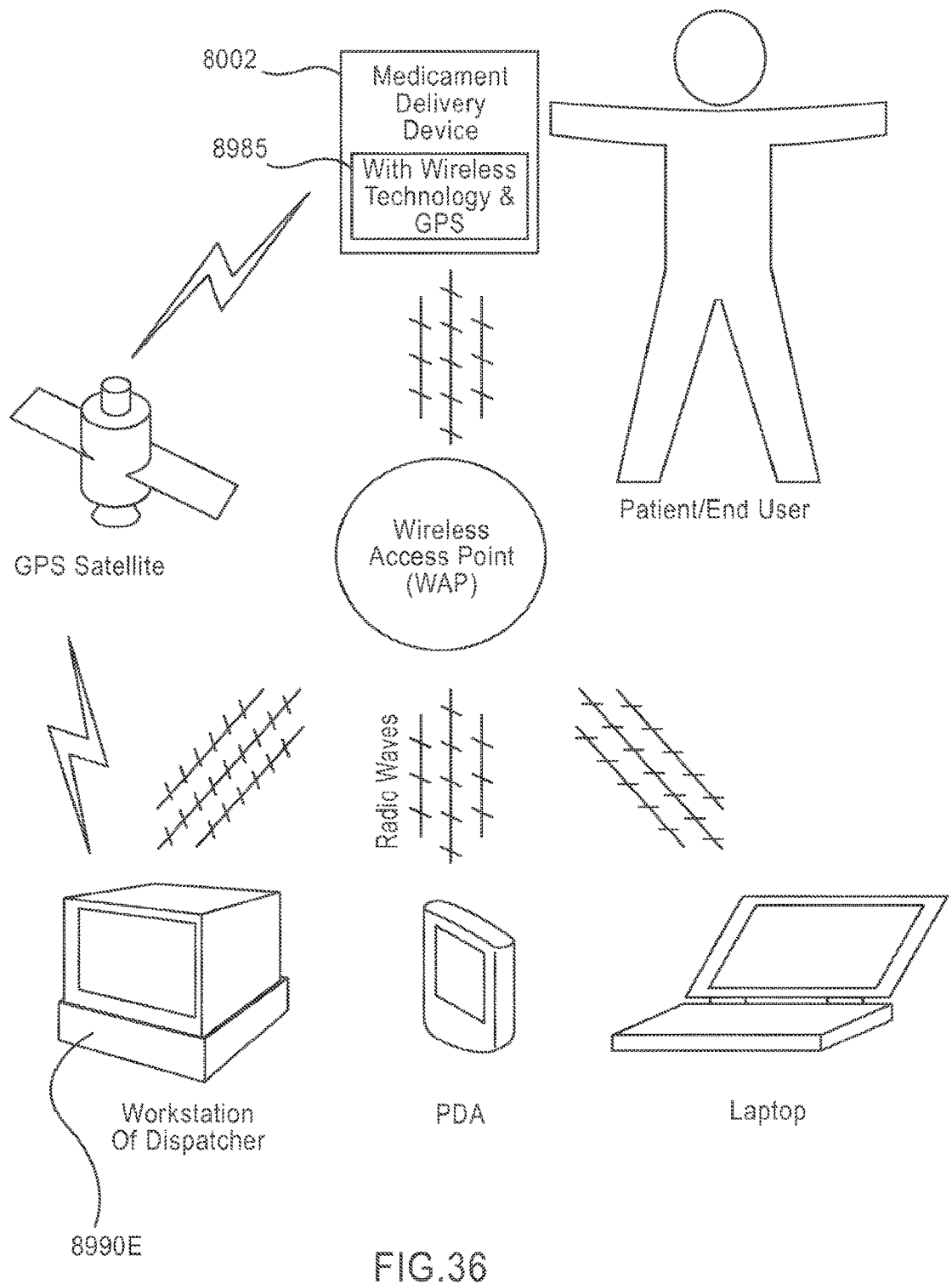
FIG. 36 is a schematic illustration of a medicament delivery device according an embodiment of the invention.

Although the medicament delivery devices, containers and/or compliance tracking devices shown and described above can be configured to send and/or receive electronic signals associated with a wide range of information, in some embodiments, a medicament delivery device, a container and/or a compliance tracking device can include a wireless communications system configured to transmit a location of the medicament delivery device. Such embodiments, can be particularly appropriate, for example, when the medicament delivery device is a single-dose device for use in emergency situations. For example, FIG. 36 is a schematic illustration of a medicament delivery device 8002 according an embodiment of the invention that includes a wireless communications system 8985 configured to communicate electronically directly with an emergency response dispatcher 8990E, via wireless network $N_W$ as described above. Moreover, the wireless communications system 8985 includes a Global System for Mobile Communications and/or Global Positioning System (GPS) enabled feature, which can include a transmitter, a receiver, software, hardware and/or other electronics (not shown in FIG. 36) to transmit the geographical location of the medicament delivery device 8002 to the emergency response dispatcher 8990E. In this manner, when the medicament delivery device 8002 is used, it can be configured to automatically notify emergency response personnel (Emergency Medical Technicians, Fire, Police and the like).

Figure 37:
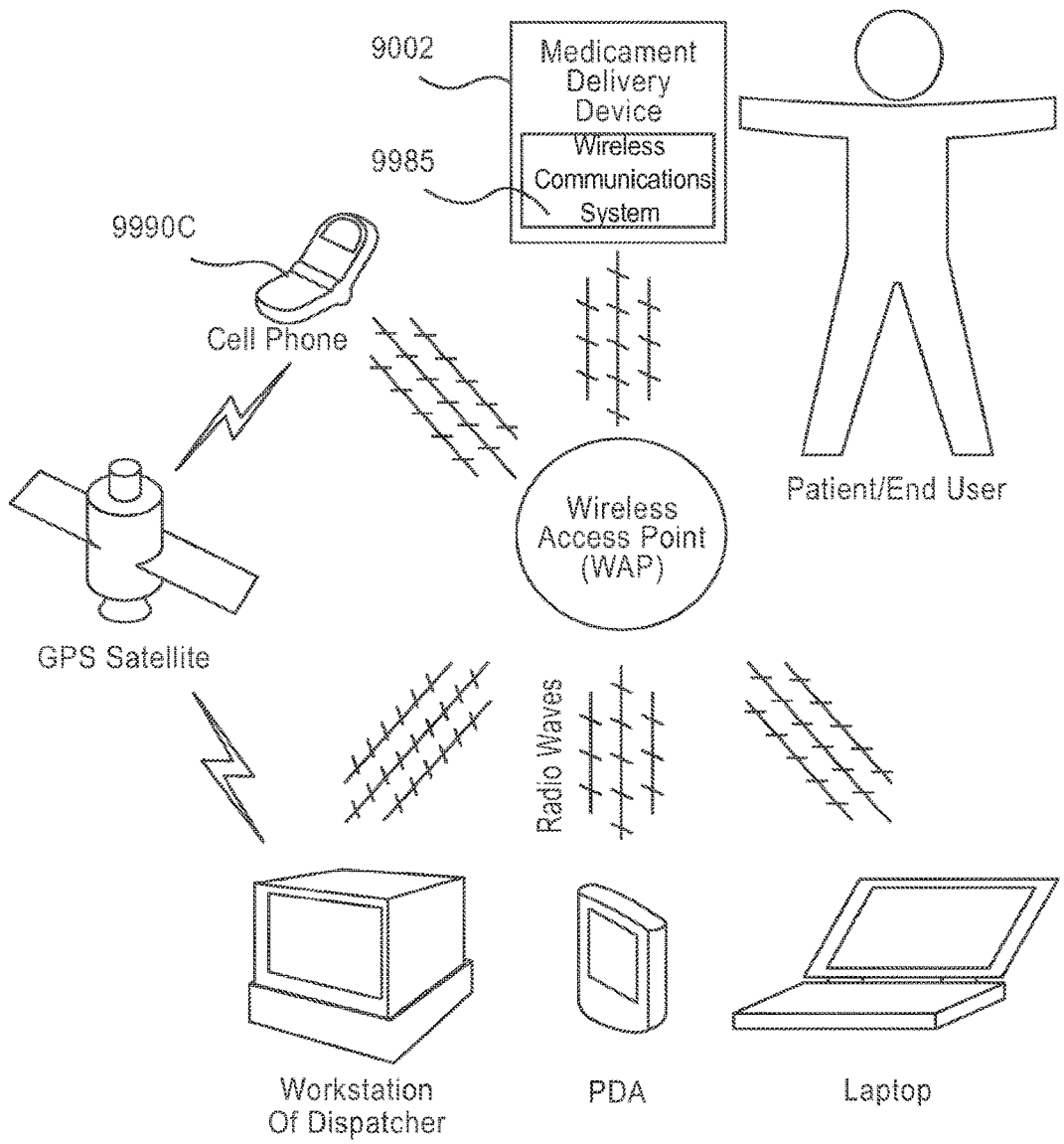
FIG. 37 is a schematic illustration of a medicament delivery device according an embodiment of the invention.

In some embodiments, a wireless communications system can be configured to transmit the geographical location of the medicament delivery device to an emergency response dispatcher via a wireless communications device that is GPS-enabled. For example, FIG. 37 is a schematic illustration of a medicament delivery device 9002 according an embodiment of the invention that includes a wireless communications system 9985 configured to transmit the geographical location of the medicament delivery device 9002 via a wireless communications device 9990C that is GPS-enabled. For example, in some embodiments, the GPS-enabled wireless communications device 9990C can be a cellular phone. In this manner, when the medicament delivery device 9002 is actuated, the wireless communications system 9985 transmits data to the GPS-enabled cell phone 9990C, as described above. The GPS-enabled cell phone 9990C automatically dials an emergency number such as, for example, 911 (emergency dispatcher), and/or sends information associated with the location of the medicament delivery device 9002 and/or the end user location through GPS satellite positioning or network based positioning (using cell phone towers).

Figure 38:
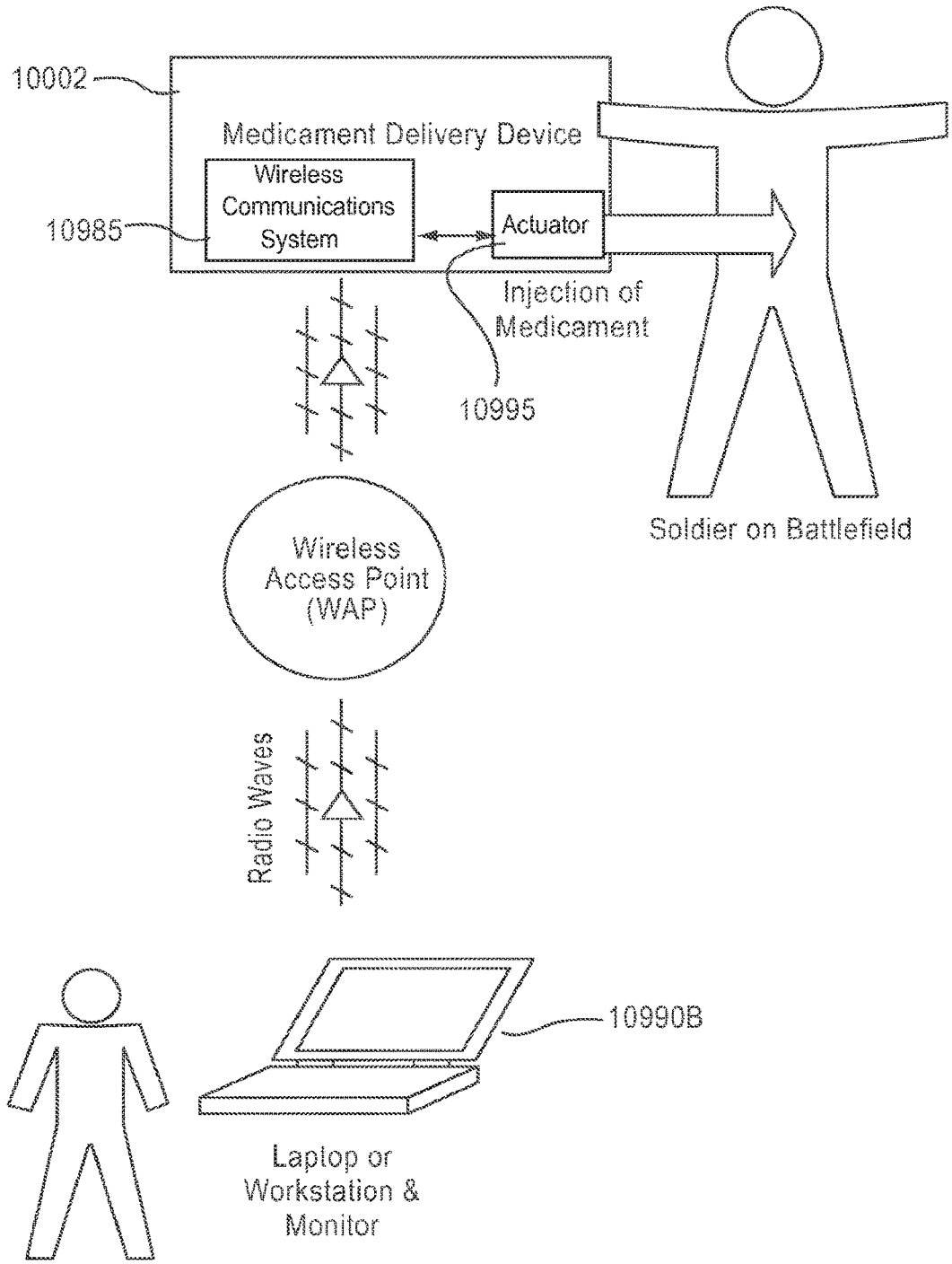
FIG. 38 is a schematic illustration of a medicament delivery device according an embodiment of the invention.

Although the wireless communications systems are shown and described above as being configured to send and/or receive electronic signals associated with a wide range of information, in some embodiments, a wireless communications system can be configured to send and/or receive electronic signals associated with the actuation of a medicament delivery device. More particularly, in some embodiments a wireless communications system can be employed to remotely trigger various functions of a medicament delivery device. For example, FIG. 38 is a schematic illustration of a medicament delivery device 10002 according to an embodiment of the invention that includes such functionality. The medicament delivery device 10002 includes a wireless communications system 10985 and an actuator 10995. The wireless communications system 10985, which can be any suitable system of the type shown and described above is operatively coupled to the actuator 10995. The actuator 10995 can be any suitable mechanism configured to receive an input from the wireless communications system 10985 and, based upon the input, trigger a function of the medicament delivery device 10002. For example, in some embodiments, the actuator 10995 can be integrated into the wireless communications system 10985. The actuator can include, for example, a programmable logic controller (PLC) and/or solenoid that allow the data received via the wireless communications system 10985 to be converted into an action to actuate the medicament delivery device 10002. For example, in some embodiments, as described in more detail herein, the medicament delivery device 10002 can be a gas-powered auto-injector and the actuator 10995 can be configured to move a compressed gas cylinder to actuate the auto-injector.

In use, the remote actuation feature of the medicament delivery device 10002 can be advantageous in circumstances in which the user of such a device is not able to actuate the medicament delivery device 10002 and/or there are no other individuals present to actuate the medicament delivery device 10002. For example, in certain situations, soldiers on a battlefield can carry the medicament delivery device 10002, which can contain one or more medicaments. Such medicaments can be formulated to relieve acute pain (e.g., morphine), mitigate the effects of exposure to a nerve agent and/or prevent seizures secondary to such exposure. The wireless communications system 10985 can be configured to send information to and/or receive information from a battlefield monitor station 10990B located in a secure area. In this manner, the battlefield monitor station 10990B can monitor and/or be in communication with the soldiers on the battlefield.

When a critical incident occurs requiring the use of the medicament delivery device 10002, monitoring personnel can send a signal from the battlefield monitor station 10990B to the medicament delivery device 10002 on the soldier requiring medical attention. The wireless communications system 10985 can receive the signal and process the signal into "activation" data, which can then be transmitted to the actuator 10995 to trigger the actuation of the medicament delivery device 10002 and subsequent delivery of the required medication and/or agent. To ensure that the medicament is delivered in the desired location within the soldier's body, the medicament delivery device 10002 can be placed in a predetermined orientation relative to the soldier. For example, in some embodiments, the medicament delivery device 10002 can be retained within a specific pocket of the soldier's uniform.

Figure 39:
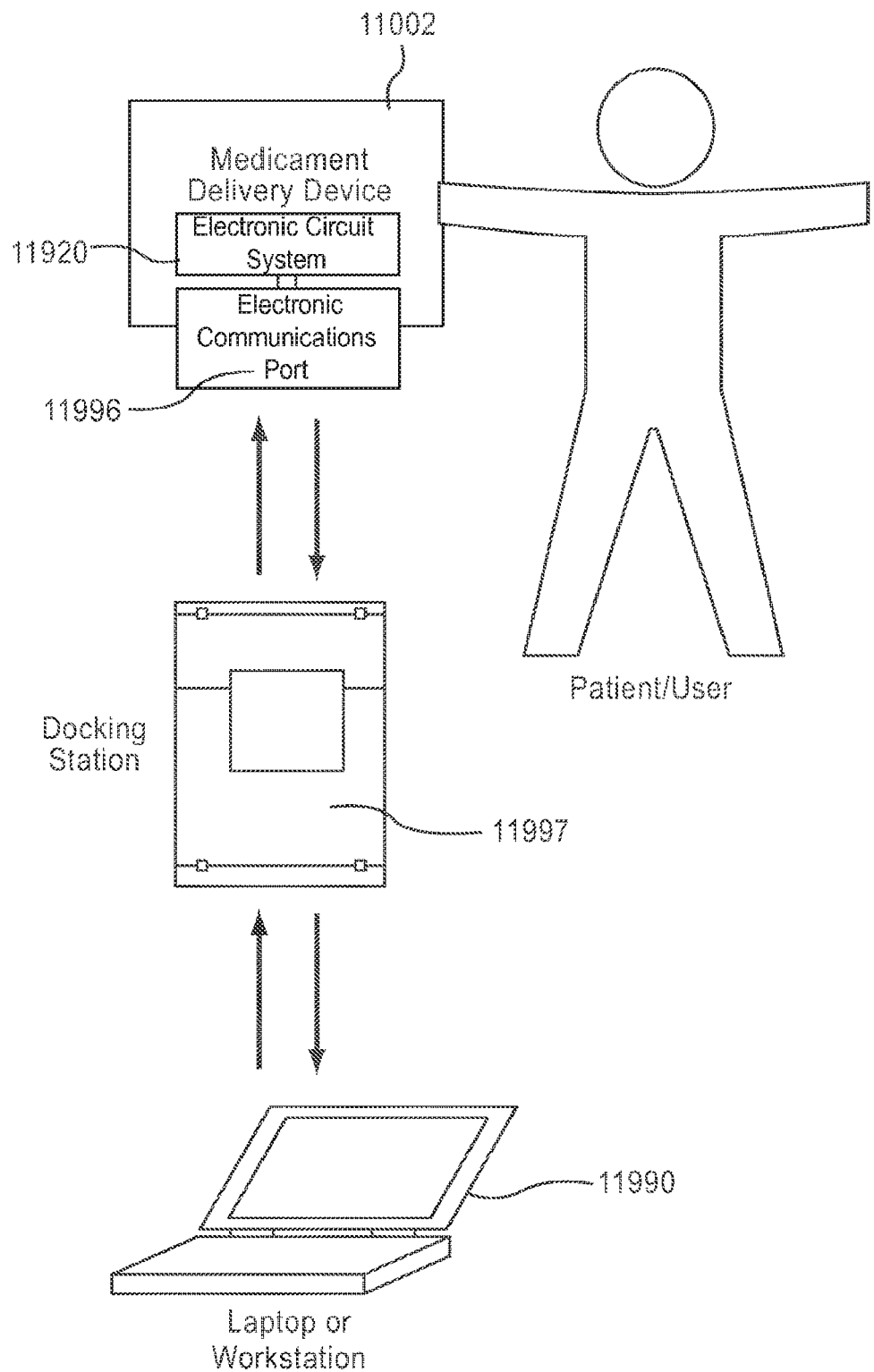
FIG. 39 is a schematic illustration of a medicament delivery device according an embodiment of the invention.

Although the medicament delivery devices have been shown and described above as including a wireless communications system, in some embodiments, a medicament delivery device can send signals to and/or receive signals from various communications devices using a combination of communications networks. For example, in some embodiments, a medicament delivery device can send signals to and/or receive signals from various communications devices using any suitable combination of wireless networks and wired networks. For example, FIG. 39 is a schematic illustration of a medicament delivery device 11002 according to an embodiment of the invention that includes an electronic circuit system 11920 and an electronic communications port 11996. The electronic circuit system 11920 can be any electronic circuit system of the type shown and described herein. For example, the electronic circuit system 11920 can be configured to monitor the status of the medicament delivery device 11002, actuate the medicament delivery device 11002, provide instructions for using the medicament delivery device 11002 or the like.

The electronic communications port 11996 can be any device configured to be operatively coupled to a docking station 11997, which is in turn operatively coupled via a communications network N to a communications device 11990. The docking station 11977 can be, for example, a compliance monitoring device and/or a container of the types shown and described herein. The communications device 11990 can be any communications device of the type shown and described above (e.g., a physician's computer, PDA, an insurer's computer, etc.). In this manner, the electronic circuit system 11920 can send electronic signals to and/or receive electronic signals from the communications device 11990 via the communications network N and the docking station 11997. Moreover, as described herein, the docking station 11997 can include an electronic circuit system (not shown in FIG. 39) to store, process and/or produce electronic signals associated with the use of the medicament delivery device 11002. The communications network N can be any suitable communications network, and can include, for example, wired networks.

In some embodiments, the electronic communications port 11996 can be a serial bus port such as a USB ports or any another method of connecting the electronic circuit system 11920 to the docking station 11997 and/or the communications device 11990 to transfer data. The electronic circuit system 11920, the electronic communications port 11996 and/or the docking station 11997 can include any electronic components (including hardware, firmware and/or software) configured to facilitate electronic communication. For example, in some embodiments, the electronic circuit system 11920, the electronic communications port 11996 and/or the docking station 11997 can include Small Computer System Interface (SCSI and ports), FireWire (or other IEEE 1394 interfaces), data uplink, point-to-point link, fiber optic links, hard drives, pc cards, circuit boards, uplinks, downlinks, docking stations, parallel and bit-serial connections, and the like.

In some embodiments, the use of a wired communication system used as a part of the communications path, can improve the reliability of the information being transferred and could ensure that the information is transferred at the right time and efficiently. For example, after a patient uses the medicament delivery device 11002, the user can place the device into the docking station 11997 connected to the user's workstation (i.e., the communications device 11990 to trigger the transfer of information.

Moreover, as described above, in some embodiments, the communications device 11990 can include software and/or hardware to download the information from the medicament delivery device to the workstation and transmit such information to a third party such as the patient's/user's health care provider (not shown in FIG. 39). As described above, such information could include the location where the device was activated, time of day, dosage and route of administration, frequency of device usage, functionality of the device once used, expiration date of the device, device status, medicament status, and any adverse event experienced by the user following the use of the device. Moreover, as described above, after the information is sent, the user can be notified that the information was sent successfully by receiving electronic confirmation from the communications device 11990 and/or the third party devices. The illustrated communication system also allows the patient to connect to his or her workstation and download information to the medicament delivery device. Such information can include, for example, updated dosing information, updated use instructions, critical software updates, and other information that would be useful to the patient. The medicament delivery device could also connect to other devices other than just a workstation or docking station such as a mini USB drive to transfer the information.

The electronic circuit systems shown and described above can include one or more electronic components operatively coupled to perform the functions described herein. For example, the electronic circuit systems shown and described herein (including those included as a part of the medicament delivery devices, the containers, and the compliance monitoring devices shown and described herein) can be similar to the electronic circuit system 1920 shown and described above with reference to FIG. 3. Although the medical devices shown and described above include one electronic circuit system, in some embodiments, a medical device can include multiple electronic circuit systems configured to perform the functions described herein.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, although the components included in the electronic circuit system 4920 (e.g., the microprocessor 4950, the LEDs 4958A and 4958B or the like) are shown and described as being operatively coupled by electrical conductors 4934, in other embodiments, the components can be operatively coupled without being physically connected. For example, in some embodiments, at least a portion of the components included in an electronic circuit system can be inductively coupled. In other embodiments, at least a portion of the components included in an electronic circuit system can be evanescently coupled.

Although the switches 4972A and 4972B are shown and described as being "tear-through" switches that are monolithically formed from the electrical conductors 4934, in other embodiments, a switch can be formed separately from the electrical conductors 4934. For example, in some embodiments, an electrical circuit system can include a series of first electrical conductors having a first set of characteristics (e.g., the width, height, material from which the conductor is fabricated or the like) and a switch constructed from a second electrical conductor having a second set of characteristics different than the first set of characteristics. In other embodiments, a switch can be a separate component, such as, for example, a microswitch, that is mounted to the printed circuit board. In yet other embodiments, an electrical circuit system can include a "pop-out" switch that includes a biasing member to bias the switch in a predetermined state. In yet other embodiments, an electrical circuit system can include a switch that is disposed at a location other than on a printed circuit board.

Similarly, although the switches 4972A and 4972B are shown and described as being irreversibly movable from a first state to a second state, in other embodiments, a switch can be reversibly movable between a first state and a second state. Moreover, in yet other embodiments, a switch can have more than two distinct states.

Although the actuators 4732, 4539 are shown and described as being configured to move in a direction substantially parallel to the surface of the substrate 4924, in other embodiments, an actuator can be configured to actuate an electronic circuit system by moving in any direction. For example, in some embodiments a circuit actuator can be moved in a direction substantially normal to a portion of an electronic circuit system.

Similarly, although the actuators 4732, 4539 are shown and described as actuating the switches 4972A and 4972B by tearing and/or deforming a portion of the substrate 4924, in other embodiments, a switch can be moved from a first state to a second state without deforming the substrate. For example, in some embodiments, an electronic circuit system can include a printed circuit board having a substrate and a frangible switch tab disposed on the substrate. An electrical conductor and/or a switch can be disposed on the frangible switch tab, such that when the switch tab is removed from the substrate the switch is moved from a first state to a second state. In this manner, the switch can be actuated without tearing and/or deforming a portion of the substrate.

Although the actuators 4732, 4539 are shown and described as being included on the safety lock 4710 and the base 4520, respectively, in other embodiments, the actuators can be included on any component of a medicament delivery device. For example, in some embodiments, an auto-injector can include a start button having an actuator configured to actuate an electronic circuit system. In other embodiments, an auto-injector can include a movable member configured to move a medicament container and/or a needle within a housing of the auto-injector, the movable member including an actuator configured to actuate an electronic circuit system.

Although the safety lock 4710 is shown and described as being removed from the housing 4110 of the auto-injector 4002 when in its second position, in other embodiments, a safety lock can remain coupled to the housing of an auto-injector when in its second position. For example, in some embodiments, a safety lock can be moved from its first position to its second position by rotating a portion of the safety lock.

Certain components of the auto-injector 4002 are shown and described as being coupled together via protrusions and mating openings. The protrusions and/or openings can be disposed on any of the components to be coupled together and need not be limited to only a certain component. For example, the safety lock 4710 is shown and described as including an actuator 4732 having a protrusion 4730 configured to be received within an opening 4928A defined by the substrate 4924. In some embodiments, however, the protrusions can be disposed on the substrate 4924 and the mating openings can be defined by the actuator 4732. In other embodiments, such components can be coupled together in any suitable way, which need not include protrusions and mating openings. For example, in some embodiments, an actuator can be operatively coupled to an actuation portion of a substrate via mating shoulders, clips, adhesive or the like.

Although the medical system 14000 shown as including a container 14040, a compliance tracking device 14010 and multiple medical injectors 14002A-14002G, each having at least one electronic circuit system (see e.g., electronic circuit systems 14050, 14020, 14080 and 14920), in some embodiments, a medical system can include only a container having multiple medical injectors. In such embodiments, the container can be a tray or other device configured to hold the medical injectors. The container can also perform the functions of the compliance monitoring device 14010, as described above. Moreover, in some embodiments, a medical injector can include a sheath similar to sheath 14070, wherein the sheath performs the electronic functions of the compliance monitoring device 14010 and/or the container 14050, as described above.

Although the electronic circuit systems are shown and described above as outputting recorded speech in English, in other embodiments, the electronic circuit system can output recorded speech in any language. In yet other embodiments, the electronic circuit system can output recorded speech in multiple languages.

Although some of the electronic circuit systems are shown and described above as including a proximity sensor, in other embodiments, an electronic circuit system can include any suitable sensor for providing feedback to the electronic circuit system. For example, in some embodiments, an electronic circuit system can include a pressure sensor configured to sense the internal gas pressure within a gas-powered auto-injector. In this manner, the electronic circuit system can output an instruction, a status message, and/or an electronic signal to a compliance tracking device when the internal gas pressure crosses a predetermined threshold. For example, in some embodiments, when the internal gas pressure rapidly increases, the electronic circuit system can output a message, such as, for example, "Internal gas chamber has been successfully punctured—injection is in process."

Similarly, in some embodiments, an electronic circuit system can include a temperature sensor configured to sense the temperature of the medicament contained within the medicament delivery device. In this manner, the electronic circuit system can output an instruction, a status message and/or an electronic signal to a compliance tracking device when the medicament is too cold for effective delivery. For example, in some embodiments, when the medicament is too cold for effective delivery (this may occur, for example, if the medicament delivery device has been left outside overnight or refrigerated for storage), the electronic circuit system can output a message, such as, for example, "MEDICAMENT IS TOO COLD—PLEASE BRISKLY RUB THE AUTO-INJECTOR BETWEEN YOUR HANDS." Similarly, in some embodiments, the electronic circuit system can output a message and/or a signal based upon the feedback from the temperature sensor, for example, indicating when the medicament will be at the appropriate temperature for delivery. For example, in some embodiments, the electronic circuit system can output a message stating "THE CURRENT MEDICAMENT TEMPERATURE IS XX DEGREES. PLEASE ALLOW THE MEDICAMENT TO STAND AT ROOM TEMPERATURE FOR APPROXIMATELY XX MINUTES BEFORE ADMINISTERING THE DOSE. PLEASE DO NOT MICROWAVE OR OTHERWISE HEAT THE MEDICAMENT." Similarly, in some embodiments, the electronic circuit system can output an electronic signal to a compliance tracking device so that the temperature data can be stored and/or transmitted to a remote device, as described herein.

Although the medicament delivery device 5002 is shown and described above as having an electronic circuit system 5920 including a first RFID tag 5921 and a second RFID tag 5923, in other embodiments, a medicament delivery device can have an electronic circuit system 5920 including only one RFID tag. Similarly, although the signal S6 output by the first RFID tag 5921 is shown and described above as having a characteristic different from the signal S7 output by the second RFID tag 5923, in other embodiments, the signal S6 can be the same as the signal S7.

Although various embodiments have been described as having particular features and/or combinations of components, other embodiments are possible having a combination of any features and/or components from any of embodiments where appropriate. For example, in some embodiments, a medicament delivery device can include an electronic circuit system configured to produce a first electronic signal when the device is actuated, similar to the medicament delivery device 3002, and a second electronic signal based upon the impedance between various portions of the device, similar to the medicament delivery device 15002.

What is claimed is:

1. A method, comprising:
    manipulating an actuator coupled to a medical injector such that a first portion of the actuator initiates delivery of a medicament from a medicament container that is at least partially disposed within a container housing of the medical injector via a needle configured to penetrate skin and a second portion of the actuator moves at least one of a switch or a sensor of an electronic circuit system coupled to the medical injector; and
    outputting, from the electronic circuit system, an electronic signal in response to the moving one of the switch or the sensor, the electronic signal being a short-range radio frequency signal.

2. The method of claim 1, wherein the medical injector is any one of an autoinjector or a pen injector.

3. The method of claim 1, wherein:
    the electronic signal is a first electronic signal; and
    the electronic circuit system includes a processor and a pressure sensor configured to transmit a second electronic signal to the processor in response to a pressure exerted on the pressure sensor.

4. The method of claim 1, wherein the manipulating the actuator causes the first portion of the actuator and the second portion of the actuator to move together.

5. The method of claim 1, wherein the manipulating the actuator causes an energy storage member to produce a force that moves an elastomeric member within the medicament container to deliver the medicament.

6. The method of claim 1, wherein:
    the switch is a reversible switch; and
    the manipulating the actuator causes the second portion of the actuator to move the switch.

7. An apparatus, comprising:
    a medical injector including a medicament container, a housing configured to receive the medicament container, a needle configured to be placed in fluid communication with the medicament container, and an actuator movably coupled to the housing, the medical injector configured to be actuated by moving a first portion of the actuator relative to the housing; and
    an electronic circuit system coupled to the medical injector, the electronic circuit system including at least one of a switch or a sensor and a wireless communications module, the electronic circuit system configured to produce a first output when the at least one of the switch or the sensor is moved from a first state to a second state, the at least one of the switch or the sensor moved from the first state to the second state by movement of a second portion of the actuator, the second portion of the actuator configured to move when the first portion of the actuator is moved, the electronic circuit system configured to output, via the wireless communication module, a compliance signal associated with the actuation of the medical injector, the compliance signal being a short-range radio frequency signal.

8. The apparatus of claim 7, wherein the medical injector is any one of an autoinjector or a pen injector.

9. The apparatus of claim 7, wherein the wireless communications module is implemented at least in part in hardware, the wireless communications module configured to send one or more electronic signals to a plurality of communication devices via a wireless communications network.

10. The apparatus of claim 7, wherein the wireless communications module is implemented at least in part in hardware and includes at least one of a microprocessor, a transmitter, a receiver, a transceiver, a microchip, a radio chipset, a wireless interface card (WIC), a host controller interface (HCI), a universal asynchronous receiver or transmitter (UART), a power source, a sensor, a transponder, an antenna, a crystal, a circuit board, a liquid crystal display (LCD), a Small Computer System Interface (SCSI), a FireWire, a data uplink, a data downlink, a point-to-point link, a fiber optic link, a storage device, a personal computer card, a docking station, a parallel and/or bit-serial connection, a Universal Serial Bus (USB) port, a light emitting diode, a speaker, an amplifier, or a radiofrequency identification device (RFID).

11. The apparatus of claim 7, wherein the wireless communications module is implemented at least in part in hardware and includes a single chip containing components used for wireless communication.

12. The apparatus of claim 7, wherein the compliance signal includes a time stamp associated with the actuation of the medical injector.

13. The apparatus of claim 7, wherein:
the housing of the medical injector defines an internal volume within which the medicament container is received; and
the electronic circuit system is coupled to the medical injector such that the at least one of the switch or the sensor is outside of the internal volume.

14. The apparatus of claim 13, wherein the second portion of the actuator engages the at least one of the switch or the sensor to move the at least one of the switch or the sensor from the first state to the second state.

15. The apparatus of claim 7, wherein movement of the first portion of the actuator causes an injection force to be exerted on an elastomeric member within the medicament container; the injection force produced non-electronically.

16. The apparatus of claim 15, wherein the injection force is produced by any one of a spring or a pressurized gas.

17. A method of delivering a medicament from a medical injector, comprising:
removing a safety member from an end portion of a housing of the medical injector, the medical injector including a medicament container, a needle configured to be placed in fluid communication with the medicament container, an actuator, and an electronic circuit system coupled to the housing, the needle configured to penetrate skin, the safety member covering the needle before the removing; and
manipulating the actuator to cause:
a first portion of the actuator to move to initiate delivery of the medicament from the medicament container via the needle; and
a second portion of the actuator to move one of a switch or a sensor of the electronic circuit system, the electronic circuit system producing a short-range radio frequency signal in response to the second portion of the actuator moving one of the switch or the sensor.

18. The method of claim 17, wherein the manipulating the actuator causes the first portion of the actuator and the second portion of the actuator to move together.

19. The method of claim 17, wherein movement of the first portion of the actuator causes an energy storage member to produce a force that moves an elastomeric member within the medicament container to deliver the medicament.

20. The method of claim 17, wherein:
the electronic circuit system includes at least one of a light output device or an audible output device; and
the electronic circuit system produces at least one of a light output via the light output device or an audible output via the audible output device in response to any one the removing a safety member or the second portion of the actuator engaging one of the switch or the sensor.

21. The method of claim 17, wherein the medical injector is an auto-injector containing a dose of epinephrine.

* * * * *